(12) United States Patent
Fuji et al.

(10) Patent No.: US 9,791,341 B2
(45) Date of Patent: Oct. 17, 2017

(54) PRESSURE SENSOR, MICROPHONE, BLOOD PRESSURE SENSOR, AND TOUCH PANEL

(71) Applicant: Kabushiki Kaisha Toshiba, Minato-ku (JP)

(72) Inventors: Yoshihiko Fuji, Kawasaki (JP); Hideaki Fukuzawa, Kawasaki (JP); Michiko Hara, Yokohama (JP); Tomohiko Nagata, Yokohama (JP); Akio Hori, Kawasaki (JP); Shiori Kaji, Kawasaki (JP); Yoshihiro Higashi, Komatsu (JP); Akiko Yuzawa, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 532 days.

(21) Appl. No.: 14/469,876

(22) Filed: Aug. 27, 2014

(65) Prior Publication Data

US 2015/0088008 A1     Mar. 26, 2015

(30) Foreign Application Priority Data

Sep. 20, 2013 (JP) ................................. 2013-196065

(51) Int. Cl.
*G01L 9/16* (2006.01)
*A61B 5/021* (2006.01)
(Continued)

(52) U.S. Cl.
CPC ................ *G01L 9/16* (2013.01); *A61B 5/021* (2013.01); *A61B 5/02141* (2013.01);
(Continued)

(58) Field of Classification Search
CPC ....... G01L 9/0001; G01L 9/16; G01L 9/0041; G01L 1/125
See application file for complete search history.

(56) References Cited

U.S. PATENT DOCUMENTS

2006/0246271 A1   11/2006   Quandt et al.
2006/0251928 A1   11/2006   Quandt et al.
(Continued)

FOREIGN PATENT DOCUMENTS

DE   10 2011 082 122 A1   3/2013
JP   2007-180201           7/2007
(Continued)

OTHER PUBLICATIONS

Decision to Grant a Patent issued Dec. 8, 2016 in Japanese Patent Application No. 2013-196065.
(Continued)

*Primary Examiner* — Erika J Villaluna
(74) *Attorney, Agent, or Firm* — Oblon, McClelland, Maier & Neustadt, L.L.P.

(57) ABSTRACT

According to one embodiment, a pressure sensor includes a support, a film unit supported by the support, having an upper surface, and capable of being deformed, and a first sensing element provided on the upper surface. The first sensing element includes a first magnetic layer, a second magnetic layer provided apart from the first magnetic layer and a first intermediate unit including a first intermediate layer including a portion provided between the first and second magnetic layers. The first magnetic layer extends in a first direction parallel to the upper surface, and a first major axis length of the first magnetic layer is longer than a first minor axis length. The second magnetic layer extends in a second direction parallel to the upper surface and crossing the first direction, and a second major axis length of the second magnetic layer is longer than a second minor axis length.

30 Claims, 27 Drawing Sheets

(51) Int. Cl.
*G01L 9/00* (2006.01)
*G06F 3/041* (2006.01)
*H04R 19/00* (2006.01)
*H04R 19/04* (2006.01)
*H04R 31/00* (2006.01)
*A61B 5/00* (2006.01)

(52) U.S. Cl.
CPC .......... *G01L 9/0001* (2013.01); *G06F 3/0414* (2013.01); *H04R 19/005* (2013.01); *H04R 19/04* (2013.01); *H04R 31/00* (2013.01); *A61B 5/6824* (2013.01); *A61B 2562/0247* (2013.01)

(56) References Cited

U.S. PATENT DOCUMENTS

2012/0079887 A1   4/2012   Giddings et al.
2012/0245477 A1   9/2012   Giddings et al.
2013/0076687 A1   3/2013   Giddings et al.
2013/0170669 A1   7/2013   Fukuzawa et al.

FOREIGN PATENT DOCUMENTS

| JP | 4355439 B2 | 11/2009 |
| JP | 2012-204479 A | 10/2012 |
| JP | 5235964 B2 | 7/2013 |
| JP | 5677258 B2 | 2/2015 |
| JP | 5740268 B2 | 6/2015 |
| JP | 5940639 B2 | 6/2016 |

OTHER PUBLICATIONS

M. Löhndorf, et al., "Highly Sensitive Strain Sensors Based on Magnetic Tunneling Junctions," Applied Physics Letters, vol. 81, No. 2, Jul. 8, 2002, pp. 313-315.

D. Meyners, et al., "Pressure Sensor Based on Magnetic Tunnel Junctions," Journal of Applied Physics 105, 2009, pp. 07C914-1-07C914-3.

FIG. 13A
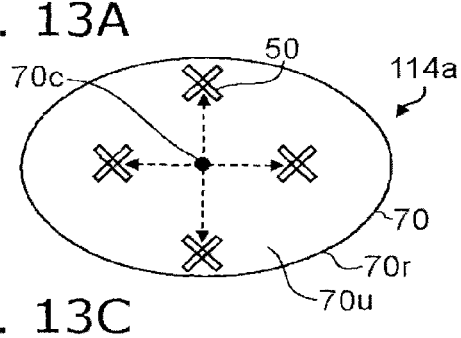
FIG. 13B
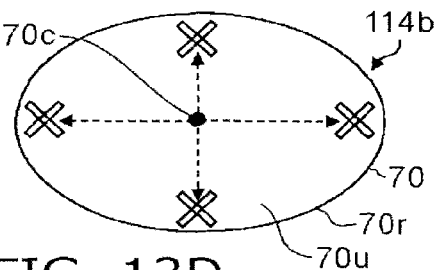
FIG. 13C
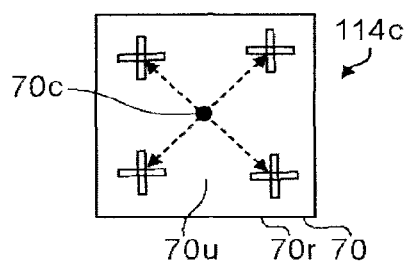
FIG. 13D
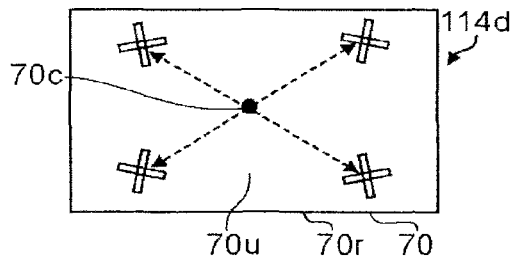
FIG. 14A
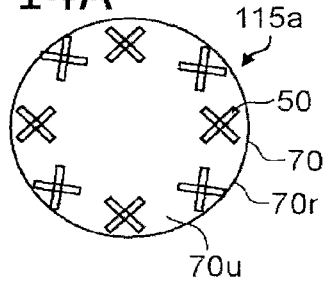
FIG. 14B
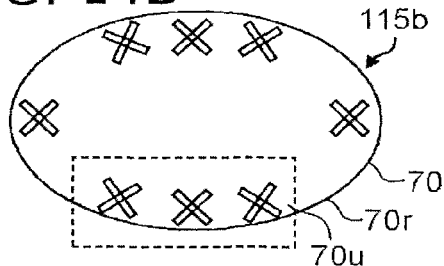
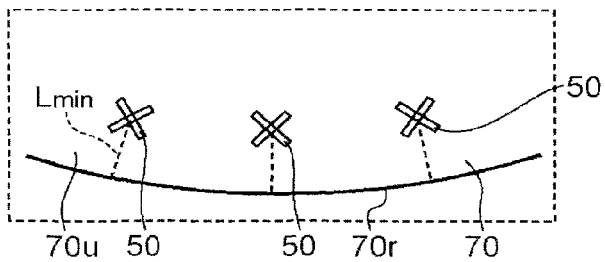
FIG. 14C
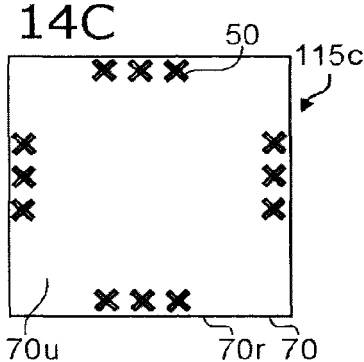
FIG. 14D
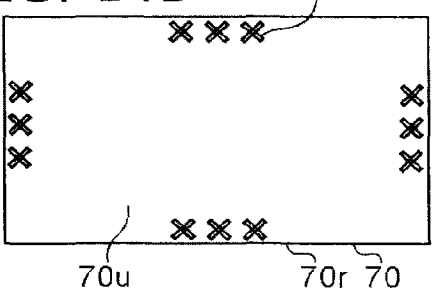

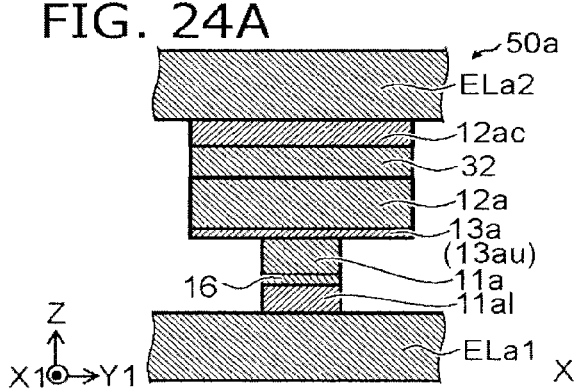
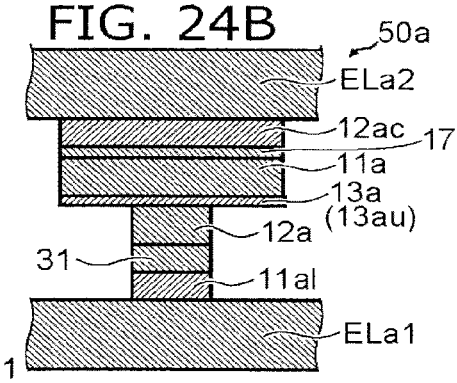
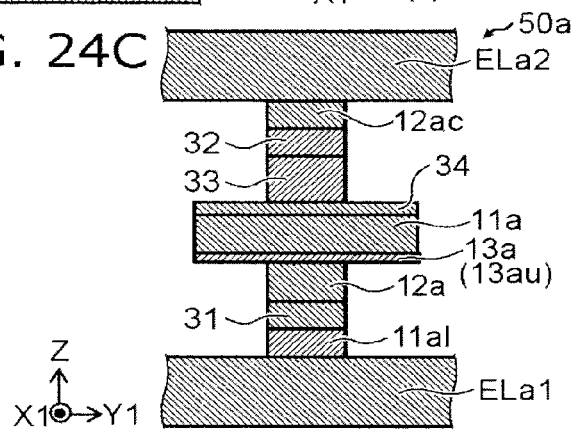
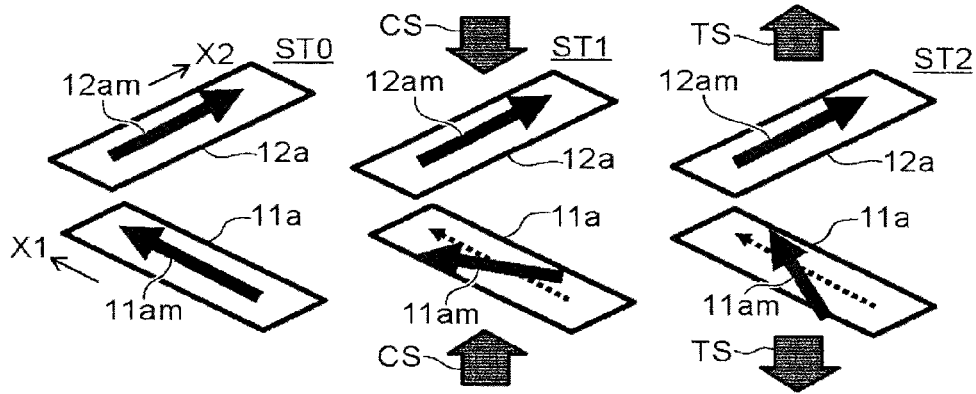
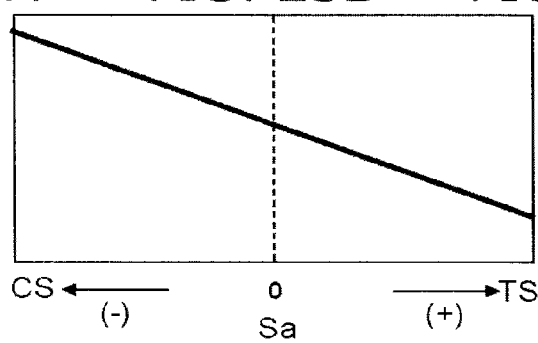

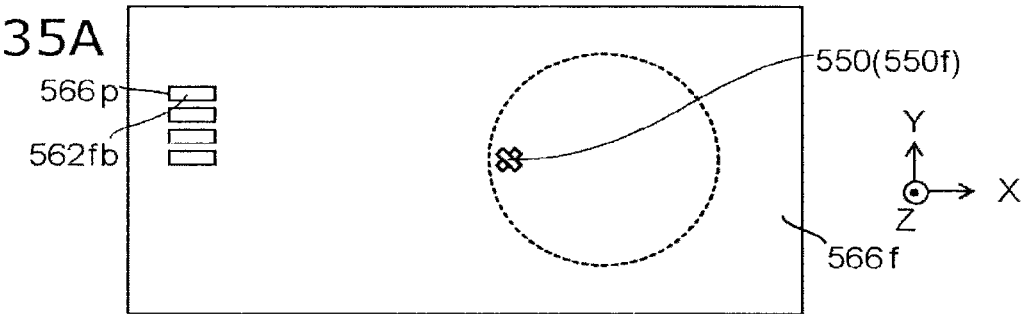
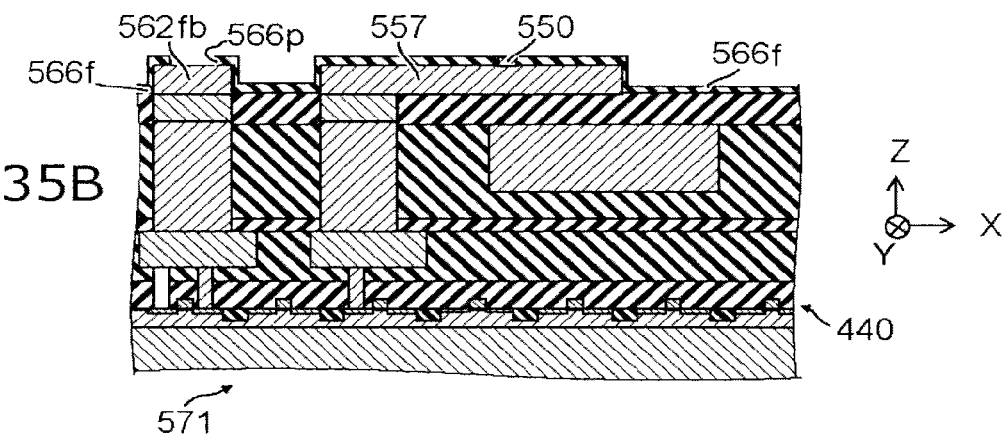
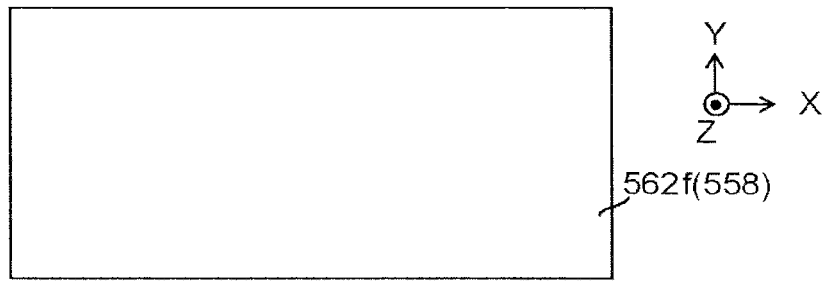
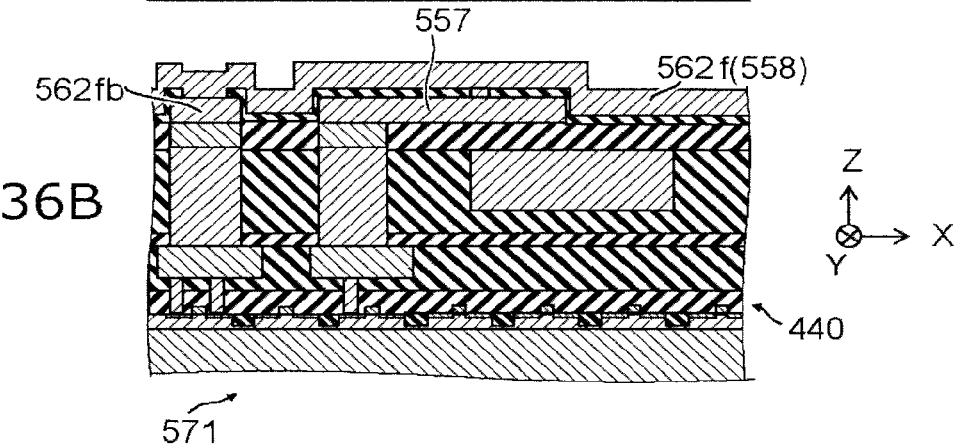

PRESSURE SENSOR, MICROPHONE, BLOOD PRESSURE SENSOR, AND TOUCH PANEL

CROSS-REFERENCE TO RELATED APPLICATIONS

This application is based upon and claims the benefit of priority from Japanese Patent Application No. 2013-196065, filed on Sep. 20, 2013; the entire contents of which are incorporated herein by reference.

FIELD

Embodiments described herein relate generally to a pressure sensor, a microphone, a blood pressure sensor, and a touch panel.

BACKGROUND

For pressure sensors using MEMS (micro electro mechanical systems) technology, there are a piezoresistance change type and an electrostatic capacitance type, for example. On the other hand, a pressure sensor using spin technology is proposed. In the pressure sensor using spin-electronics technology, a resistance change in accordance with strain is sensed. A high-sensitivity pressure sensor using spin technology is desired.

BRIEF DESCRIPTION OF THE DRAWINGS

FIG. 13A to FIG. 13D are schematic plan views showing pressure sensors according to the first embodiment;
FIG. 14A to FIG. 14D are schematic plan views showing pressure sensors according to the first embodiment;
FIG. 24A to FIG. 24C are schematic cross-sectional views showing pressure sensors according to the first embodiment;
FIG. 25A to FIG. 25D are schematic diagrams showing the pressure sensor according to the first embodiment;
FIG. 35A and FIG. 35B are schematic views showing a method for manufacturing a pressure sensor according to a third embodiment;
FIG. 36A and FIG. 36B are schematic views showing a method for manufacturing a pressure sensor according to a third embodiment.

DETAILED DESCRIPTION

Figure 1A:
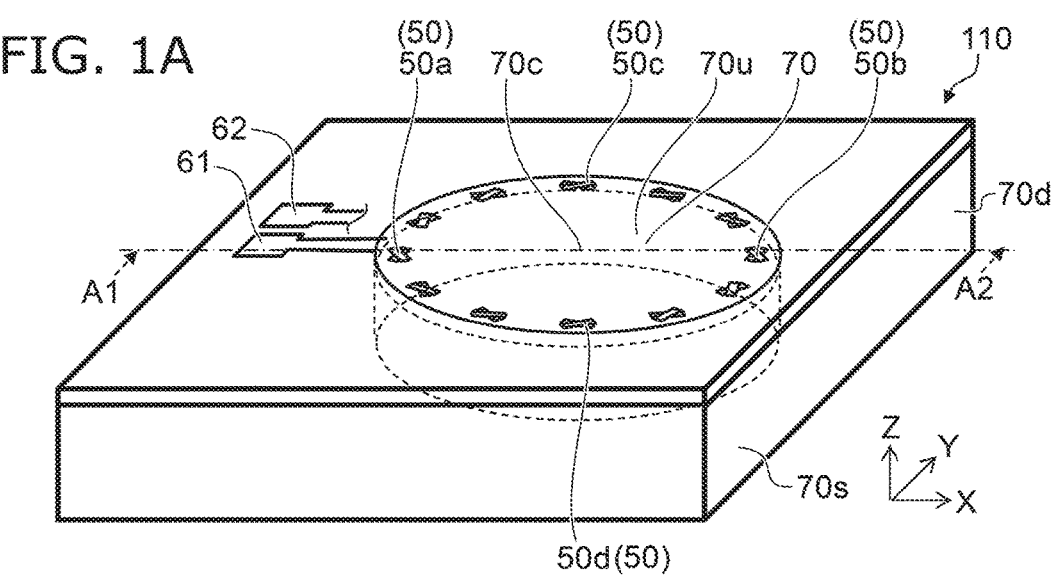
FIG. 1A and FIG. 1B are schematic views showing a pressure sensor according to a first embodiment.

According to one embodiment, a pressure sensor includes a support, a film unit and a first sensing element. The film unit is supported by the support. The film unit has an upper surface. The film unit is deformable. The first sensing element is provided on the upper surface. The first sensing element includes a first magnetic layer in which a magnetization changes in accordance with a deformation of the film unit, a second magnetic layer provided apart from the first magnetic layer in a direction crossing the upper surface, and a first intermediate unit including a first intermediate layer including a portion provided between the first magnetic layer and the second magnetic layer. The first magnetic layer extends in a first direction parallel to the upper surface, and a first major axis length of the first magnetic layer in the first direction is longer than a first minor axis length of the first magnetic layer in a direction parallel to the upper surface and crossing the first direction. The second magnetic layer extends in a second direction parallel to the upper surface and crossing the first direction, and a second major axis length of the second magnetic layer in the second direction is longer than a second minor axis length of the second magnetic layer in a direction parallel to the upper surface and crossing the second direction.

According to one embodiment, a microphone includes a pressure sensor. The pressure sensor includes a support, a film unit and a first sensing element. The film unit is supported by the support. The film unit has an upper surface. The film unit is deformable. The first sensing element is provided on the upper surface. The first sensing element includes a first magnetic layer in which a magnetization changes in accordance with a deformation of the film unit, a second magnetic layer provided apart from the first magnetic layer in a direction crossing the upper surface, and a first intermediate unit including a first intermediate layer including a portion provided between the first magnetic layer and the second magnetic layer. The first magnetic layer extends in a first direction parallel to the upper surface, and a first major axis length of the first magnetic layer in the first direction is longer than a first minor axis length of the first magnetic layer in a direction parallel to the upper surface and crossing the first direction. The second magnetic layer extends in a second direction parallel to the upper surface and crossing the first direction, and a second major axis length of the second magnetic layer in the second direction is longer than a second minor axis length of the second magnetic layer in a direction parallel to the upper surface and crossing the second direction.

According to one embodiment, a blood pressure sensor includes a pressure sensor. The pressure sensor includes a support, a film unit and a first sensing element. The film unit is supported by the support. The film unit has an upper surface. The film unit is deformable. The first sensing element is provided on the upper surface. The first sensing element includes a first magnetic layer in which a magnetization changes in accordance with a deformation of the film unit, a second magnetic layer provided apart from the first magnetic layer in a direction crossing the upper surface, and a first intermediate unit including a first intermediate layer including a portion provided between the first magnetic layer and the second magnetic layer. The first magnetic layer extends in a first direction parallel to the upper surface, and a first major axis length of the first magnetic layer in the first direction is longer than a first minor axis length of the first magnetic layer in a direction parallel to the upper surface and crossing the first direction. The second magnetic layer extends in a second direction parallel to the upper surface and crossing the first direction, and a second major axis length of the second magnetic layer in the second direction is longer than a second minor axis length of the second magnetic layer in a direction parallel to the upper surface and crossing the second direction.

According to one embodiment, a touch panel includes a pressure sensor. The pressure sensor includes a support, a film unit and a first sensing element. The film unit is supported by the support. The film unit has an upper surface. The film unit is deformable. The first sensing element is provided on the upper surface. The first sensing element includes a first magnetic layer in which a magnetization changes in accordance with a deformation of the film unit, a second magnetic layer provided apart from the first magnetic layer in a direction crossing the upper surface, and a first intermediate unit including a first intermediate layer including a portion provided between the first magnetic layer and the second magnetic layer. The first magnetic layer extends in a first direction parallel to the upper surface, and a first major axis length of the first magnetic layer in the first direction is longer than a first minor axis length of the first magnetic layer in a direction parallel to the upper surface and crossing the first direction. The second magnetic layer extends in a second direction parallel to the upper surface and crossing the first direction, and a second major axis length of the second magnetic layer in the second direction is longer than a second minor axis length of the second magnetic layer in a direction parallel to the upper surface and crossing the second direction.

Various embodiments will be described hereinafter with reference to the accompanying drawings.

The drawings are schematic or conceptual; and the relationships between the thickness and width of portions, the proportions of sizes among portions, etc. are not necessarily the same as the actual values thereof. Further, the dimensions and proportions may be illustrated differently among drawings, even for identical portions.

In the specification of this application and the drawings, components similar to those described in regard to a drawing thereinabove are marked with the same reference numerals, and a detailed description is omitted as appropriate.

First Embodiment

Figure 1B:
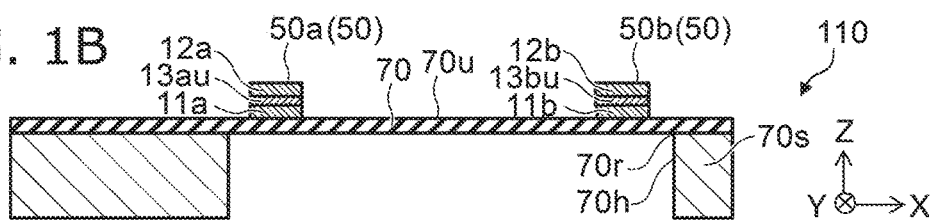

FIG. 1A and FIG. 1B are schematic views illustrating a pressure sensor according to a first embodiment.

FIG. 1A is a perspective view. FIG. 1B is a cross-sectional view taken along line A1-A2 of FIG. 1A.

As shown in FIG. 1A and FIG. 1B, a pressure sensor 110 according to the embodiment includes a film unit 70 and a first sensing element 50a.

The film unit 70 has an upper surface 70u. The film unit 70 has flexibility. The upper surface 70u includes a flexible region. The film unit 70 is deformable. The film unit 70 is supported by a support 70s, for example.

The support 70s is a substrate, for example. The film unit 70 is a diaphragm, for example. The film unit 70 may be integrated with or separated from the support 70s. For the film unit 70, the same material as the support 70s may be used, or a different material from the support 70s may be used. Part of a substrate that forms the support 70s may be removed, and a portion of the substrate with a smaller thickness may form the film unit 70.

The thickness of the film unit 70 is smaller than the thickness of the support 70s. In the case where the same material is used for the film unit 70 and the support 70s and they are integrated together, a portion with a smaller thickness forms the film unit 70, and a portion with a larger thickness forms the support 70s.

The support 70s may have a through hole 70h penetrating through the support 70s in the thickness direction, and the film unit 70 may be provided so as to cover the through hole 70h, for example. At this time, the film of the material that forms the film unit 70 may extend also on a portion other than the through hole of the support 70s, for example. At this time, of the film of the material that forms the film unit 70, a portion overlapping the through hole 70h forms the film unit 70.

The film unit 70 has an outer edge 70r. In the case where the same material is used for the film unit 70 and the support 70s and they are integrated together, the outer edge of the portion with a smaller thickness is the outer edge 70r of the film unit 70. In the case where the support 70s has the through hole 70h penetrating through the support 70s in the thickness direction and the film unit 70 is provided so as to cover the through hole 70h, the outer edge of the portion overlapping the through hole 70h of the film of the material that forms the film unit 70 is the outer edge 70r of the film unit 70.

The support 70s may continuously support the outer edge 70r of the film unit 70, and may support part of the outer edge 70r of the film unit 70.

The first sensing element 50a is provided on the upper surface 70u of the film unit 70.

In the specification of this application, the state of being "provided on" includes not only the state of being provided in direct contact but also the state of being provided via another component.

In this example, a plurality of sensing elements 50 are provided on the film unit 70. The sensing element 50 includes a first to a fourth sensing element 50a to 50d, for example. The number of sensing elements 50 provided on the film unit 70 may be one. The number of sensing elements 50 may be 5 or more.

In this example, a first interconnection 61 and a second interconnection 62 are provided in the pressure sensor 110. The first interconnection 61 and the second interconnection 62 are connected to the sensing element 50. An interlayer insulation film is provided between the first interconnection 61 and the second interconnection 62, for example, and the first interconnection 61 and the second interconnection 62 are electrically insulated. A voltage is applied between the first interconnection 61 and the second interconnection 62, and the voltage is applied to the sensing element 50 via the first interconnection 61 and the second interconnection 62. When a pressure is applied to the pressure sensor 110, the film unit 70 is deformed. In the sensing element 50, the electric resistance changes in accordance with the deformation of the film unit 70. The pressure is sensed by sensing the change in electric change via the first interconnection 61 and the second interconnection 62.

The direction perpendicular to the upper surface 70u of the film unit 70 is defined as the Z-axis direction. One direction perpendicular to the Z-axis direction is defined as the X-axis direction. The direction perpendicular to the Z-axis direction and the X-axis direction is defined as the Y-axis direction.

The film unit 70 has a centroid 70c, for example. The centroid 70c is the centroid of the shape of the film unit 70 when the film unit 70 is projected onto the X-Y plane. The centroid 70c is the centroid in the X-Y plane of the shape of the film unit 70. The centroid 70c corresponds to the centroid of the upper surface 70u of the film unit 70.

In this example, the line connecting the first sensing element 50a and the second sensing element 50b passes through the centroid 70c. That is, the centroid 70c of the film unit 70 is disposed between the first sensing element 50a and the second sensing element 50b. The line connecting the third sensing element 50c and the fourth sensing element 50d passes through the centroid 70c. That is, the centroid 70c of the film unit 70 is disposed between the third sensing element 50c and the fourth sensing element 50d. In this example, the line connecting the third sensing element 50c and the fourth sensing element 50d crosses the line connecting the first sensing element 50a and the second sensing element 50b.

Examples of the first to fourth sensing elements 50a to 50d will now be described.

FIG. 2A to FIG. 2D are schematic perspective views illustrating the pressure sensor according to the first embodiment.

FIG. 2A to FIG. 2D show examples of the first to fourth sensing elements 50a to 50d, respectively. In the drawings, the film unit 70 (and the upper surface 70u of the film unit 70) is omitted.

Figure 2A:
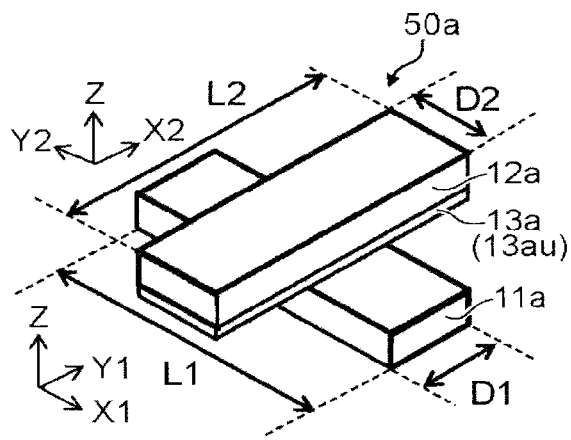
FIG. 2A to FIG. 2D are schematic perspective views showing the pressure sensor according to the first embodiment.

As shown in FIG. 2A, the first sensing element 50a includes a first magnetic layer 11a, a second magnetic layer 12a, and a first intermediate unit 13au. The first sensing element 50a is provided on part of the upper surface 70u of the film unit 70.

The magnetization of the first magnetic layer 11a (the direction thereof) is variable. The first magnetic layer 11a is a magnetization free layer, for example.

The second magnetic layer 12a is apart from the first magnetic layer 11a in a direction crossing the upper surface 70u (for example, the Z-axis direction). As illustrated in FIG. 1B, the first magnetic layer 11a is disposed between the second magnetic layer 12a and the film unit 70, for example. In the embodiment, the second magnetic layer 12a may be disposed between the first magnetic layer 11a and the film unit 70.

The first intermediate unit 13au includes a first intermediate layer 13a. The first intermediate layer 13a includes a portion provided between the first magnetic layer 11a and the second magnetic layer 12a.

The first magnetic layer 11a extends in a first direction X1. The first direction X1 is substantially parallel to the upper surface 70u, for example. A first major axis length L1 of the first magnetic layer 11a in the first direction X1 is longer than a first minor axis length D1 of the first magnetic layer 11a in a direction Y2 substantially parallel to the upper surface 70u and crossing (for example, orthogonal to) the first direction X1.

The second magnetic layer 12a extends in a second direction X2. The second direction X2 is substantially parallel to the upper surface 70u and crosses the first direction X1, for example. A second major axis length L2 of the second magnetic layer 12a in the second direction X2 is longer than a second minor axis length D2 of the second magnetic layer 12a in a direction Y2 substantially parallel to the upper surface 70u and crossing (for example, orthogonal to) the second direction X2.

The second sensing element 50b is provided on part of the upper surface 70u of the film unit 70.

Figure 2B:
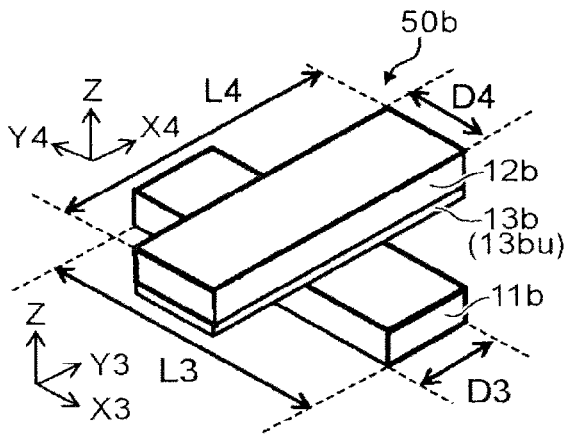

As shown in FIG. 2B, the second sensing element 50b includes a third magnetic layer 11b, a fourth magnetic layer 12b, and a second intermediate unit 13bu. The magnetization of the third magnetic layer 11b (the direction thereof) is variable. The third magnetic layer 11b is a magnetization free layer, for example.

The fourth magnetic layer 12b is apart from the third magnetic layer 11b in a direction crossing the upper surface 70u (for example, the Z-axis direction). As illustrated in FIG. 1B, the third magnetic layer 11b is disposed between the fourth magnetic layer 12b and the film unit 70, for example. In the embodiment, the fourth magnetic layer 12b may be disposed between the third magnetic layer 11b and the film unit 70.

The second intermediate unit 13bu includes a second intermediate layer 13b. The second intermediate layer 13b includes a portion provided between the third magnetic layer 11b and the fourth magnetic layer 12b.

The third magnetic layer 11b extends in a third direction X3. The third direction X3 is substantially parallel to the upper surface 70u, for example. A third major axis length L3 of the third magnetic layer 11b in the third direction X3 is longer than a third minor axis length D3 of the third magnetic layer 11b in a direction Y3 substantially parallel to the upper surface 70u and crossing (for example, orthogonal to) the third direction X3.

The fourth magnetic layer 12b extends in a fourth direction X4. The fourth direction X4 is substantially parallel to the upper surface 70u and crosses the third direction X3, for example. A fourth major axis length L4 of the fourth magnetic layer 12b in the fourth direction X4 is longer than a fourth minor axis length D4 of the fourth magnetic layer 12b in a direction Y4 substantially parallel to the upper surface 70u and crossing (for example, orthogonal to) the fourth direction X4.

The third direction X3 may run along the first direction X1, for example. The third direction X3 may be parallel to the first direction X1, for example. The absolute value of the angle between the first direction X1 and the third direction X3 may be 5 degrees or less. As described later, the third direction X3 and the first direction X1 may cross each other. Examples of the angle between the first direction X1 and the third direction X3 are described later.

The third sensing element 50c is provided on part of the upper surface 70u.

Figure 2C:
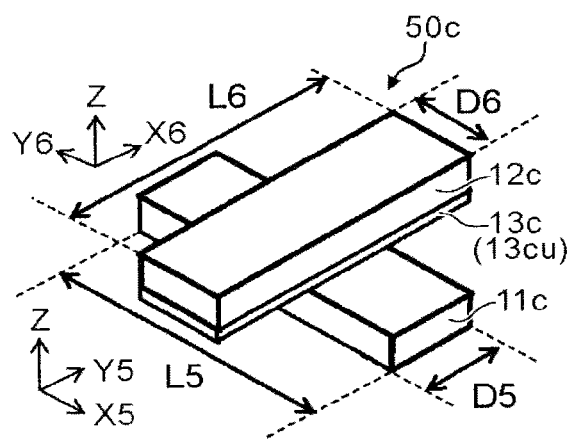

As shown in FIG. 2C, the third sensing element 50c includes a fifth magnetic layer 11c, a sixth magnetic layer 12c, and a third intermediate unit 13cu.

The magnetization of the fifth magnetic layer 11c (the direction thereof) is variable. The fifth magnetic layer 11c is a magnetization free layer, for example.

The sixth magnetic layer 12c is apart from the fifth magnetic layer 11c in a direction crossing the upper surface 70u (for example, the Z-axis direction). The fifth magnetic layer 11c is disposed between the sixth magnetic layer 12c and the film unit 70, for example. In the embodiment, the sixth magnetic layer 12c may be disposed between the fifth magnetic layer 11c and the film unit 70.

The third intermediate unit 13cu includes a third intermediate layer 13c. The third intermediate layer 13c includes a portion provided between the fifth magnetic layer 11c and the sixth magnetic layer 12c.

The fifth magnetic layer 11c extends in a fifth direction X5. The fifth direction X5 is substantially parallel to the upper surface 70u, for example. A fifth major axis length L5 of the fifth magnetic layer 11c in the fifth direction X5 is longer than a fifth minor axis length D5 of the fifth magnetic layer 11c in a direction Y5 substantially parallel to the upper surface 70u and crossing (for example, orthogonal to) the fifth direction X5.

The sixth magnetic layer 12c extends in a sixth direction X6. The sixth direction X6 is substantially parallel to the upper surface 70u and crosses the fifth direction X5, for example. A sixth major axis length L6 of the sixth magnetic layer 12c in the sixth direction X6 is longer than a sixth minor axis length D6 of the sixth magnetic layer 12c in a direction Y6 substantially parallel to the upper surface 70u and crossing (for example, orthogonal to) the sixth direction X6.

The fourth sensing element 50d is provided on part of the upper surface 70u.

Figure 2D:
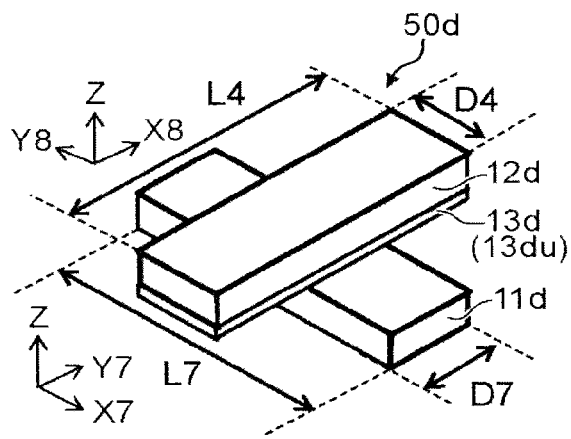

As shown in FIG. 2D, the fourth sensing element 50d includes a seventh magnetic layer 11d, an eighth magnetic layer 12d, and a fourth intermediate unit 13du.

The magnetization of the seventh magnetic layer 11d (the direction thereof) is variable. The seventh magnetic layer 11d is a magnetization free layer, for example.

The eighth magnetic layer 12d is apart from the seventh magnetic layer 11d in a direction crossing the upper surface 70u (for example, the Z-axis direction). The seventh magnetic layer 11d is disposed between the eighth magnetic layer 12d and the film unit 70, for example. In the embodiment, the eighth magnetic layer 12d may be disposed between the seventh magnetic layer 11d and the film unit 70.

The fourth intermediate unit 13du includes a fourth intermediate layer 13d. The fourth intermediate layer 13d includes a portion provided between the seventh magnetic layer 11d and the eighth magnetic layer 12d.

The seventh magnetic layer 11d extends in a seventh direction X7. The seventh direction X7 is substantially parallel to the upper surface 70u, for example. A seventh major axis length L7 of the seventh magnetic layer 11d in the seventh direction X7 is longer than a seventh minor axis length D7 of the seventh magnetic layer 11d in a direction Y7 substantially parallel to the upper surface 70u and crossing (for example, orthogonal to) the seventh direction X7.

The eighth magnetic layer 12d extends in an eighth direction 8. The eighth direction X8 is substantially parallel to the upper surface 70u and crosses the seventh direction X7, for example. An eighth major axis length L8 of the eighth magnetic layer 12d in the eighth direction X8 is longer than an eighth minor axis length D8 of the eighth magnetic layer 11d in a direction Y8 substantially parallel to the upper surface 70u and crossing (for example, orthogonal to) the eighth direction X8.

A nonmagnetic material may be used for the first intermediate layer 13a, the second intermediate layer 13b, the third intermediate layer 13c, and the fourth intermediate layer 13d, for example.

The magnetization of the magnetic layers mentioned above can change in accordance with the deformation of the film unit 70. In the embodiment, the planar shape of the first magnetic layer 11a and the planar shape of the second magnetic layer 12a have shape anisotropy. The planar shape of each of the third magnetic layer 11b, the fourth magnetic layer 12b, the fifth magnetic layer 11c, the sixth magnetic layer 12c, the seventh magnetic layer 11d, and the eighth magnetic layer 12d has shape anisotropy. The planar shape of each of these magnetic layers is a substantially rectangular shape, for example. The planar shape of each of these magnetic layers is a rectangle, for example. In the first magnetic layer 11a, the extending direction of the long side of the rectangle corresponds to the first direction X1, for example. The short side corresponds to the direction Y1. In the second magnetic layer 12a, the extending direction of the long side of the rectangle corresponds to the second direction X2. The short side corresponds to the direction Y1.

In the pressure sensor 110 according to the embodiment, the magnetic layers included in the sensing element 50 have shape anisotropy and the extending directions of the magnetic layers cross each other; thereby, a high-sensitivity pressure sensor can be provided.

Examples of the pressure sensor 110 will now be described.

As the support 70s, a plate-like substrate may be used, for example. A hollow portion (for example, the through hole 70h) is provided in the substrate, for example.

For the support 70s, a semiconductor material such as silicon, a conductive material such as a metal, or an insulating material may be used, for example. The support 70s may contain silicon oxide, silicon nitride, or the like, for example. The interior of the hollow portion is in a reduced pressure state (vacuum state), for example. The interior of the hollow portion may be filled with a gas such as air or a liquid. The interior of the hollow portion is designed so that the film unit can bend. The interior of the hollow portion may be connected to the outside air.

The film unit 70 is provided on the hollow portion. As the film unit 70, a portion thinned by processing of a substrate that forms the support 70s is used, for example. The thickness (the length in the Z-axis direction) of the film unit 70 is smaller than the thickness (the length in the Z-axis direction) of the substrate.

When a pressure is applied to the film unit 70, the film unit 70 bends. The pressure corresponds to the pressure that is to be sensed by the pressure sensor 110. The applied pressure includes pressure caused by sound waves, ultrasonic waves, or the like. In the case of sensing pressure caused by sound waves, ultrasonic waves, or the like, the pressure sensor 110 functions as a microphone.

For the film unit 70, an insulating material is used, for example. The film unit 70 contains at least one of silicon oxide, silicon nitride, and silicon oxynitride, for example. A semiconductor material such as silicon may be used for the film unit 70, for example. A metal material may be used for the film unit 70, for example.

The thickness of the film unit 70 is not less than 0.1 micrometers (μm) and not more than 3 μm, for example. The thickness is preferably not less than 0.2 μm and not more than 1.5 μm. A stacked film including a silicon oxide film with a thickness of 0.2 μm and a silicon film with a thickness of 0.4 μm may be used as the film unit 70, for example.

As the first magnetic layer 11a and the second magnetic layer 12a, a ferromagnetic layer is used, for example. The first magnetic layer 11a is a magnetization free layer, for example. The second magnetic layer 12a is a reference layer, for example. As the reference layer, a magnetization fixed layer or a magnetization free layer is used. The change in magnetization of the first magnetic layer 11a is easier than the change in magnetization of the second magnetization layer 12a, for example. Thereby, when a pressure is applied, a change can be made to the relative angle between the magnetization of the first magnetic layer 11a and the magnetization of the second magnetic layer 12a, as described later.

Similarly, a change can be made to the relative angle between the magnetization of the third magnetic layer 11b and the magnetization of the fourth magnetic layer 12b. A change can be made to the relative angle between the magnetization of the fifth magnetic layer 11c and the magnetization of the sixth magnetic layer 12c. A change can be made to the relative angle between the magnetization of the seventh magnetic layer 11d and the magnetization of the eighth magnetic layer 12d. The following description about the first magnetic layer 11a can be applied to the third magnetic layer 11b, the fifth magnetic layer 11c, and the seventh magnetic layer 11d. The following description about the second magnetic layer 12a can be applied to the fourth magnetic layer 12b, the sixth magnetic layer 12c, and the eighth magnetic layer 12d. The following description about the first intermediate layer 13a can be applied to the second intermediate layer 13b, the third intermediate layer 13c, and the fourth intermediate layer 13d.

Examples of the sensing element 50 (for example, the first sensing element 50a) will now be described.

In the following, the description of "material A/material B" refers to the state where a layer of material B is provided on a layer of material A.

FIG. 3A to FIG. 3F are schematic cross-sectional views illustrating the pressure sensor according to the first embodiment.

The drawings illustrate the sensing element 50 (the first sensing element 50a).

Figure 3A:
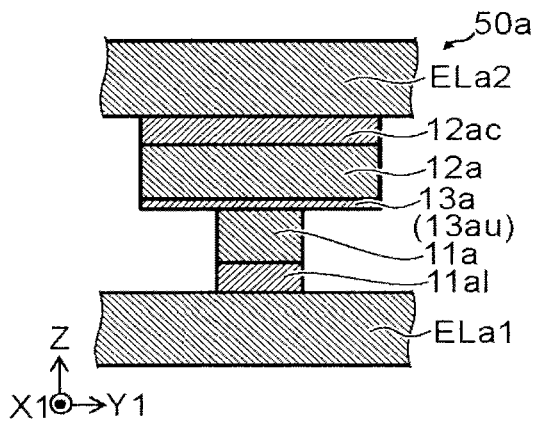
FIG. 3A to FIG. 3F are schematic cross-sectional views showing the pressure sensor according to the first embodiment.

As shown in FIG. 3A, the first sensing element 50a includes a first electrode ELa1 (a lower electrode), an underlayer 11a*l*, the first magnetic layer 11a, the first intermediate layer 13a, the second magnetic layer 12a, a cap layer 12ac, and a second electrode ELa2 (an upper electrode). The first magnetic layer 11a is provided between the first electrode ELa1 and the second electrode ELa2. The second magnetic layer 12a is provided between the first magnetic layer 11a and the second electrode ELa2. The underlayer 11a1 is provided between the first magnetic layer 11a and the first electrode ELa1. The cap layer 12ac is provided between the second magnetic layer 12a and the second electrode ELa2.

Examples of the material used for the layers will now be described using as an example the case where the first magnetic layer 11a and the second magnetic layer 12a are a magnetization free layer.

As the underlayer 11a*l*, Ta/Ru is used, for example. The thickness (the length in the Z-axis direction) of the Ta layer is 3 nm, for example. The thickness of the Ru layer is 2 nm, for example.

As the first magnetic layer 11a, a $Co_{40}Fe_{40}B_{20}$ layer with a thickness of 3 nm is used, for example. As the first intermediate layer 13a, a MgO layer with a thickness of 1.5 nm is used, for example. As the second magnetic layer 12a, a $Co_{40}Fe_{40}B_{20}$ layer with a thickness of 3 nm is used, for example.

As the cap layer 12ac, Ta/Ru is used, for example. The thickness of the Ta layer is 1 nm, for example. The thickness of the Ru layer is 5 nm, for example.

For the first electrode ELa1 and the second electrode ELa2, at least one of aluminum (Al), aluminum-copper alloy (Al—Cu), copper (Cu), silver (Ag), and gold (Au) is used, for example. By using such a material with a relatively small electric resistance as the first electrode ELa1 and the second electrode ELa2, a current can be passed through the first sensing element 50a efficiently. A nonmagnetic material may be used for the first electrode ELa1 and the second electrode ELa2.

The first electrode ELa1 may have a structure including an underlayer (not shown) for the first electrode ELa1, a cap layer (not shown) for the first electrode ELa1, and a layer provided between them and containing at least one of Al, Al—Cu, Cu, Ag, and Au. Tantalum (Ta)/copper (Cu)/tantalum (Ta) or the like is used as the first electrode ELa1, for example. By using Ta as the underlayer for the first electrode ELa1, the adhesion between the film unit 70 and the first electrode ELa1 can be improved, for example. Also titanium (Ti), titanium nitride (TIN), or the like may be used as the underlayer for the first electrode ELa1.

By using Ta as the cap layer for the first electrode ELa1, the oxidation of copper (Cu) or the like under the cap layer can be suppressed. Also titanium (Ti), titanium nitride (TiN), or the like may be used as the cap layer for the first electrode ELa1.

As the underlayer 11al, a stacked structure of a buffer layer (not shown) and a seed layer (not shown) may be used. The buffer layer eases the roughness of the surface of the first electrode ELa1 or the film unit 70, and improves the crystallinity of a layer stacked on the buffer layer, for example. As the buffer layer, at least one selected from the group consisting of tantalum (Ta), titanium (Ti), vanadium (V), tungsten (W), zirconium (Zr), hafnium (Hf), and chromium (Cr) is used, for example. An alloy containing at least one selected from these materials may be used as the buffer layer.

The thickness of the buffer layer is preferably not less than 1 nm and not more than 10 nm. The thickness of the buffer layer is more preferably not less than 1 nm and not more than 5 nm. If the thickness of the buffer layer is too small, the buffer effect will be lost. If the thickness of the buffer layer is too large, the thickness of the sensing element 50 will be too large. The seed layer may be formed on the buffer layer, and may have buffer effect. The buffer layer may be omitted. A Ta layer with a thickness of 3 nm is used as the buffer layer, for example.

The seed layer mentioned above controls the crystal orientation of a layer stacked on the seed layer. The seed layer controls the crystal grain size of a layer stacked on the seed layer. A metal of the fcc structure (face-centered cubic structure), the hcp structure (hexagonal close-packed structure), or the bcc structure (body-centered cubic structure) or the like is used as the seed layer.

As the seed layer, ruthenium (Ru) of the hcp structure, NiFe of the fcc structure, or Cu of the fcc structure is used. Thereby, the crystal orientation of a stacked film (a spin valve film) provided on the seed layer can be made the fcc(111) orientation, for example. A Cu layer with a thickness of 2 nm or a Ru layer with a thickness of 2 nm is used as the seed layer, for example. When it is attempted to enhance the crystal orientation properties of a layer formed on the seed layer, the thickness of the seed layer is preferably not less than 1 nm and not more than 5 nm. The thickness of the seed layer is more preferably not less than 1 nm and not more than 3 nm. Thereby, the function as a seed layer of improving the crystal orientation is exhibited sufficiently. On the other hand, when it is not necessary to provide a crystal orientation to a layer provided on the seed layer (for example, when an amorphous magnetization free layer is formed, etc.), the seed layer may be omitted, for example. A Cu layer with a thickness of 2 nm is used as the seed layer, for example.

For the first magnetic layer 11a, a ferromagnetic material is used. A ferromagnetic material containing at least one element selected from the group consisting of Fe, Co, and Ni may be used for the first magnetic layer 11a, for example. FeCo alloy or NiFe alloy may be used as the material of the first magnetic layer 11a, for example. An alloy containing at least one element selected from the group consisting of Fe, Co, and Ni and boron (B) may be used for the first magnetic layer 11a. Co—Fe—B alloy, Fe—B alloy, Fe—Co—Si—B alloy, or the like may be used for the first magnetic layer 11a, for example. A $Co_{40}Fe_{40}B_{20}$ layer (the thickness being 4 nm, for example) may be used as the first magnetic layer 11a, for example.

For the first magnetic layer 11a, Fe—Ga alloy, Fe—Co—Ga alloy, a Tb-M-Fe alloy (M being at least one selected from the group consisting of Sm, Eu, Gd, Dy, Ho, and Er), a Tb-M1-Fe-M2 alloy (M1 being at least one selected from the group consisting of Sm, Eu, Gd, Dy, Ho, and Er; M2 being at least one selected from the group consisting of Ti, Cr, Mn, Co, Cu, Nb, Mo, W, and Ta), or an Fe-M3-M4-B alloy (M3 being at least one selected from the group consisting of Ti, Cr, Mn, Co, Cu, Nb, Mo, W, and Ta; M4 being at least one selected from the group consisting of Ce, Pr, Nd, Sm, Tb, Dy, and Er) is used. The λs (magnetostriction constant) of these materials is large.

The first magnetic layer 11a may contain at least one of Ni, Fe—Al, and a ferrite ($Fe_3O_4$, $(FeCo)_3O_4$, or the like), for example.

The thickness of the first magnetic layer 11a is 2 nm or more, for example.

The first magnetic layer 11a may have a multi-layer structure. The first magnetic layer 11a may have a two-layer structure, for example. In the case where a tunnel insulating layer of MgO is used as the first intermediate layer 13a, it is preferable that a layer of Co—Fe—B alloy be provided on the interface in contact with the first intermediate layer 13a. Thereby, a high magnetoresistance effect is obtained. In this case, it is preferable that a layer of Co—Fe—B alloy be provided on the side in contact with the first intermediate layer 13a and a layer of the following material be provided on the opposite side to that. For that layer, Fe—Co—Si—B alloy, Fe—Ga alloy, Fe—Co—Ga alloy, a Tb-M-Fe alloy (M being at least one selected from the group consisting of Sm, Eu, Gd, Dy, Ho, and Er), a Tb-M1-Fe-M2 alloy (M1 being at least one selected from the group consisting of Sm, Eu, Gd, Dy, Ho, and Er; M2 being at least one selected from the group consisting of Ti, Cr, Mn, Co, Cu, Nb, Mo, W, and Ta), an Fe-M3-M4-B alloy (M3 being at least one selected from the group consisting of Ti, Cr, Mn, Co, Cu, Nb, Mo, W, and Ta; M4 being at least one selected from the group consisting of Ce, Pr, Nd, Sm, Tb, Dy, and Er), Ni, Fe—Al, or a ferrite ($Fe_3O_4$, $(FeCo)_3O_4$, or the like) is used, for example.

As the first magnetic layer 11a, a stacked film of $Fe_{80}Ga_{20}/Co_{40}Fe_{40}B_{20}$ is used, for example. The thickness of the $Co_{40}Fe_{40}B_{20}$ is 2 nm, for example. The thickness of the $Fe_{80}Ga_{20}$ is 4 nm, for example.

The first intermediate layer 13a cuts the magnetic coupling between the first magnetic layer 11a and the second magnetic layer 12a, for example. A metal, an insulator, or a semiconductor is used for the first intermediate layer 13a, for example. Cu, Au, Ag, or the like is used as the metal, for example.

In the case where a metal is used as the first intermediate layer 13a, the thickness of the first intermediate layer 13a is approximately not less than 1 nm and not more than 7 nm, for example.

As the insulator or the semiconductor used for the first intermediate layer 13a, a magnesium oxide (MgO etc.), an aluminum oxide ($Al_2O_3$ etc.), a titanium oxide (TiO etc.), a zinc oxide (ZnO etc.), gallium oxide (Ga—O), or the like is used, for example.

In the case where an insulator or a semiconductor is used as the first intermediate layer 13a, the thickness of the first intermediate layer 13a is approximately not less than 0.6 nm and not more than 2.5 nm, for example. A CCP (current-confined-path) spacer layer may be used as the first intermediate layer 13a, for example. In the case where a CCP spacer layer is used as the spacer layer, a structure is used in which a copper (Cu) metal path is formed in an insulating layer of aluminum oxide ($Al_2O_3$), for example. A MgO layer with a thickness of 1.5 nm is used as the first intermediate layer 13a, for example.

For the second magnetic layer 12a, a similar ferromagnetic material to the first magnetic layer 11a may be used. A $Co_{40}Fe_{40}B_{20}$ layer (the thickness being 4 nm, for example) may be used as the second magnetic layer 12a, for example. When a multi-layer structure is used as the second magnetic layer 12a, the second magnetic layer 12a may have a two-layer structure, for example. When a tunnel insulating layer of MgO is used as the first intermediate layer 13a, it is preferable that a layer of Co—Fe—B alloy be provided on the interface in contact with the first intermediate layer 13a of the second magnetic layer 12a. A stacked film of $Co_{40}Fe_{40}B_{20}/Fe_{80}Ga_{20}$ is used as the second magnetic layer 12a, for example. The thickness of the $Co_{40}Fe_{40}B_{20}$ is 2 nm, for example. The thickness of the $Fe_{80}Ga_{20}$ is 4 nm, for example.

The material used for the second magnetic layer 12a may be the same material as the first magnetic layer 11a, and each of the first magnetic layer 11a and the second magnetic layer 12a may be a magnetization free layer. This case is preferable because the operation of the change in magnetization with respect to the strain can be made uniform between the first magnetic layer 11a and the second magnetic layer 12a, for example.

The cap layer 12ac protects a layer provided under the cap layer 12ac, for example. A plurality of metal layers are used as the cap layer 12ac, for example. A two-layer structure of a Ta layer and a Ru layer (Ta/Ru) is used as the cap layer 12ac, for example. The thickness of the Ta layer is 1 nm, for example, and the thickness of the Ru layer is 5 nm, for example. Other metal layers may be provided as the cap layer 12ac in place of the Ta layer and the Ru layer. The configuration of the cap layer 12ac is arbitrary. A nonmagnetic material may be used as the cap layer 12ac, for example. Other materials may be used as the cap layer 12ac to the extent that they can protect a layer provided under the cap layer 12ac.

Figure 3B:
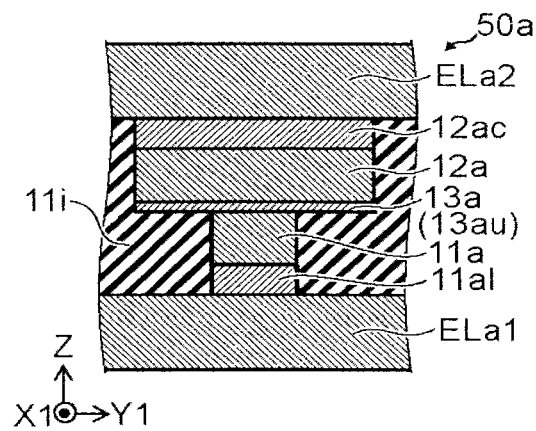

As shown in FIG. 3B, the first sensing element 50a may further include an insulating layer 11i. The insulating layer 11i is provided between the first electrode ELa1 and the second electrode ELa2, for example. The insulating layer 11i surrounds the stacked film including the first magnetic layer 11a, the first intermediate layer 13a, and the second magnetic layer 12a, for example.

For the insulating layer 11i, an aluminum oxide (for example, $Al_2O_3$), a silicon oxide (for example, $SiO_2$), or the like is used, for example. By the insulating layer 11i, leakage current around the stacked film can be suppressed.

Figure 3C:
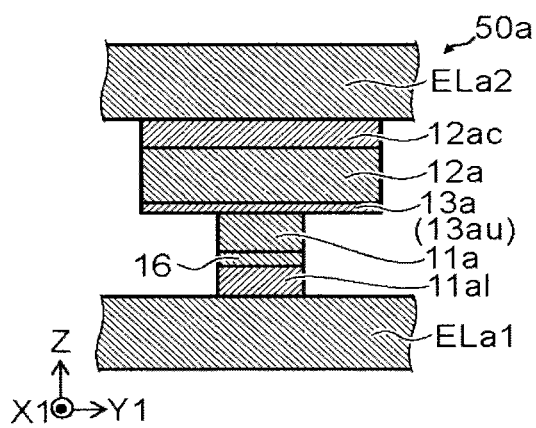

As shown in FIG. 3C, a functional layer 16 may be provided between the first magnetic layer 11a and the underlayer 11al. The first magnetic layer 11a is disposed between the functional layer 16 and the first intermediate unit 13au. An oxide or a nitride is used for the functional layer 16, for example. The functional layer 16 contains an oxide of at least one selected from the group consisting of Mg, Al, Si, Ti, V, Cr, Mn, Fe, Co, Ni, Cu, Zn, Zr, Nb, Mo, Ru, Rh, Pd, Ag, Hf, Ta, W, Sn, Cd, and Ga, for example. The functional layer 16 contains a nitride of at least one selected from the group mentioned above, for example. The functional layer 16 contains an oxide of at least one of Mg, Ti, V, Zn, Sn, Cd, and Ga, for example.

On the other hand, the first magnetic layer 11a has an amorphous structure, and contains boron, for example. By using the first magnetic layer 11a and the functional layer 16 like the above in combination, a high gauge factor is obtained. The gauge factor is the ratio of the amount of magnetoresistance change to the strain, for example. By a high gauge factor, a pressure sensor with a higher sensitivity can be provided.

Figure 3D:
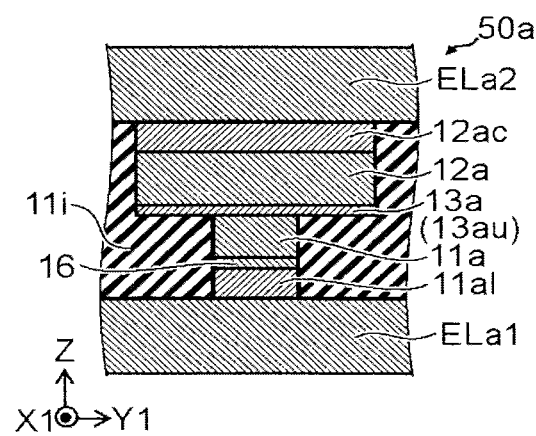

As shown in FIG. 3D, the insulating layer 11i may be provided in the configuration illustrated in FIG. 3C.

Figure 3E:
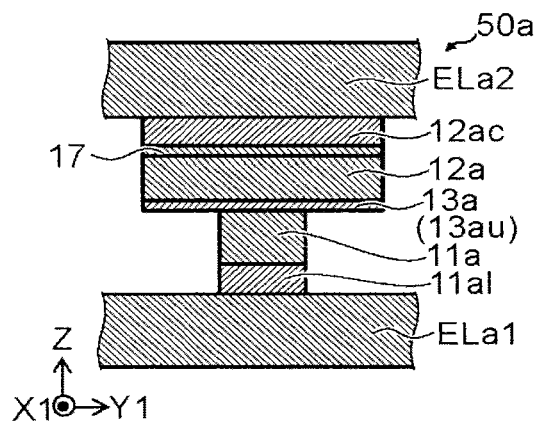

As shown in FIG. 3E, a functional layer 17 may be provided between the second magnetic layer 12a and the cap layer 12ac. The second magnetic layer 12a is disposed between the functional layer 17 and the first intermediate unit 13au. The material described in regard to the functional layer 16 is used for the functional layer 17, for example. At this time, the second magnetic layer 12a has an amorphous structure, and contains boron, for example, By using the second magnetic layer 12a and the functional layer 17 like the above in combination, a high gauge factor is obtained.

Figure 3F:
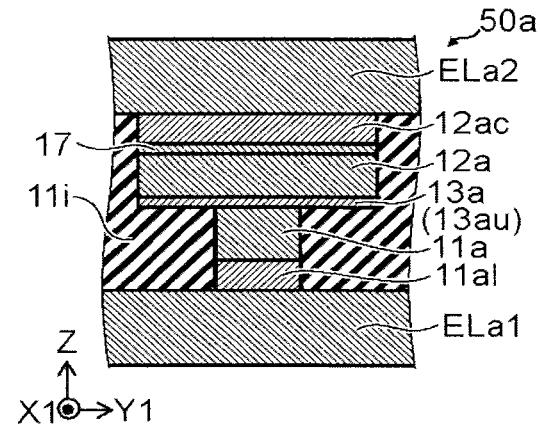

As shown in FIG. 3F, the insulating layer 11i may be provided in the configuration illustrated in FIG. 3E.

In the embodiment, in the first magnetic layer 11a, the first major axis length L1 is longer than the first minor axis length D1, as described above. In the second magnetic layer 12a, the second major axis length L2 is longer than the second minor axis length D2. These magnetic layers have shape magnetic anisotropy. Thus, the magnetization direction of the first magnetic layer 11a is set along the first direction X1 (the direction of the first major axis length L1). The magnetization direction of the second magnetic layer 12a is set along the second direction X2 (the direction of the second major axis length L2).

Thus, by utilizing shape anisotropy, the magnetization direction of the magnetization free layer included in the first sensing element 50a in a state where the external pressure is small (for example, a state where the external pressure is zero) can be set to an arbitrary direction, without using magnetization direction control by a hard bias of CoPt or the like, an exchange coupling bias using IrMn or the like, or others. Thereby, the pressure can be detected with high sensitivity.

On the other hand, in bias control by a hard bias or an exchange coupling bias, it is difficult to direct the initial magnetization directions of a plurality of magnetization free layers included in a plurality of sensing elements 50 to different directions in the X-Y plane.

In the embodiment, by utilizing shape anisotropy, the initial magnetization direction can be easily set to a desired direction in each of the plurality of sensing elements 50 provided on the upper surface 70u of the film unit 70, for example. Thereby, the operation of each of the plurality of sensing elements 50 can be effectively utilized, for example.

In the pressure sensor 110 of the embodiment, when the film unit 70 is bent by a pressure from the outside, a strain is generated in the sensing element 50 (for example, the first sensing element 50a). The sensing element 50 has the function of converting the change in strain to a change in electric resistance.

The operation in which the first sensing element 50a functions as a strain sensor is based on application of "inverse magnetostriction effect" and "magnetoresistance effect." The "inverse magnetostriction effect" is obtained in the ferromagnetic layer used as the first magnetic layer 11a and the second magnetic layer 12a. The "magnetoresistance effect" is exhibited in the stacked film including the first magnetic layer 11a, the first intermediate layer 13a, and the second magnetic layer 12a.

The "inverse magnetostriction effect" is a phenomenon in which the magnetization of a ferromagnetic material is changed by a strain generated in the ferromagnetic material. That is, when a strain is generated in the stacked film of the first sensing element 50a due to a pressure from the outside, the magnetization direction of the magnetization free layer is changed. Consequently, the relative angle between the magnetization of the first magnetic layer 11a and the magnetization of the second magnetic layer 12a is changed. At this time, a change in electric resistance occurs due to the magnetoresistance effect (MR effect)." The MR effect includes GMR (giant magnetoresistance) effect, TMR (tunneling magnetoresistance) effect, or the like, for example. The MR effect is exhibited by passing a current through the stacked film to read the change in relative angle between the directions of the magnetizations as an electric resistance change.

A strain is generated in the first sensing element 50a due to a strain generated in the stacked film, for example. The direction of the magnetization of the magnetization free layer (the first magnetic layer 11a) is changed by the strain. The relative angle between the direction of the magnetization of the first magnetic layer 11a and the direction of the magnetization of the second magnetic layer 12a is changed. The MR effect appears due to the inverse magnetostriction effect.

When the ferromagnetic material used for the magnetization free layer has a positive magnetostriction constant, the direction of the magnetization changes so that the angle between the direction of the magnetization and the direction of a tensile strain becomes smaller and the angle between the direction of the magnetization and the direction of a compressive strain becomes larger. When the ferromagnetic material used for the magnetization free layer has a negative magnetostriction constant, the direction of the magnetization changes so that the angle between the direction of the magnetization and the direction of a tensile strain becomes larger and the angle between the direction of the magnetization and the direction of a compressive strain becomes smaller.

When the combination of the materials of the stacked film of the first magnetic layer 11a, the first intermediate layer 13a, and the second magnetic layer 12a has a positive magnetoresistance effect, the electric resistance decreases as the relative angle between the magnetization of the first magnetic layer 11a and the magnetization of the second magnetic layer 12a decreases. When the combination of the materials of the stacked film of the first magnetic layer 11a, the first intermediate layer 13a, and the second magnetic layer 12a has a negative magnetoresistance effect, the electric resistance increases as the relative angle between the magnetization of the first magnetic layer 11a and the magnetization of the second magnetic layer 12a decreases.

Examples of the change in magnetization will now be described. In the following examples, each of the ferromagnetic materials used for the first magnetic layer 11a and the second magnetic layer 12a has a positive magnetostriction constant, and the stacked film including the first magnetic layer 11a, the first intermediate layer 13a, and the second magnetic layer 12a has a positive magnetoresistance effect. Both the first magnetic layer 11a and the second magnetic layer 12a are a magnetization free layer.

FIG. 4A to FIG. 4D are schematic diagrams illustrating the pressure sensor according to the first embodiment.

Figures 4A, 4B, 4C:
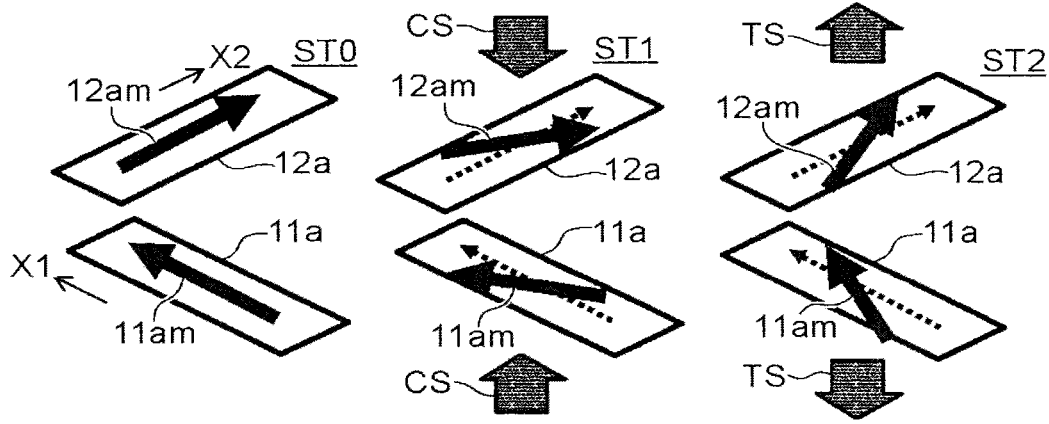
FIG. 4A to FIG. 4D are schematic diagrams showing the pressure sensor according to the first embodiment.

The drawings illustrate operations of the sensing element 50 (the first sensing element 50a). FIG. 4A corresponds to a state where no strain is generated in the first sensing element 50a (a no-strain state ST0). FIG. 4B corresponds to a state where a compressive strain is generated in the first sensing element 50a (a first state ST1). FIG. 4C corresponds to a state where a tensile strain is generated in the first sensing element 50a (a second state ST2). In these drawings, for easier viewing of the drawings, the first magnetic layer 11a and the second magnetic layer 12a are depicted, and the first intermediate unit 13au is omitted.

Figure 4D:
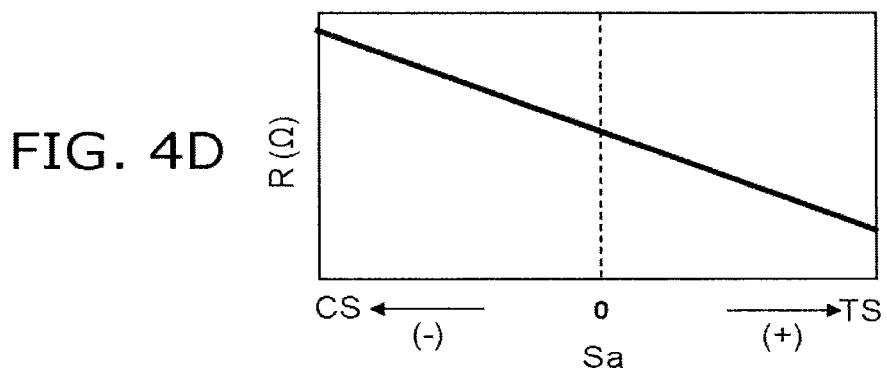

FIG. 4D illustrates the relationship between the strain Sa generated in the first sensing element 50a and the electric resistance R ($\Omega$) of the first sensing element 50a. The electric resistance R is the electric resistance between the first magnetic layer 11a and the second magnetic layer 12a.

As shown in FIG. 4A, in the no-strain state ST0, the magnetization 11am of the first magnetic layer 11a is set along the first direction X1 in which the first magnetic layer 11a extends. In the no-strain state ST0, the magnetization 12am of the second magnetic layer 12a is set along the second direction X2 in which the second magnetic layer 12a extends. These are due to the shape magnetic anisotropy mentioned above.

By changing the angle between the first direction X1 in which the first magnetic layer 11a extends and the second direction X2 in which the second magnetic layer 12a extends, the relative angle between the direction of the magnetization 11am of the first magnetic layer 11a and the direction of the magnetization 12am of the second magnetic layer 12a can be set arbitrarily.

As shown in FIG. 4B, in the first state ST1 in which a compressive strain CS is generated, the angle between the magnetization 11am of the first magnetic layer 11a and the magnetization 12am of the second magnetic layer 12a is larger than the angle in the no-strain state ST0, for example. The electric resistance R changes in conjunction with this.

As shown in FIG. 4C, in the second state ST2 in which a tensile strain TS is generated, the angle between the magnetization 11am of the first magnetic layer 11a and the magnetization 12am of the second magnetic layer 12a is smaller than the angle in the no-strain state ST0, for example. The electric resistance R changes in conjunction with this.

As shown in FIG. 4D, when a compressive strain CS is generated, the electric resistance R of the first sensing element 50a increased as compared to the no-strain state ST0. When a tensile strain TS is generated, the electric resistance R of the first sensing element 50a decreased as compared to the no-strain state ST0.

In this way, the first sensing element 50a can convert the change in strain Sa generated in the first sensing element 50a to a change in electric change R.

As illustrated in FIG. 4A, in the first sensing element 50a, in the no-strain state ST0, the magnetization of the first magnetic layer 11a and the magnetization of the second magnetic layer 12a can be directed to directions different from each other. Thereby, as illustrated in FIG. 4D, the electric resistance R changes linearly with respect to the tensile and compressive strain Sa, for example. Thereby, a high-sensitivity pressure sensor can be provided.

Figure 5:
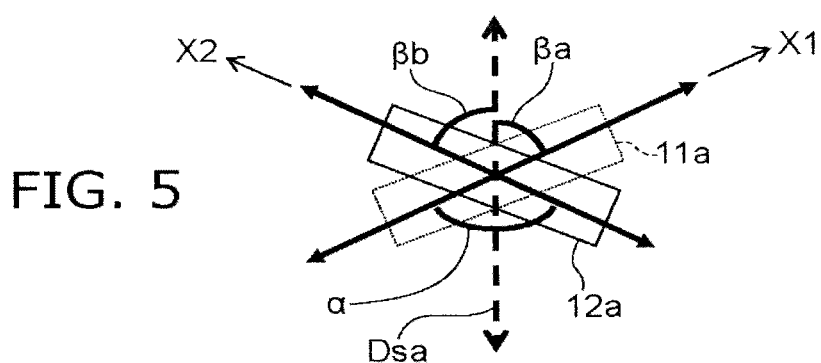
FIG. 5 is a schematic plan view showing the pressure sensor according to the first embodiment.

FIG. 5 is a schematic plan view illustrating the pressure sensor according to the first embodiment.

As shown in FIG. 5, in the embodiment, the angle $\alpha$ between the extending direction of the first magnetic layer 11a (the first direction X1) and the extending direction of the second magnetic layer 12a (the second direction X2) is larger than 0 degrees and smaller than 180 degrees. That is, the first direction X1 crosses the second direction X2. Thereby, the magnetizations of the first magnetic layer 11a and the second magnetic layer 12a in the no-strain state ST0 are directed to directions different from each other, for example.

The angle $\beta a$ between the extending direction of the first magnetic layer 11a (the first direction X1) and the strain direction Dsa is arbitrary. The angle $\beta b$ between the extending direction of the second magnetic layer 12a (the second direction X2) and the strain direction Dsa is arbitrary.

In the case where the absolute value of the angle βb is equal to the absolute value of the angle βa, the extending direction of the first magnetic layer 11a and the extending direction of the second magnetic layer 12a are line-symmetric with respect to the strain direction Dsa. At this time, the magnetization 11am of the first magnetic layer 11a and the magnetization 12am of the second magnetic layer 12a can be simultaneously changed with respect to the strain Sa. Thereby, the strain Sa can be detected with higher sensitivity. The difference between the absolute value of the angle βa and the absolute value of the angle βb is 5 degrees or less, for example.

FIG. 6A to FIG. 6D are schematic plan views illustrating the pressure sensor according to the first embodiment.

The drawings show examples of the magnetization direction in the no-strain state ST0. The drawings show examples regarding the first magnetic layer 11a.

The direction of the initial magnetization 11am of the first magnetic layer 11a of the first sensing element 50a can be set by the direction in which the external magnetic field is applied, for example.

Figure 6A:
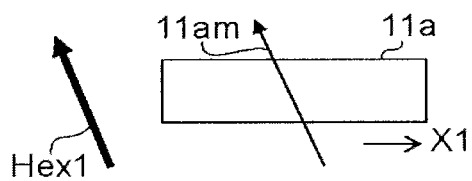
FIG. 6A to FIG. 6D are schematic plan views showing the pressure sensor according to the first embodiment.
Figure 6B:
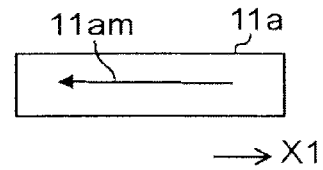

FIG. 6A illustrates a state where an external magnetic field Hex1 is applied. FIG. 6B illustrates a state where the external magnetic field Hex1 is removed. As shown in FIG. 6A, the external magnetic field Hex1 crosses the first direction X1. When the external magnetic field Hex1 is being applied, the direction of the magnetization 11am of the first magnetic layer 11a is set along the direction of the external magnetic field Hex1.

As shown in FIG. 6B, when the external magnetic field Hex1 is removed, the direction of the magnetization 11am of the first magnetic layer 11a is set along the first direction X1 due to the shape anisotropy. The direction of the magnetization 11am in FIG. 6B reflects the direction of the external magnetic field Hex1.

Figure 6C:
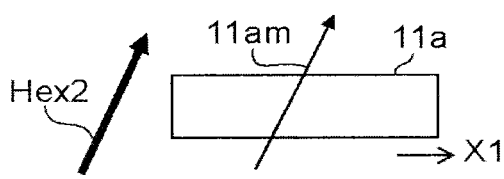
Figure 6D:
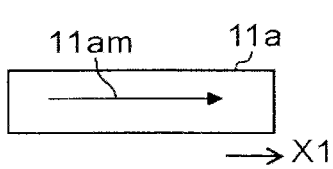

FIG. 6C illustrates a state where an external magnetic field Hex2 is applied. FIG. 6D illustrates a state where the external magnetic field Hex2 is removed. As shown in FIG. 6C, the external magnetic field Hex2 crosses the first direction X1. The direction of the angle from the first direction X1 to the external magnetic field Hex2 is opposite to the direction of the angle from the first direction X1 to the external magnetic field Hex1. When the external magnetic field Hex2 is being applied, the direction of the magnetization 11am of the first magnetic layer 11a is set along the direction of the external magnetic field Hex2.

As shown in FIG. 6D, when the external magnetic field Hex2 is removed, the direction of the magnetization 11am of the first magnetic layer 11a is set along the first direction X1 due to the shape anisotropy. The direction of the magnetization 11am in FIG. 6D reflects the direction of the external magnetic field Hex2. That is, the direction of the magnetization 11am in FIG. 6D is opposite to the direction of the magnetization 11am in FIG. 6B.

Thus, the direction of the magnetization 11am when the external magnetic field is removed depends on the direction of the external magnetic field. The direction of the magnetization 11am when the external magnetic field is removed is directed to the direction of the magnetization 11am projected onto the first direction X1 when the external magnetic field is being applied.

The direction of the magnetization 12am of the second magnetic layer 12a may be similarly controlled by an external magnetic field, for example.

FIG. 7A to FIG. 7F are schematic plan views illustrating the pressure sensor according to the first embodiment.

The drawings show examples of the magnetization direction in the no-strain state ST0.

Figure 7A:
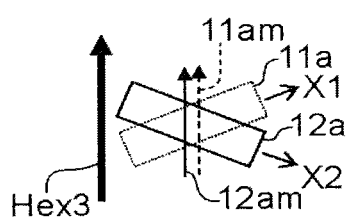
FIG. 7A to FIG. 7F are schematic plan views showing the pressure sensor according to the first embodiment.
Figure 7B:
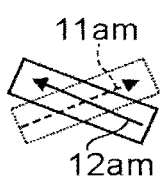

FIG. 7A illustrates a state where an external magnetic field Hex3 is applied. FIG. 7B illustrates a state where the external magnetic field Hex3 is removed. In these examples, the absolute value of the angle between the first direction X1 and the second direction X2 is 45 degrees, for example. As show in FIG. 7A, the external magnetic field Hex3 crosses the first direction X1 and the second direction X2. The external magnetic field Hex3 is perpendicular to the average direction of the first direction X1 and the second direction X2. As shown in FIG. 7B, when the external magnetic field Hex3 is removed, the angle between the direction of the magnetization 11am of the first magnetic layer 11a and the direction of the magnetization 12am of the second magnetic layer 12a is 135 degrees, for example.

Figure 7C:
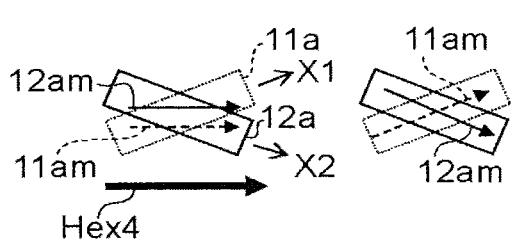
Figure 7D:
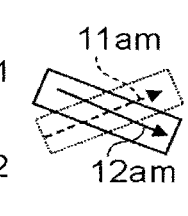

FIG. 7C illustrates a state where an external magnetic field Hex4 is applied. FIG. 7D illustrates a state where the external magnetic filed Hex4 is removed. In these examples, the absolute value of the angle between the first direction X1 and the second direction X2 is 45 degrees, for example. As shown in FIG. 7C, the external magnetic field Hex4 crosses the first direction X1 and the second direction X2. The external magnetic field Hex4 is parallel to the average direction of the first direction X1 and the second direction X2. As shown in FIG. 7D, when the external magnetic filed Hex4 is removed, the angle between the direction of the magnetization 11am of the first magnetic layer 11a and the direction of the magnetization 12am of the second magnetic layer 12a is 45 degrees, for example.

Figure 7E:
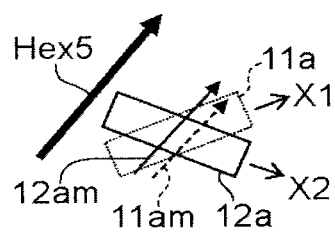
Figure 7F:
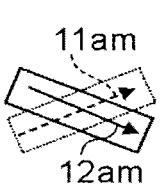

FIG. 7E illustrates a state where an external magnetic field Hex5 is applied. FIG. 7F illustrates a state where the external magnetic filed Hex5 is removed. In these examples, the absolute value of the angle between the first direction X1 and the second direction X2 is 45 degrees, for example. As shown in FIG. 7E, the external magnetic field Hex5 crosses the first direction X1 and the second direction X2. The angle between the external magnetic field Hex5 and the average angle of the first direction X1 and the second direction X2 is less than 90 degrees. As shown in FIG. 7F, when the external magnetic field Hex5 is removed, the angle between the direction of the magnetization 11am of the first magnetic layer 11a and the direction of the magnetization 12am of the second magnetic layer 12a is 45 degrees, for example.

Thus, the relative relationship between the magnetization direction of the first magnetic layer 11a and the magnetization direction of the second magnetic layer 12a can be variously set by the direction of external magnetic field application.

In the case where the first magnetic layer 11a and the second magnetic layer 12a have magnetic properties different from each other, the magnetization directions thereof can be arbitrarily set by two magnetization applications, for example.

Figure 8:
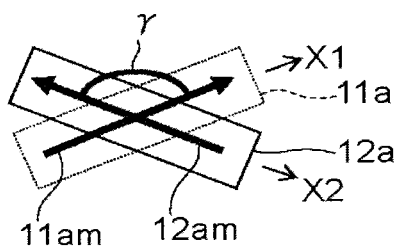
FIG. 8 is a schematic plan view showing the pressure sensor according to the first embodiment.

FIG. 8 is a schematic plan view illustrating the pressure sensor according to the first embodiment.

As shown in FIG. 8, the magnetization 11am of the first magnetic layer 11a and the magnetization 12am of the second magnetic layer 12a are set by the external magnetic field and the direction of shape anisotropy mentioned above.

The angle γ between the magnetization 11am of the first magnetic layer 11a and the magnetization 12am of the second magnetic layer 12a may be set based on the use of the pressure sensor 110.

The angle γ is set to approximately 90 degrees, for example. The angle γ between the magnetization 11am of the first magnetic layer 11a and the magnetization 12am of the second magnetic layer 12a is not less than 60 degrees and not more than 120 degrees, for example. The angle α between the first direction X1 and the second direction is not less than 60 degrees and not more than 120 degrees, for example. At this time, the dynamic range of the change in electric resistance R with respect to the tensile and compressive strain is increased, for example.

The angle γ is set larger than 0 degrees and smaller than 90 degrees, for example. The angle α between the first direction X1 and the second direction X2 is larger than 0 degrees and smaller than 90 degrees, for example. At this time, the element resistance can be reduced, for example. At this time, noise such as shot noise and spin torque noise in the pressure sensor 110 can be reduced, for example.

The angle γ is set larger than 90 degrees and smaller than 180 degrees, for example. The angle between the first direction X1 and the second direction X2 is larger than 90 degrees and smaller than 180 degrees, for example. At this time, the change in electric resistance R with respect to the strain can be increased, for example. In the case where a tunneling magnetoresistance effect using an insulator for the first intermediate layer 13a is used, the magnetoresistance effect with respect to the change in relative angle of magnetization is large when the angle γ is in a range of larger than 90 degrees and smaller than 180 degrees, for example. By setting in this range, the change in electric resistance R with respect to the change in relative angle of magnetization is increased, for example. Thereby, high sensitivity is obtained.

Figure 9A:
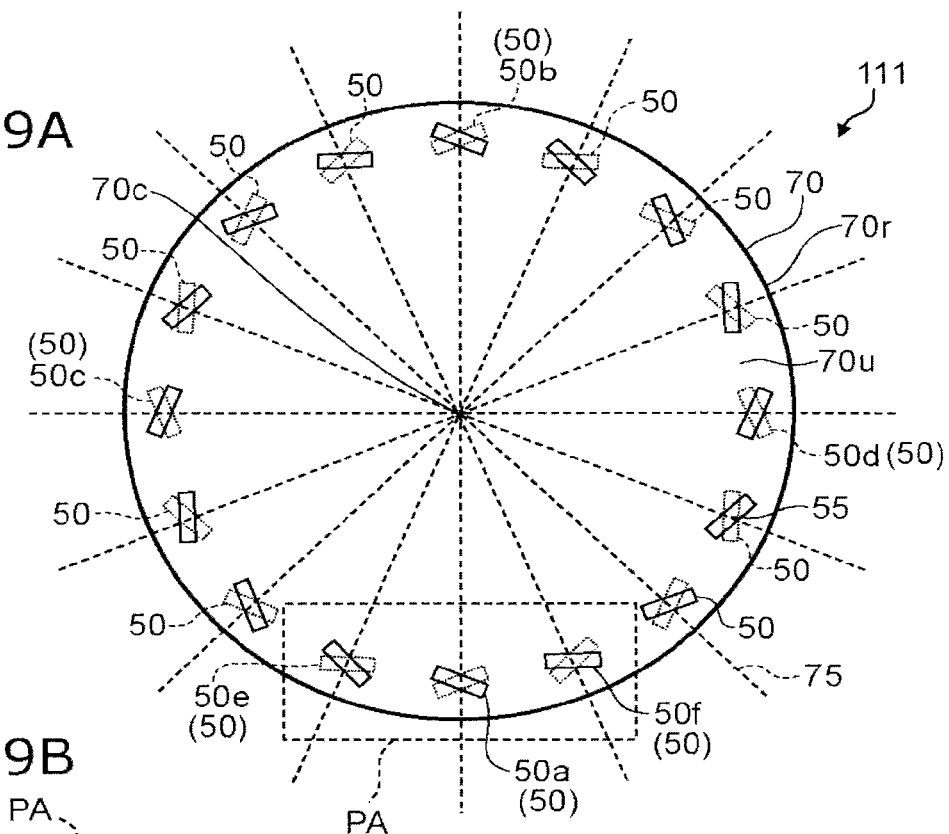
FIG. 9A and FIG. 9B are schematic plan views showing a pressure sensor according to the first embodiment.
Figure 9B:
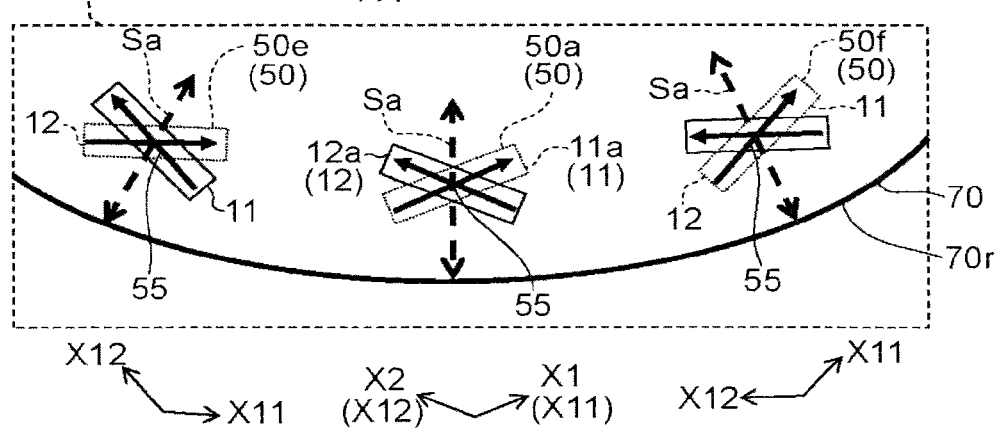

FIG. 9A and FIG. 9B are schematic plan views illustrating a pressure sensor according to the first embodiment.

FIG. 9B shows an enlarged view of a part PA shown in FIG. 9A.

The drawings show examples of the arrangement of sensing elements 50 on the upper surface 70u of the film unit 70.

As shown in FIG. 9A, in a pressure sensor 111 according to the embodiment, the shape of the upper surface 70u of the film unit 70 is a circle. The outer edge 70r of the film unit 70 is in a circular shape.

A plurality of sensing elements 50 are arranged along the outer edge 70r of the film unit 70. In each of the plurality of sensing elements 50, the extending direction X11 of the magnetization free layer 11 crosses the extending direction X12 of the reference layer 12. The magnetization free layer 11 is the first magnetic layer 11a, the third magnetic layer 11b, the fifth magnetic layer 11c, the seventh magnetic layer 11d, and the like, for example. The reference layer 12 is the second magnetic layer 12a, the fourth magnetic layer 12b, the sixth magnetic layer 12c, the eighth magnetic layer 12d, and the like, for example. Here, magnetization may be variable in the reference layer 12. The extending direction X11 of the magnetization free layer 11 is the first direction X1, the third direction X3, the fifth direction X5, the seventh direction X7, and the like, for example. The extending direction X12 of the reference layer 12 is the second direction X2, the fourth direction X2, the sixth direction X6, the eighth direction X8, and the like, for example.

A plurality of sensing elements 50 are arranged so as to overlap a plurality of radial lines 75 passing through the centroid 70c of the film unit 70, for example. In this example, the combination of the magnetization free layer 11 and the reference layer 12 is line-symmetric with respect to each of the radial lines 75.

As shown in FIG. 9B, the first sensing element 50a is disposed between two sensing elements 50 (a sensing element 50e and a sensing element 50f), for example. The magnetization free layer 11 and the reference layer 12 are provided in each of the sensing element 50e and the sensing element 50f.

In each of the plurality of sensing elements 50, a strain Sa is generated along the direction of the radial line 75 passing through the centroid 70c of the film unit 70. In this example, the extending direction X11 of the magnetization free layer 11 and the extending direction X12 of the reference layer 12 are arranged line-symmetrically with respect to the radial line 75. The angle between the direction of the initial magnetization of the magnetization free layer 11 and the direction of the strain Sa is substantially equal to the angle between the direction of the initial magnetization of the reference layer 12 and the direction of the strain Sa. Thereby, the magnetization of the magnetization free layer 11 and the magnetization of the reference layer 12 when a strain Sa is generated can be simultaneously changed. Thereby, a large change in electric resistance R is obtained.

In this example, the angle between the extending direction X11 of the magnetization free layer 11 and the radial line 75 is equal between sensing elements 50. The difference between sensing elements 50 in the absolute value of the angle between the extending direction X11 of the magnetization free layer 11 and the radial line 75 is 5 degrees or less, for example. In this example, the angle between the extending direction of the reference layer 12 and the radial line 75 is equal between sensing elements 50. The difference between sensing elements 50 in the absolute value of the angle between the extending direction of the reference layer 12 and the radial line 75 is 5 degrees or less, for example. By equalizing these angles, the angle between the extending direction X11 of the magnetization free layer 11 and the direction of the strain Sa can be equalized. The angle between the extending direction X12 of the reference layer 12 and the direction of the strain Sa can be equalized. Thus, the change in electric resistance R is substantially equal between sensing elements 50 arranged on the film unit 70. In the case where a substantially equal change in electric resistance R with respect to the pressure is obtained in a plurality of sensing elements 50, the plurality of sensing elements 50 may be connected together at least one of in series and in parallel as described later; thereby, the S/N ratio can be increased, for example.

In this example, the distances between the centroid 70c of the film unit 70 and the centroids 55 of the plurality of sensing elements 50 are equal to one another. Thereby, the magnitudes of the strains Sa generated in the plurality of sensing elements 50 are substantially equal, for example. The centroid 55 of the sensing element 50 is the centroid of the region where the magnetization free layer 11 (for example, the first magnetic layer 11a) and the reference layer 12 (for example, the second magnetic layer 12a) overlap when the magnetization free layer 11 and the reference layer 12 are projected onto the X-Y plane. The centroid 55 corresponds to the centroid of the region where the magnetization free layer 11 and the reference layer 12 overlap in the X-Y plane.

Figure 10A:
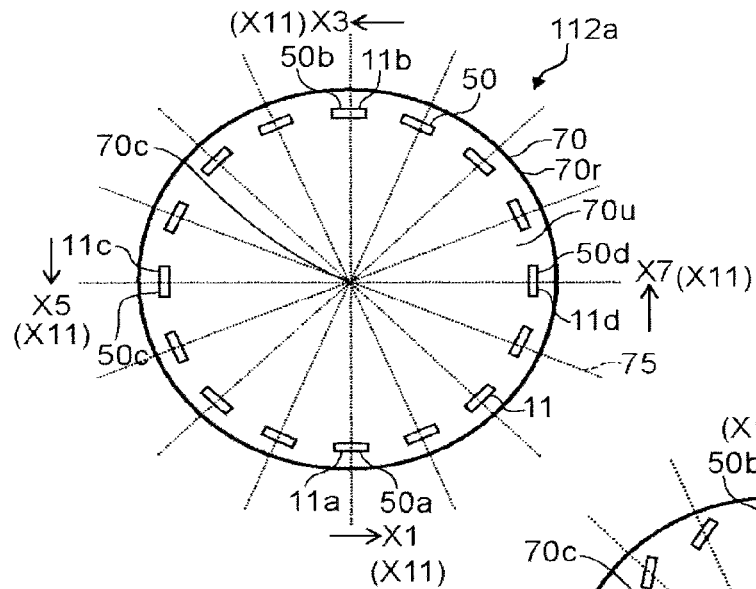
FIG. 10A to FIG. 10C are schematic plan views showing pressure sensors according to the first embodiment.
Figure 10B:
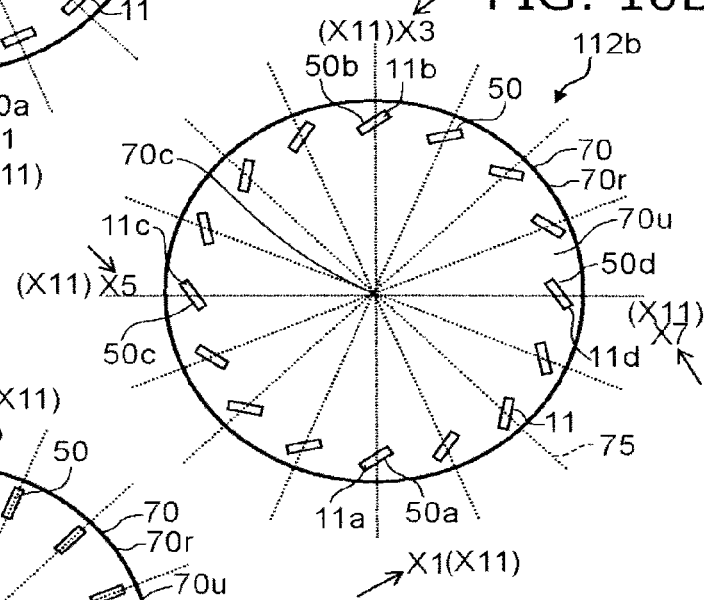
Figure 10C:
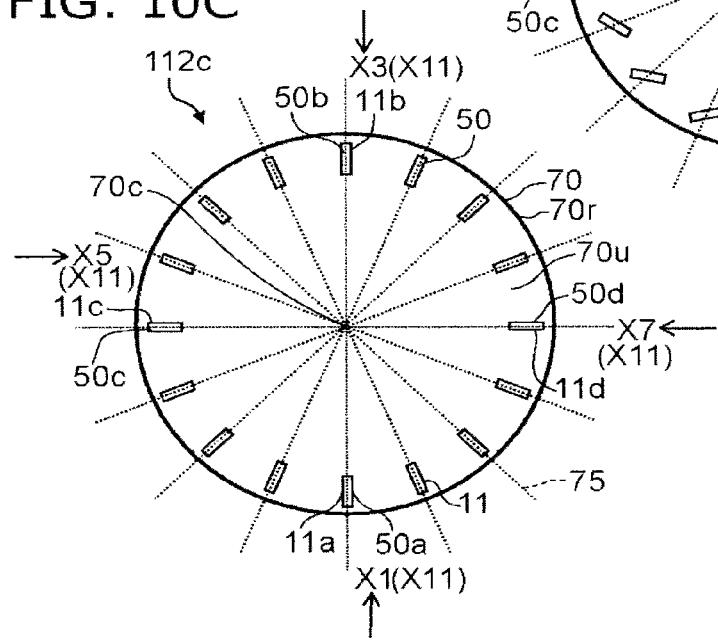

FIG. 10A to FIG. 10C are schematic plan views illustrating pressure sensors according to the first embodiment.

The drawings show examples of the arrangement of magnetization free layers 11.

As shown in FIG. 10A, in a pressure sensor 112a according to the embodiment, the extending direction X11 of the magnetization free layer 11 of each of the plurality of sensing elements 50 is orthogonal to the radial line 75 passing through the centroid 70c of the circular film unit 70.

As shown in FIG. 10B, in a pressure sensor 112b according to the embodiment, the extending direction X11 of the magnetization free layer 11 of each of the plurality of sensing elements 50 is inclined with respect to the radial line 75 passing through the centroid 70c of the circular film unit 70.

As shown in FIG. 10C, in a pressure sensor 112c according to the embodiment, the extending direction X11 of the magnetization free layer 11 of each of the plurality of sensing elements 50 is parallel to the radial line 75 passing through the centroid 70c of the circular film unit 70.

In these examples, the reference layer 12 is omitted. The extending direction X12 of the reference layer 12 is set so as to cross the extending direction X12 of the magnetization free layer 11.

In the pressure sensors 112a and 112c, the magnetization direction of the magnetization free layer 11 changes when the direction of the external pressure is a prescribed direction. The magnetization direction of the magnetization free layer 11 changes when the direction of the external pressure is a prescribed polarity.

On the other hand, in the pressure sensor 112b, the magnetization direction changes under an external pressure in an arbitrary direction (plus or minus) in accordance with the polarity. Therefore, the external pressure can be sensed independently of the polarity of the external pressure.

The dynamic range in the polarity of a prescribed pressure in the pressure sensors 112a and 112c is wider than the dynamic range in the polarity of the prescribed pressure in the pressure sensor 112b. The arrangement of sensing elements 50 (for example, the extending directions X11 of magnetization free layers 11) may be set in accordance with the use.

Figure 11:
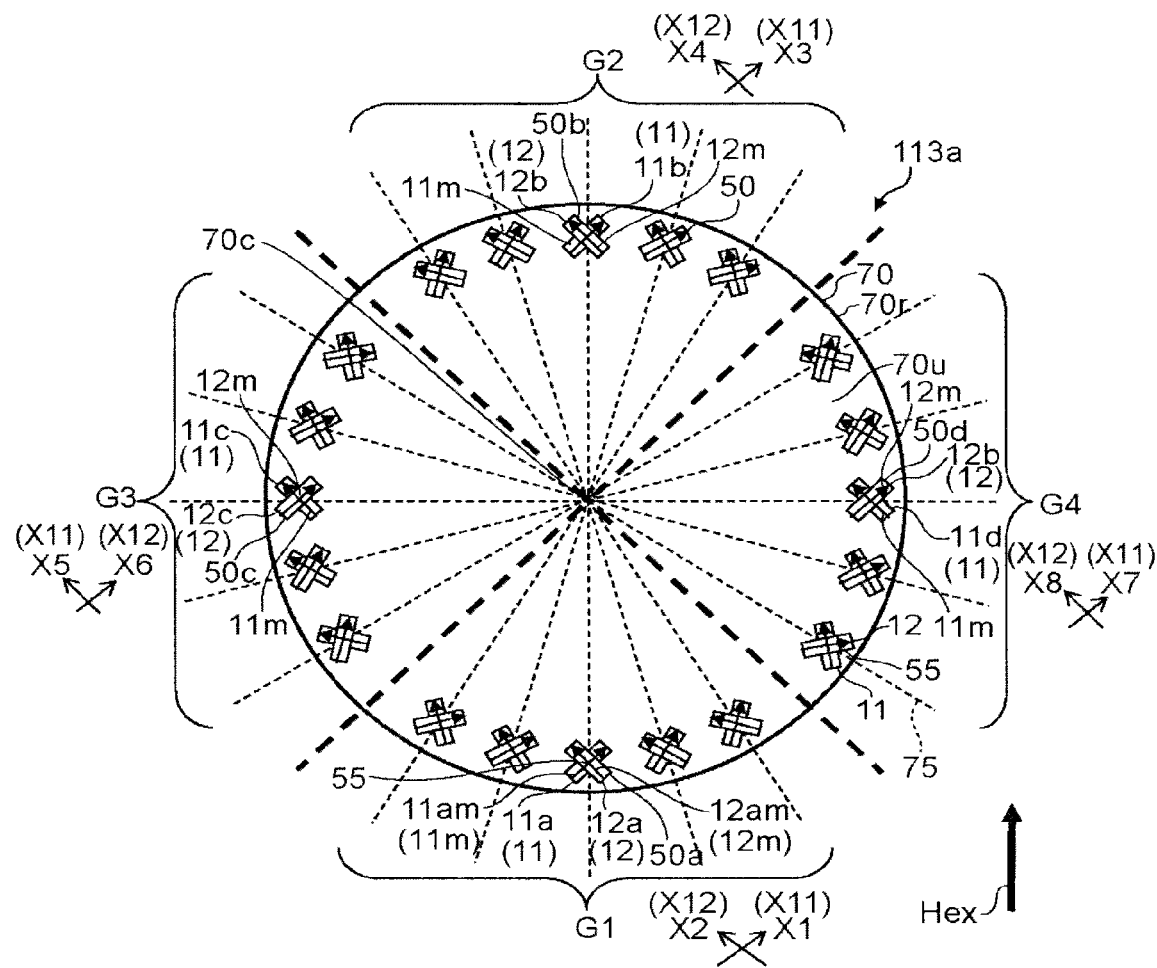
FIG. 11 is a schematic plan view showing a pressure sensor according to the first embodiment.

FIG. 11 is a schematic plan view illustrating a pressure sensor according to the first embodiment.

As shown in FIG. 11, in a pressure sensor 113a according to the embodiment, the angle α between the extending direction X11 (for example, the first direction X1 or the like) of the magnetization free layer 11 (for example, the first magnetic layer 11a or the like) and the extending direction X12 (for example, the second direction X2 or the like) of the reference layer 12 (for example, the second magnetic layer 12a or the like) is 90 degrees in each of the plurality of sensing elements 50.

The absolute value of a first angle β1 between the radial line 75 passing through the centroid 55 of each of the plurality of sensing elements 50 and the centroid 70c of the film unit 70 and the extending direction X11 of the magnetization free layer 11 of the sensing element 50 is 45 degrees. The absolute value of the first angle β1 may be not less than 30 degrees and not more than 60 degrees. In this example, these angles are 45 degrees.

The absolute value of a second angle β2 between the radial line 75 passing through the centroid 55 of each of the plurality of sensing elements 50 and the centroid 70c of the film unit 70 and the extending direction X12 of the reference layer 12 of the sensing element 50 is 45 degrees. The absolute value of the second angle β2 may be not less than 30 degrees and not more than 60 degrees. In this example, these angles are 45 degrees.

By setting the absolute value of the first angle β1 and the absolute value of the second angle β2 not less than 30 degrees and not more than 60 degrees, the dynamic range of the electric resistance change with respect to the positive and negative pressure can be widened, for example.

The magnetization direction in each sensing element 50 is set by applying an external magnetic field Hex and removing the external magnetic field Hex, for example.

In the pressure sensor 113a, the plurality of sensing elements 50 are separated into a plurality of groups (a first to a fourth group G1 to G4).

In the first group G1, the angle from the direction from the centroid 70c of the film unit 70 toward the centroid 55 of a sensing element 50 (a direction parallel to the radial line 75) to the magnetization direction 11m of the magnetization free layer 11 of the sensing element 50 (for example, the direction of the magnetization 11am) is +135 degrees, for example. On the other hand, the angle from the direction from the centroid 55 of the sensing element 50 toward the centroid 70c of the film unit 70 (a direction parallel to the radial line 75) to the magnetization direction 12m of the reference layer 12 of the sensing element 50 is −135 degrees.

In the third group G3, the angle from the direction from the centroid 70c of the film unit 70 toward the centroid 55 of a sensing element 50 (a direction parallel to the radial line 75) to the magnetization direction 11m of the magnetization free layer 11 of the sensing element 50 (for example, the direction of the magnetization 11am) is +45 degrees, for example. On the other hand, the angle from the direction from the centroid 70c of the film unit 70 toward the centroid 55 of the sensing element 50 (a direction parallel to the radial line 75) to the magnetization direction 12m of the reference layer 12 of the sensing element 50 is +135 degrees.

In the second group G2, the angle from the direction from the centroid 70c of the film unit 70 toward the centroid 55 of a sensing element 50 (a direction parallel to the radial line 75) to the magnetization direction 11m of the magnetization free layer 11 of the sensing element 50 (for example, the direction of the magnetization 11am) is +45 degrees, for example. On the other hand, the angle from the direction from the centroid 55 of the sensing element 50 toward the centroid 70c of the film unit 70 (a direction parallel to the radial line 75) to the magnetization direction 12m of the reference layer 12 of the sensing element 50 is −45 degrees.

In the fourth group G4, the angle from the direction from the centroid 70c of the film unit 70 toward the centroid 55 of a sensing element 50 (a direction parallel to the radial line 75) to the magnetization direction 11m of the magnetization free layer 11 of the sensing element 50 (for example, the direction of the magnetization 11am) is −135 degrees, for example. On the other hand, the angle from the direction from the centroid 70c of the film unit 70 toward the centroid 55 of the sensing element 50 (a direction parallel to the radial line 75) to the magnetization direction 12m of the reference layer 12 of the sensing element 50 is −45 degrees.

Thus, the relationship between the magnetization direction 11m of the magnetization free layer 11 and the radial line 75 and the relationship between the magnetization direction 12m of the reference layer 12 and the radial line 75 are different between groups.

In the circular film unit 70, the direction of strain Sa is set along the radial line 75. The polarity of the properties obtained in the sensing element 50 included in the first group G1 is the same as the polarity of the properties obtained in the sensing element 50 included in the second group G2. The polarity of the properties obtained in the sensing element 50 included in the third group G3 is the same as the polarity of the properties obtained in the sensing element 50 included in the fourth group G4. The polarity of the properties obtained in the sensing element 50 included in the first group G1 is opposite to the polarity of the properties obtained in the sensing element 50 included in the third group G3.

In the case where the angle α between the extending direction X11 of the magnetization free layer 11 and the extending direction X12 of the reference layer 12 is 90 degrees, the electric resistance R when the strain Sa is zero is equal between sensing elements 50.

The properties obtained in the sensing element 50 of the first group G1 and the second group G2 are strain sensor properties opposite to the properties obtained in the sensing element 50 of the third group G3 and the fourth group G4, with respect to the tensile and compressive strain Sa.

By forming a bridge circuit using a plurality of sensing elements 50 with polarities opposite to one another, the output is increased as described later, for example. The function of temperature compensation is obtained, for example.

In the embodiment, the straight line passing through the centroid of the upper surface 70u of the film unit 70 (the centroid 70c) and the centroid of the region where the first magnetic layer 11a and the second magnetic layer 12a overlap is defined as a first straight line. The angle between the first straight line and the first direction X1 is defined as a first angle. The straight line passing through the centroid of the upper surface 70u (the centroid 70c) and the centroid of the region where the third magnetic layer 11b and the fourth magnetic layer 12ba overlap is defined as a third straight line. The angle between the third straight line and the third direction X3 is defined as a fifth angle. The difference between the absolute value of the first angle and the absolute value of the fifth angle is 5 degrees or less, for example.

In this example, the extending direction of the magnetization free layer 11 of the first sensing element 50a is substantially parallel to the extending direction of the magnetization free layer 11 of the second sensing element 50b. The absolute value of the angle between the extending direction of the first magnetic layer 11a (the first direction X1) and the extending direction of the second magnetic layer 11b (the third direction X3) is 5 degrees or less, for example. The absolute value of the angle between the extending direction of the fifth magnetic layer 11c (the fifth direction X5) and the extending direction of the seventh magnetic layer 11d (the seventh direction X7) is 5 degrees or less, for example.

Figure 12:
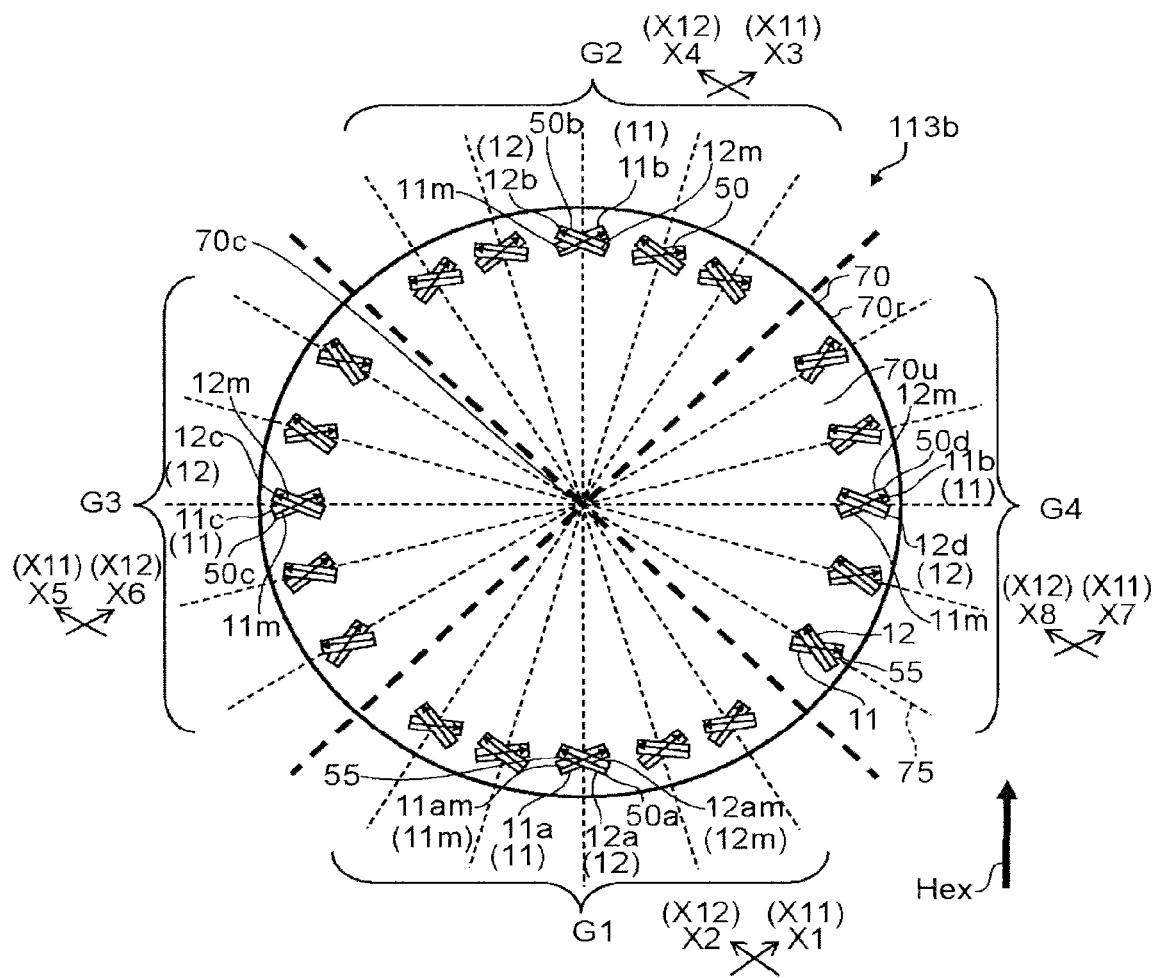
FIG. 12 is a schematic plan view showing a pressure sensor according to the first embodiment.

FIG. 12 is a schematic plan view illustrating a pressure sensor according to the first embodiment.

As shown in FIG. 12, in a pressure sensor 113b according to the embodiment, in each of the plurality of sensing elements 50, the angle α between the extending direction X11 (for example, the first direction X1 or the like) of the magnetization free layer 11 (for example, the first magnetic layer 11a or the like) and the extending direction X12 (for example, the second direction X2 or the like) of the reference layer 12 (for example, the second magnetic layer 12a or the like) is 135 degrees. The absolute value of this angle is 45 degrees, for example.

In the first group G1 and the second group G2, the absolute value of the first angle β1 between the radial line 75 passing through the centroid 55 of each of the plurality of sensing elements 50 and the centroid 70c of the film unit 70 and the extending direction X11 of the magnetization free layer 11 of the sensing element 50 is 67.5 degrees.

In the first group G1 and the second group G2, the absolute value of the second angle β2 between the radial line 75 passing through the centroid 55 of each of the plurality of sensing elements 50 and the centroid 70c of the film unit 70 and the extending direction X12 of the reference layer 12 of the sensing element 50 is 67.5 degrees.

In the third group G3 and the fourth group G4, the absolute value of the first angle β1 between the radial line 75 passing through the centroid 55 of each of the plurality of sensing elements 50 and the centroid 70e of the film unit 70 and the extending direction X11 of the magnetization free layer 11 of the sensing element 50 is 22.5 degrees.

In the third group G3 and the fourth group G4, the absolute value of the second angle β2 between the radial line 75 passing through the centroid 55 of each of the plurality of sensing elements 50 and the centroid 70c of the film unit 70 and the extending direction X12 of the reference layer 12 of the sensing element 50 is 22.5 degrees.

Thus, the first angle β1 and the second angle β2 may be different between sensing elements 50.

The magnetization direction in each sensing element 50 is set by applying an external magnetic field Hex and removing the external magnetic field Hex, for example.

In the first group G1, the angle from the direction from the centroid 70c of the film unit 70 toward the centroid 55 of a sensing element 50 (a direction parallel to the radial line 75) to the magnetization direction 11m of the magnetization free layer 11 of the sensing element 50 (for example, the direction of the magnetization 11am) is +112.5 degrees, for example. On the other hand, the angle from the direction from the centroid 55 of the sensing element 50 toward the centroid 70c of the film unit 70 (a direction parallel to the radial line 75) to the magnetization direction 12m of the reference layer 12 of the sensing element 50 is −112.5 degrees.

In the third group G3, the angle from the direction from the centroid 70c of the film unit 70 toward the centroid 55 of a sensing element 50 (a direction parallel to the radial line 75) to the magnetization direction 11m of the magnetization free layer 11 of the sensing element 50 (for example, the direction of the magnetization 11am) is +157.5 degrees, for example. On the other hand, the angle from the direction from the centroid 70c of the film unit 70 toward the centroid 55 of the sensing element 50 (a direction parallel to the radial line 75) to the magnetization direction 12m of the reference layer 12 of the sensing element 50 is +22.5 degrees.

In the second group G2, the angle from the direction from the centroid 70c of the film unit 70 toward the centroid 55 of a sensing element 50 (a direction parallel to the radial line 75) to the magnetization direction 11m of the magnetization free layer 11 of the sensing element 50 (for example, the direction of the magnetization 11am) is +67.5 degrees, for example. On the other hand, the angle from the direction from the centroid 55 of the sensing element 50 toward the centroid 70c of the film unit 70 (a direction parallel to the radial line 75) to the magnetization direction 12m of the reference layer 12 of the sensing element 50 is −67.5 degrees.

In the fourth group G4, the angle from the direction from the centroid 70c of the film unit 70 toward the centroid 55 of a sensing element 50 (a direction parallel to the radial line 75) to the magnetization direction urn of the magnetization free layer 11 of the sensing element 50 (for example, the direction of the magnetization 11am) is −22.5 degrees, for example. On the other hand, the angle from the direction from the centroid 70c of the film unit 70 toward the centroid 55 of the sensing element 50 (a direction parallel to the radial line 75) to the magnetization direction 12m of the reference layer 12 of the sensing element 50 is −157.5 degrees.

Thus, the relationship between the magnetization direction 11m of the magnetization free layer 11 and the radial line 75 and the relationship between the magnetization direction 12m of the reference layer 12 and the radial line 75 are different between groups.

As described above, in the circular film unit 70, the direction of strain Sa is set along the radial line 75. The polarity of the properties obtained in the sensing element 50 included in the first group G1 is the same as the polarity of the properties obtained in the sensing element 50 included in the second group G2. The polarity of the properties obtained in the sensing element 50 included in the third group G3 is the same as the polarity of the properties obtained in the sensing element 50 included in the fourth group G4. The polarity of the properties obtained in the sensing element 50 included in the first group G1 is opposite to the polarity of the properties obtained in the sensing element 50 included in the third group G3.

In this example, the angle α between the extending direction X11 of the magnetization free layer 11 and the extending direction X12 of the reference layer 12 is 135 degrees. In this case, the electric resistance R when the strain Sa is zero is equal between sensing elements 50.

The properties obtained in the sensing element 50 of the first group G1 and the second group G2 are strain sensor properties opposite to the properties obtained in the sensing element 50 of the third group G3 and the fourth group G4, with respect to the tensile and compressive strain Sa.

By forming a bridge circuit using a plurality of sensing elements 50 with polarities opposite to one another, the output is increased as described later, for example. The function of temperature compensation is obtained, for example.

In the example shown in FIG. 12, in the first sensing element 50a, the average direction of the extending direction of the first magnetic layer 11a and the extending direction of the second magnetic layer 12a is substantially parallel to the radial line 75. In the first sensing element 50a, the straight line passing through the centroid 70c of the upper surface 70u of the film unit 70 and the centroid 55 of the region where the first magnetic layer 11a and the second magnetic layer 12a overlap in a plane parallel to the upper surface 70u is defined as a first straight line LN1, for example. The difference between the absolute value of the angle (the first angle β1) between the first straight line LN1 and the first direction X1 and the absolute value of the angle (the second angle β2) between the first straight line LN1 and the second direction X2 is 5 degrees or less. The absolute value of the first angle β1 is not less than 45 degrees and not more than 90 degrees. Also the absolute value of the second angle β2 is not less than 45 degrees and not more than 90 degrees. In this example, these angles are 67.5 degrees.

In the example shown in FIG. 12, in the third sensing element 50c, the average direction of the extending direction of the fifth magnetic layer 11c and the extending direction of the sixth magnetic layer 12c is substantially perpendicular to the radial line 75. In the example shown in FIG. 12, the first sensing element 50a may be disposed in the position where the third sensing element 50c is provided. At this time, the line passing through the centroid 70c of the upper surface 70u of the film unit 70 and the centroid 55 of the region where the first magnetic layer 11a and the second magnetic layer 12a overlap in a plane parallel to the upper surface 70u is defined as a first straight line LN1. At this time, in the first sensing element 50a disposed in the position of the third sensing element 50c, the difference between the absolute value of the angle (the first angle β1) between the first straight line LN1 and the first direction X1 and the absolute value of the angle (the second angle β2) between the first straight line LN1 and the second direction X2 is 5 degrees or less. The absolute value of the first angle β1 is not less than 0 degrees and not more than 45 degrees. The absolute value of the second angle β2 is not less than 0 degrees and not more than 45 degrees. In this example, these angles are 22.5 degrees.

FIG. 13A to FIG. 13D are schematic plan views illustrating pressure sensors according to the first embodiment.

As shown in FIG. 13A and FIG. 13B, in pressure sensors 114a and 114b, the planar shape of the film unit 70 is a flat circle (including an ellipse). As shown in FIG. 13C, in a pressure sensor 114c, the planar shape of the film unit 70 is a square. As shown in FIG. 13D, in a pressure sensor 114d, the planar shape of the film unit 70 is a rectangle. In the embodiment, the planar shape of the film unit 70 may be a polygon (a regular polygon).

In the pressure sensors 114a and 114c, the distance between the sensing element 50 and the centroid 70c of the film unit 70 is equal between sensing elements 50.

In the pressure sensors 114b, 114c, and 114d, the distance between the outer edge 70r of the film unit 70 and the sensing element 50 is equal between sensing elements 50.

In the pressure sensors 114a to 114d, a plurality of sensing elements 50 are arranged radially so as to pass through the centroid 70c of the film unit 70, for example.

In the examples shown in FIG. 13A to FIG. 13D, the number of sensing elements 50 is four. In the embodiment, the number of sensing elements 50 is arbitrary.

FIG. 14A to FIG. 14D are schematic plan views illustrating pressure sensors according to the first embodiment.

As shown in FIG. 14A, in a pressure sensor 115a, the planar shape of the film unit 70 is a circle. The outer edge 70r of the film unit 70 is in a circular shape. A plurality of sensing elements 50 are arranged along the outer edge 70r in a circular shape.

As shown in FIG. 14B, in a pressure sensor 115b, the planar shape of the film unit 70 is a flat circle (including an ellipse). The outer edge 70r of the film unit 70 is in a flat circular shape. A plurality of sensing elements 50 are arranged along the outer edge 70r in a flat circular shape.

In the pressure sensors 115a and 115b, the distances between the plurality of sensing elements 50 and the outer edge 70r (the shortest distance Lmin) are equal to one another. In this example, the center of each of the plurality of sensing elements 50 is disposed in a position where the distance from the outer edge 70r is the shortest distance Lmin.

As shown in FIG. 14C, in a pressure sensor 115b, the planar shape of the film unit 70 is a square. A plurality of sensing elements 50 are arranged along the sides of the square.

As shown in FIG. 14D, in a pressure sensor 115d, the planar shape of the film unit 70 is a rectangle. A plurality of sensing elements 50 are arranged along the sides of the rectangle.

As illustrated in FIG. 14B, one straight line (for example, a second straight line) connects the outer edge 70r of the upper surface 70u of the film unit 70 and the centroid of the region where the first magnetic layer 11a and the second magnetic layer 12a overlap, by the shortest distance. The angle between the second straight line and the first direction X1 is defined as a third angle. The angle between the second straight line and the second direction X2 is defined as a fourth angle. The difference between the absolute value of the third angle and the absolute value of the fourth angle is 5 degrees or less, for example.

The absolute value of the third angle is not less than 30 degrees and not more than 60 degrees. The absolute value of the fourth angle is not less than 30 degrees and not more than 60 degrees. By setting the absolute value of the third angle and the absolute angle of the fourth angle not less than 30 degrees and not more than 60 degrees, the dynamic range of the electric resistance change with respect to the positive and negative pressure can be widened, for example. The absolute value of the third angle may be not less than 45 degrees and not more than 90 degrees. The absolute value of the third angle may be not less than 0 degrees and not more than 45 degrees. The absolute value of the fourth angle may be not less than 45 degrees and not more than 90 degrees. The absolute value of the fourth angle may be not less than 0 degrees and not more than 45 degrees.

In the embodiment, the straight line connecting the outer edge $70r$ of the upper surface $70u$ of the film unit $70$ and the centroid of the region where the first magnetic layer $11a$ and the second magnetic layer $12a$ overlap by the shortest distance is defined as a second straight line. The straight line connecting the outer edge $70r$ of the upper surface $70u$ and the centroid of the region where the third magnetic layer $11b$ and the fourth magnetic layer $12b$ overlap by the shortest distance is defined as a fourth straight line. The angle between the second straight line and the first direction X1 is defined as a third angle. The angle between the fourth straight line and the third direction X3 is defined as a sixth angle. The difference between the absolute value of the third angle and the absolute value of the sixth angle is 5 degrees or less, for example.

Figure 15A:
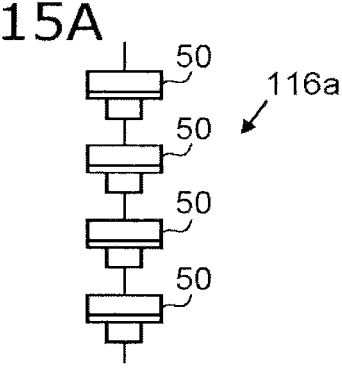
FIG. 15A to FIG. 15C are schematic diagrams showing pressure sensors according to the first embodiment.
Figure 15B:
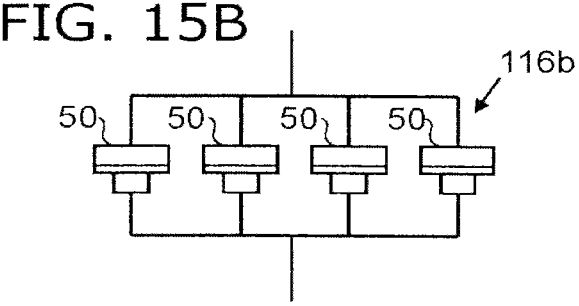
Figure 15C:
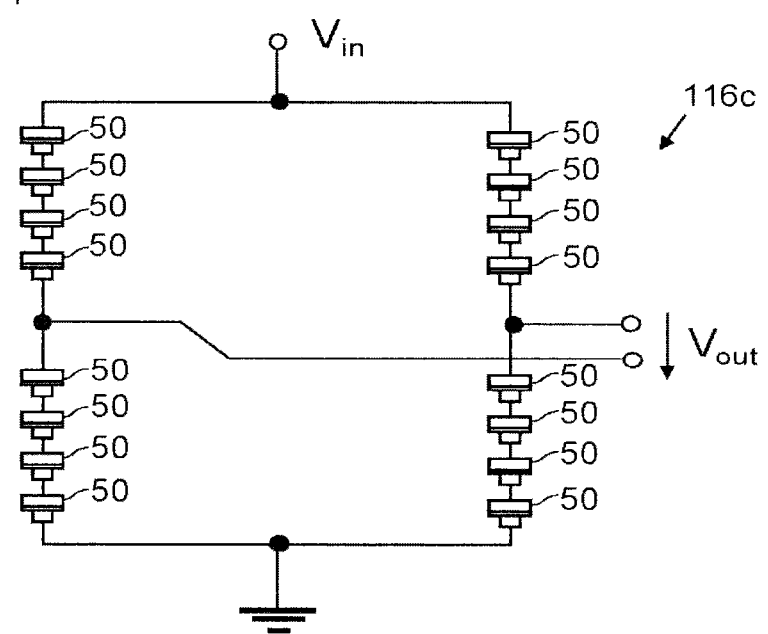

FIG. 15A to FIG. 15C are schematic diagrams illustrating pressure sensors according to the first embodiment.

The drawings show examples of the connection state of a plurality of sensing elements.

As shown in FIG. 15A, in a pressure sensor $116a$ according to the embodiment, a plurality of sensing elements $50$ are electrically connected in series. When the number of sensing elements $50$ connected in series is denoted by N, the electric signal obtained is N times of that when the number of sensing elements $50$ is one. On the other hand, the thermal noise and the Schottky noise are $N^{1/2}$ times. That is, the S/N ratio (signal-noise ratio; SNR) is $N^{1/2}$ times. By increasing the number N of sensing elements $50$ connected in series, the S/N ratio can be improved without increasing the size of the film unit $70$.

When a film unit $70$ having shape anisotropy is used, the changes in the electric resistance R with respect to the pressure (for example, the polarities) of a plurality of sensing elements $50$ that are arranged to gather near the centroid $70c$ of the film unit $70$ are similar, for example. Hence, it is possible to sum up the signals of the plurality of sensing elements $50$.

The bias voltage applied to one sensing element $50$ is not less than 50 millivolts (mV) and not more than 150 mV, for example. When N sensing elements $50$ are connected in series, the bias voltage is not less than 50 mV×N and not more than 150 mV×N. When the number N of sensing elements $50$ connected in series is 25, the bias voltage is not less than 1 V and not more than 3.75 V, for example.

When the value of the bias voltage is 1 V or more, the design of an electric circuit that processes the electric signal obtained from the sensing element $50$ is easy, and this is preferable in practical terms. A plurality of sensing elements $50$ from which electric signals with the same polarity are obtained when pressure is produced are provided, for example. By connecting these sensing elements in series, the S/N ratio can be improved as mentioned above.

Bias voltages (inter-terminal voltages) exceeding 10 V are not preferable in the electric circuit that processes the electric signal obtained from the sensing element $50$. In the embodiment, the number N of sensing elements $50$ connected in series and the bias voltage are set so that an appropriate voltage range is obtained.

The voltage when the plurality of sensing elements $50$ are electrically connected in series is preferably not less than 1 V and not more than 10 V, for example. The voltage applied between the terminals of sensing elements $50$ electrically connected in series (between the terminal of one end and the terminal of the other end) is not less than 1 V and not more than 10 V, for example.

To generate this voltage, when the bias voltage applied to one sensing element $50$ is 50 mV, the number N of sensing elements $50$ connected in series is preferably not less than 20 and not more than 200. When the bias voltage applied to one sensing element $50$ is 150 mV, the number N of sensing elements $50$ connected in series is preferably not less than 7 and not more than 66.

As shown in FIG. 15B, in a pressure sensor $116b$ according to the embodiment, a plurality of sensing elements $50$ are electrically connected in parallel. In the embodiment, at least part of a plurality of sensing elements $50$ may be electrically connected in parallel.

As shown in FIG. 15C, in a pressure sensor $116c$ according to the embodiment, a plurality of sensing elements $50$ are connected so as to form a Wheatstone bridge circuit. Thereby, the temperature compensation of detected characteristics can be made, for example.

Figure 16A:
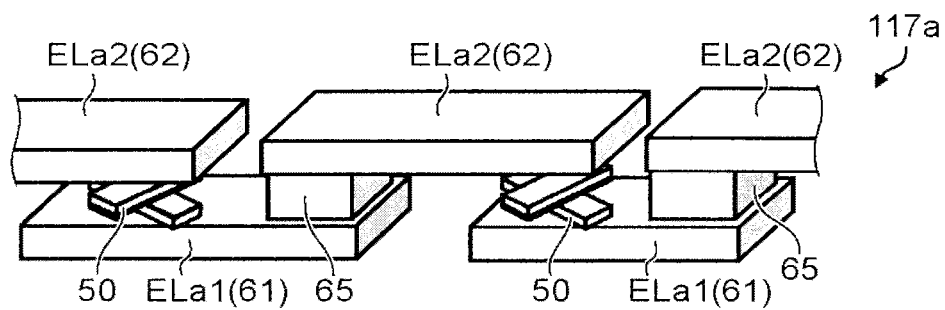
FIG. 16A to FIG. 16C are schematic perspective views showing pressure sensors according to the first embodiment.
Figure 16B:
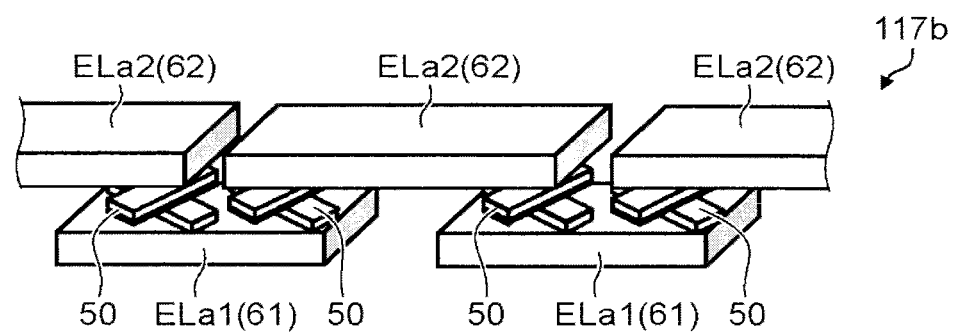
Figure 16C:
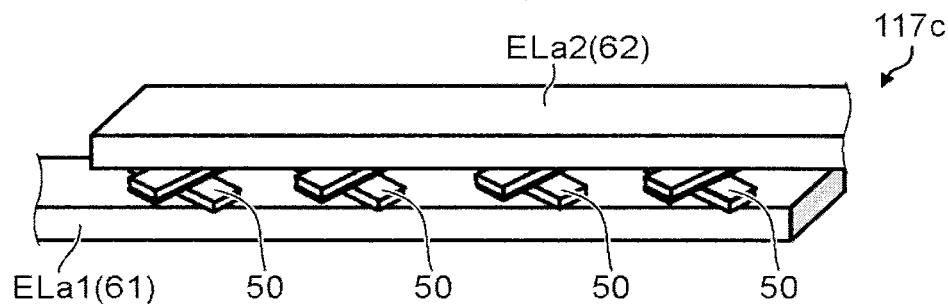

FIG. 16A to FIG. 16C are schematic perspective views illustrating pressure sensors according to the first embodiment.

The drawings show examples of the connection in a plurality of sensing elements.

As shown in FIG. 16A, in a pressure sensor $117a$ according to the embodiment, a plurality of sensing elements $50$ are electrically connected in series. The sensing element $50$ and a via contract $65$ are provided between the first electrode ELa1 (for example, the first interconnection $61$) and the second electrode ELa2 (for example, the second interconnection $62$). Thereby, the current passage direction is one direction in the plurality of sensing elements $50$. The current passed through the plurality of sensing elements $50$ is in the downward direction or the upward direction. In this connection, the signal/noise characteristics of the plurality of sensing elements $50$ can be made close to one another.

As shown in FIG. 16B, in a pressure sensor $117b$ according to the embodiment, the via contact $65$ is not provided, and the sensing element $50$ is disposed between the first electrode ELa1 and the second electrode ELa2. In this example, the directions of the currents passed through adjacent two sensing elements $50$ are opposite to each other. In this connection, the density of the arrangement of sensing elements $50$ is high.

As shown in FIG. 16C, in a pressure sensor $117c$ according to the embodiment, a plurality of sensing elements $50$ are provided between one first electrode ELa1 and one second electrode ELa2. The plurality of sensing elements $50$ are connected in parallel.

FIG. 17A to FIG. 17E are schematic perspective views illustrating pressure sensors according to the first embodiment.

Figure 17A:
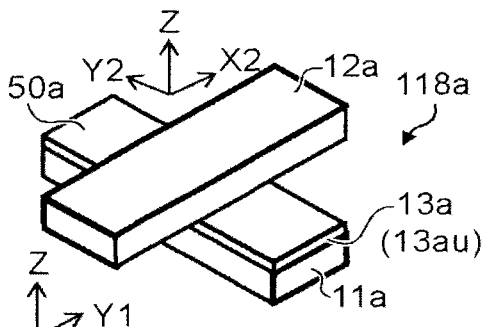
FIG. 17A to FIG. 17E are schematic perspective views showing pressure sensors according to the first embodiment.

As shown in FIG. 17A, in a pressure sensor $118a$ according to the embodiment, in the first sensing element $50a$, the planar shape of the first intermediate layer $13a$ (the first intermediate unit $13au$) is the same as the planar shape of the first magnetic layer 11a. That is, the shape of the first intermediate unit 13au in the X-Y plane (a plane parallel to the upper surface 70u of the film unit 70) is the same as the shape of the first magnetic layer 11a in the X-Y plane, for example.

Figure 17B:
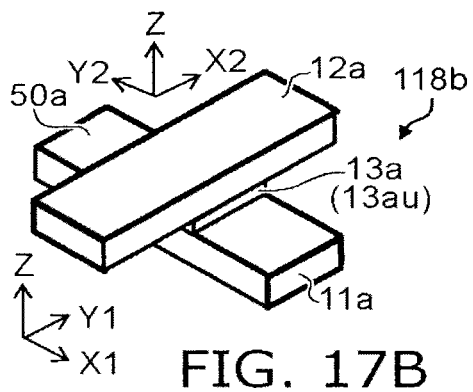

As shown in FIG. 17B, in a pressure sensor 118b according to the embodiment, the planar shape of the first intermediate layer 13a (the first intermediate unit 13au) is different from the planar shape of the first magnetic layer 11a and is different also from the planar shape of the second magnetic layer 12a. The shape of the first intermediate unit 13au in the X-Y plane is the same as the shape of the region where the first magnetic layer 11a and the second magnetic layer 12a overlap in the X-Y plane, for example.

Figure 17C:
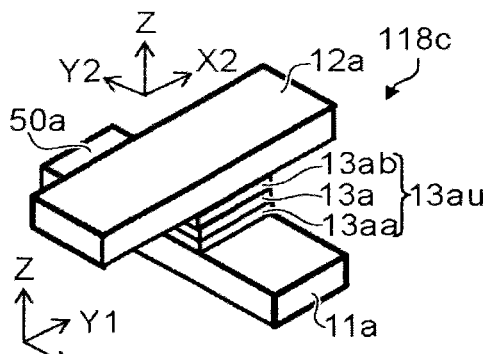

As shown in FIG. 17C, in a pressure sensor 118c according to the embodiment, the first intermediate unit 13au further includes a first intermediate magnetic layer 13aa provided between the first intermediate layer 13a and the first magnetic layer 11a and a second intermediate magnetic layer 13ab provided between the first intermediate layer 13a and the second magnetic layer 12a.

In this example, the shape of the first intermediate unit 13au in the X-Y plane is the same as the shape of the region where the first magnetic layer 11a and the second magnetic layer 12a overlap in the X-Y plane, for example.

The stacked film including the first intermediate magnetic layer 13aa, the first intermediate layer 13a, and the first intermediate magnetic layer 13aa, which stacked film contributes to the magnetoresistance effect due to the existence of the first intermediate magnetic layer 13aa and the second intermediate magnetic layer 13ab, can be formed by consistent film formation under a reduced pressure. Thereby, a high magnetoresistance effect is obtained, for example.

The first magnetic layer 11a and the first intermediate magnetic layer 13aa are magnetically coupled, for example. The magnetization direction of the first intermediate magnetic layer 13aa is set along the magnetization direction of the first magnetic layer 11a. The second magnetic layer 12a and the second intermediate magnetic layer 13ab are magnetically coupled. The magnetization direction of the second intermediate magnetic layer 13ab is set along the magnetization direction of the second magnetic layer 12a.

Even when substantially neither the planar shape of the first intermediate magnetic layer 13aa nor the planar shape of the second intermediate magnetic layer 13ab has shape anisotropy, the initial magnetization of the first intermediate magnetic layer 13aa and the initial magnetization of the second intermediate magnetic layer 13ab can be controlled because the planar shape of the first magnetic layer 11a and the planar shape of the second magnetic layer 12a have shape anisotropy.

The material described in regard to the first magnetic layer 11a may be used for at least one of the first intermediate magnetic layer 13aa and the second intermediate magnetic layer 13ab, for example.

Figure 17D:
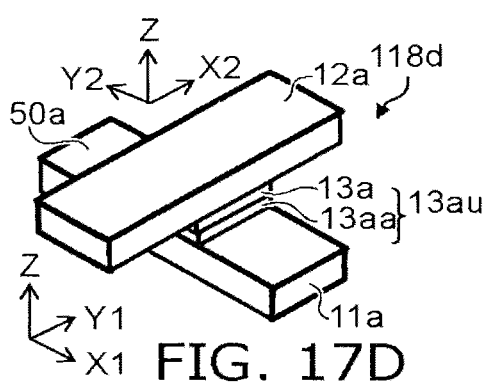

As shown in FIG. 17D, in a pressure sensor 118d according to the embodiment, the first intermediate unit 13au includes the first intermediate layer 13a and the first intermediate magnetic layer 13aa. Also in this case, the shape of the first intermediate unit 13au in the X-Y plane is the same as the shape of the region where the first magnetic layer 11a and the second magnetic layer 12a overlap in the X-Y plane, for example.

The stacked film including the first intermediate layer 13a and the first intermediate magnetic layer 13aa, which stacked film contributes to the magnetoresistance effect due to the existence of the first intermediate magnetic layer 13aa, can be formed by consistent film formation under a reduced pressure. Thereby, a high magnetoresistance effect is obtained, for example.

Also at this time, the first magnetic layer 11a and the first intermediate magnetic layer 13aa are magnetically coupled, for example. The magnetization direction of the first intermediate magnetic layer 13aa is set along the magnetization direction of the first magnetic layer 11a.

Figure 17E:
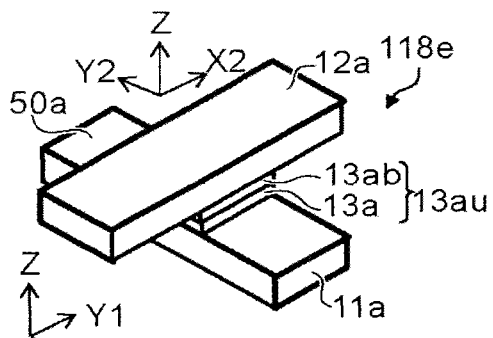

As shown in FIG. 17E, in a pressure sensor 118e according to the embodiment, the first intermediate unit 13au includes the first intermediate layer 13a and the second intermediate magnetic layer 13ab. Also in this case, the shape of the first intermediate unit 13au in the X-Y plane is the same as the shape of the region where the first magnetic layer 11a and the second magnetic layer 12a overlap in the X-Y plane, for example.

The stacked film including the first intermediate layer 13a and the second intermediate magnetic layer 13ab, which stacked film contributes to the magnetoresistance effect due to the existence of the second intermediate magnetic layer 13ab, can be formed by consistent film formation under a reduced pressure. Thereby, a high magnetoresistance effect is obtained, for example.

Also at this time, the second magnetic layer 12a and the second intermediate magnetic layer 13ab are magnetically coupled, for example. The magnetization direction of the second intermediate magnetic layer 13ab is set along the magnetization direction of the second magnetic layer 11b.

Figure 18A:
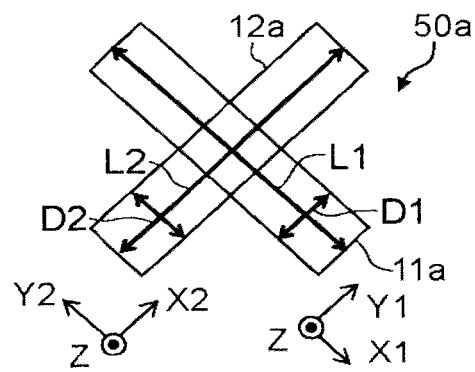
FIG. 18A and FIG. 18B are schematic plan views showing the pressure sensor according to the first embodiment.
Figure 18B:
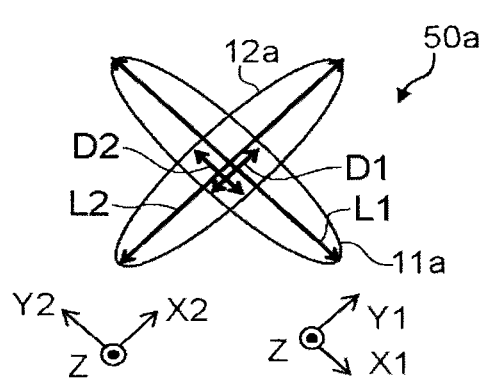

FIG. 18A and FIG. 18B are schematic plan views illustrating the pressure sensor according to the first embodiment.

In the example shown in FIG. 18A, the planar shape of the first magnetic layer 11a is a rectangle, and the planar shape of the second magnetic layer 12a is a rectangle. In the example shown in FIG. 18B, the planar shape of the first magnetic layer 11a is an ellipse, and the planar shape of the second magnetic layer 12a is an ellipse.

The planar shape of the first magnetic layer 11a may be a quadrangle such as a parallelogram or a flat circle (including an ellipse), for example. The planar shape of the second magnetic layer 12a may be a quadrangle such as a parallelogram or a flat circle (including an ellipse), for example.

In the first sensing element 50a, the first major axis length L1 is not less than twice the first minor axis length D1, for example. The second major axis length L2 is not more than twice the second minor axis length D2.

In the embodiment, pressure can be sensed with a sufficiently high sensitivity even when the size of the magnetization free layer 11 (for example, the first magnetic layer 11a) and the size of the reference layer 12 (for example, the second magnetic layer 12a) are small.

Thus, the area of the first magnetic layer 11a and the area of the second magnetic layer 12a can be made sufficiently smaller than the area of the film unit 70. Each of the area of the first magnetic layer 11a and the area of the second magnetic layer 12a is not more than ⅕ of the area of the film unit 70, for example.

When the diameter of the film unit 70 is approximately 60 μm, each of the first minor axis length D1 of the first magnetic layer 11a and the second minor axis length D2 of the second magnetic layer 12a is 12 μm or less, for example.

When the diameter of the film unit 70 is approximately 600 μm, each of the first minor axis length D1 of the first magnetic layer 11a and the second minor axis length D2 of the second magnetic layer 12a is 120 μm or less, for example.

In view of the processing accuracy of the sensing element 50 etc., the first magnetic layer 11a and the second magnetic layer 12a may not be excessively small, for example. Each of the first minor axis length D1 and the second minor axis length D2 may be not less than 0.05 µm and not more than 30 µm, for example.

Each of the first major axis length L1 of the first magnetic layer 11a and the second major axis length L2 of the second magnetic layer 12a is preferably not less than 0.1 µm and not more than 60 µm, for example.

The above description is applied to any one of the pressure sensors 110, 111, 112a to 112c, 113a, 113b, 116a to 116c, 117a to 117c, and 118a to 118e, and modifications thereof.

FIG. 19A to FIG. 19D are schematic plan views illustrating the pressure sensor according to the first embodiment.

Figure 19A:
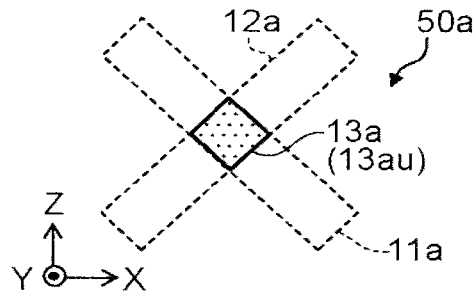
FIG. 19A to FIG. 19D are schematic plan views showing the pressure sensor according to the first embodiment.

In the example shown in FIG. 19A, the shape of the first intermediate unit 13au in the X-Y plane is the same as the shape of the region where the first magnetic layer 11a and the second magnetic layer 12a overlap in the X-Y plane.

Figure 19B:
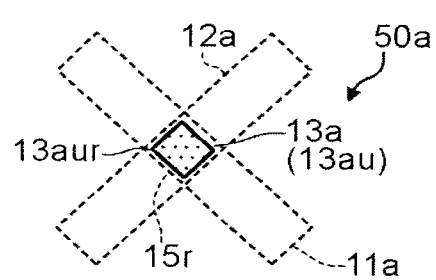

In the example shown in FIG. 19B, the first intermediate unit 13au in the X-Y plane is located inside the region where the first magnetic layer 11a and the second magnetic layer 12a overlap in the X-Y plane.

Figure 19C:
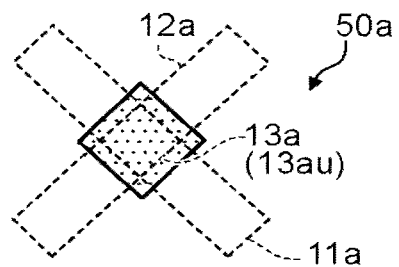

In the example shown in FIG. 19C, the outer edge of the first intermediate unit 13au in the X-Y plane is located outside the outer edge of the region where the first magnetic layer 11a and the second magnetic layer 12a overlap in the X-Y plane.

Figure 19D:
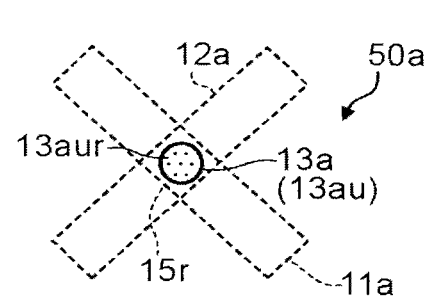

In the example shown in FIG. 19D, the shape of the first intermediate unit 13au in the X-Y plane is a circle, and the shape of the region where the first magnetic layer 11a and the second magnetic layer 12a overlap in the X-Y plane is a rectangular shape.

In the examples shown in FIG. 19B and FIG. 19D, the outer edge 13aur of a first intermediate unit region of the first intermediate unit 13au in the X-Y plane (a plane parallel to the upper surface 70u of the film unit 70) is on the inside of the outer edge 15r of the region where the first magnetic layer 11a and the second magnetic layer 12a overlap in the X-Y plane.

Figure 20:
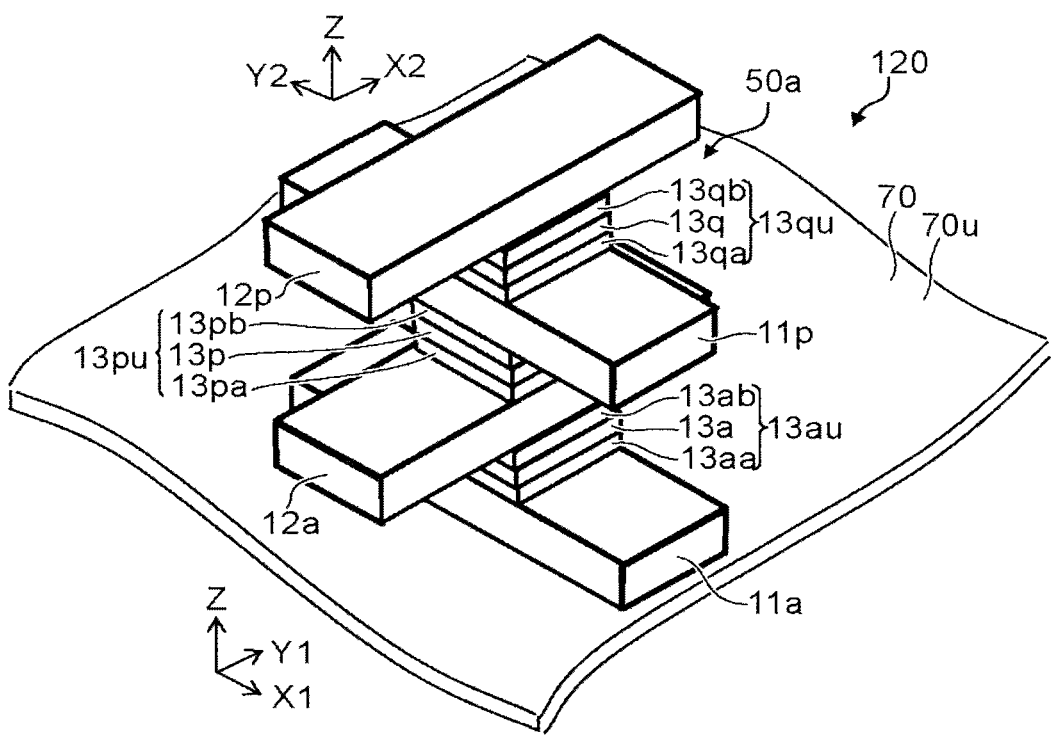
FIG. 20 is a schematic perspective view showing a pressure sensor according to the first embodiment.

FIG. 20 is a schematic perspective view illustrating a pressure sensor according to the first embodiment.

As shown in FIG. 20, also in another pressure sensor 120 according to the embodiment, the first sensing element 50a is provided on the upper surface 70u of the film unit 70. The first sensing element 50a further includes an upper magnetic layer 12p, a middle magnetic layer 11p, an upper intermediate unit 13qu, and a middle intermediate unit 13pu, in addition to the first magnetic layer 11a, the first intermediate unit 13au, and the second magnetic layer 12a.

In this example, at least part of the first magnetic layer 11a is disposed between the upper magnetic layer 12p and the film unit 70. At least part of the second magnetic layer 12a is disposed between the upper magnetic layer 12p and the first magnetic layer 11a. At least part of the middle magnetic layer 11p is disposed between the upper magnetic layer 12p and the second magnetic layer 12a. At least part of the upper magnetic layer 12p is disposed between the upper magnetic layer 12p and the middle magnetic layer 11p.

At least part of the upper intermediate unit 13qu is disposed between the upper magnetic layer 12p and the middle magnetic layer 11p. At least part of the middle intermediate unit 13pu is disposed between the middle magnetic layer 11p and the second magnetic layer 12a.

In this example, the upper intermediate unit 13qu includes an upper intermediate layer 13q, an upper-side magnetic layer 13qb, and a lower-side magnetic layer 13qa. At least part of the upper-side magnetic layer 13qb is provided between the upper intermediate layer 13q and the upper magnetic layer 12p. At least part of the lower-side magnetic layer 13qa is provided between the upper intermediate layer 13q and the middle magnetic layer 11p.

In this example, the middle intermediate unit 13pu includes a middle intermediate layer 13p, an upper-side magnetic layer 13pb, and a lower-side magnetic layer 13pa. At least part of the upper-side magnetic layer 13pb is provided between the middle intermediate layer 13p and the middle magnetic layer 11p. At least part of the lower-side magnetic layer 13pa is provided between the middle intermediate layer 13p and the second magnetic layer 12a.

The configuration and material described in regard to the second magnetic layer 12a may be used for the upper magnetic layer 12p, for example. The configuration and material described in regard to the first magnetic layer 11a may be used for the middle magnetic layer 11p, for example.

The configuration and material described in regard to the first intermediate layer 13a may be used for at least one of the upper intermediate layer 13q and the middle intermediate layer 13p. The configuration and material described in regard to the second intermediate magnetic layer 13ab may be used for at least one of the upper-side magnetic layer 13qb and the upper-side magnetic layer 13pb. The configuration and material described in regard to the first intermediate magnetic layer 13aa may be used for at least one of the lower-side magnetic layer 13qa and the lower-side magnetic layer 13pa.

A magnetization free layer may be used as at least one of the middle magnetic layer 11p and the upper magnetic layer 12p, for example.

The middle magnetic layer 11p has shape anisotropy, for example. The upper magnetic layer 12p has shape anisotropy. In this example, the extending direction of the middle magnetic layer 11p is set along the extending direction of the first magnetic layer 11a (the first direction X1). The extending direction of the upper magnetic layer 12p is set along the extending direction of the second magnetic layer 12a (the second direction X2).

In the embodiment, the extending direction of the middle magnetic layer 11p may cross the extending direction of the first magnetic layer 11a. The extending direction of the upper magnetic layer 12p may cross the extending direction of the second magnetic layer 12a (the second direction X2).

The configuration of the pressure sensor 120 may be used for any one of the pressure sensors 110, 111, 112a to 112c, 113a, 113b, 116a to 116c, 117a to 117c, and 118a to 118e, and modifications thereof.

A method for manufacturing the pressure sensor 118c will now be described.

FIG. 21A to FIG. 21M are schematic perspective views in order of the steps, illustrating a method for manufacturing a pressure sensor according to the first embodiment.

Figure 21A:
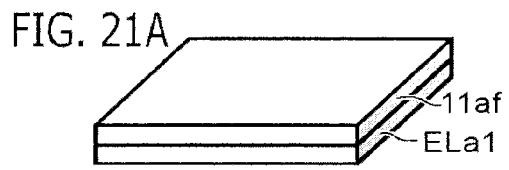
FIG. 21A to FIG. 21M are schematic perspective views in order of the steps, showing a method for manufacturing a pressure sensor according to the first embodiment.

As shown in FIG. 21A, a first magnetic film 11af that forms the first magnetic layer 11a is formed on the first electrode ELa1. It is possible to form the underlayer 11al on the first electrode ELa1 and form a second magnetic film 11af on the underlayer 11al. In FIG. 20A, the underlayer 11al is omitted.

It is possible to process a film that forms the first electrode ELa1 and form the planar shape of the first electrode ELa1 before the formation of the underlayer 11al and the first magnetic film 11af. Alternatively, after the processing of the stacked film included in the sensing element is finished, the first electrode ELa1 may be processed to form the planar shape of the first electrode ELa1.

A cap layer (not shown) may be formed into a film on the first magnetic film 11*af*. The cap layer can suppress oxidation etc. when the first magnetic film 11*af* is exposed to the air. The cap layer can be removed by physical etching before the film formation of the intermediate unit, as described later.

Ta (5 nm)/Cu (5 nm)/CoFeSiB (12 nm)/MgO (3 nm) is formed on the first electrode ELa1, for example. The Ta (5 nm)/Cu (5 nm) corresponds to the underlayer. The CoFeSiB (12 nm) corresponds to the first magnetic film 11*af*. The MgO (3 nm) corresponds to the cap layer.

Figure 21B:
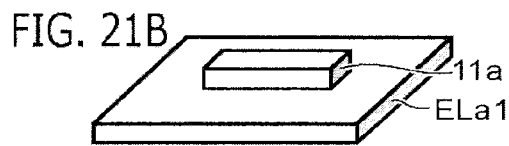

As shown in FIG. 21B, the film including the underlayer 11*al*/the first magnetic film 11*af*/the cap layer is processed into a shape having shape anisotropy. In this process, a resist is patterned by photolithography, and then the not-shown resist pattern is used as a mask to perform physical etching or chemical etching, for example. Thereby, the first magnetic layer 11*a* is formed.

Figure 21C:
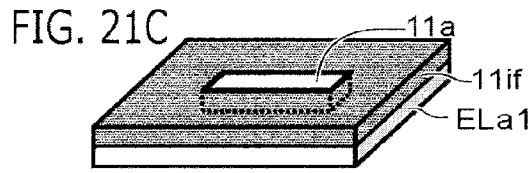

As shown in FIG. 21C, an insulating layer 11*if* is embedded and formed into a film around the film including the underlayer 11*al*/the first magnetic layer 11*a*/the cap layer. A lift-off process is performed, for example. While the resist pattern formed in the photolithography of FIG. 21C is left, the insulating layer 11*if* is formed into a film over the entire surface, and then the resist pattern is removed, for example. As the insulating layer 11*if*, at least one of $SiO_x$, $AlO_x$, $SiN_x$ and $AlN_x$ is used, for example.

Figure 21D:
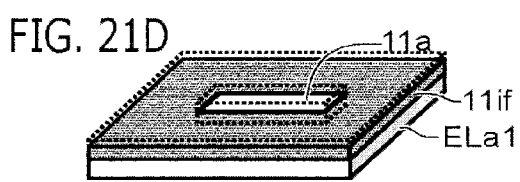

As shown in FIG. 21D, part of the cap layer provided on the first magnetic layer 11*a* and part of the surrounding insulating layer 11*if* are removed by physical etching. In the case where the cap layer has not been provided, the oxidized portion of the first magnetic layer 11*a* is removed by physical etching in this process. In the case where a material that is hardly oxidized even when exposed to the air is used as the first magnetic layer 11*a*, the process of FIG. 21D may not necessarily be performed, for example.

In this process, part of the Ta (5 nm)/Cu (5 nm)/CoFeSiB (12 nm)/MgO (3 nm) formed in the process described in regard to FIG. 21A is removed, for example. Thereby, a structure of Ta (5 nm)/Cu (5 nm)/CoFeSiB (8 nm) is formed.

The process shown in FIG. 21E described later and the process shown in FIG. 21D are performed consistently under a reduced pressure using the same apparatus, for example. Thereby, the film formation of the intermediate unit of FIG. 21E can be performed while the surface of the first magnetic layer 11*a* after the process of FIG. 21D is kept clean.

Figure 21E:
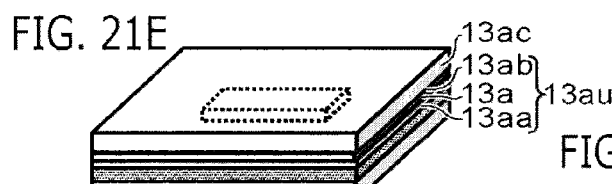

As shown in FIG. 21E, the first intermediate unit 13*au* including the first intermediate magnetic layer 13*aa*, the first intermediate layer 13*a*, and the second intermediate magnetic layer 13*ab* is formed. A cap layer 13*ac* may be provided on the second intermediate magnetic layer 13*ab*. CoFeB (2 nm)/MgO (2 nm)/CoFeB (6 nm)/MgO (3 nm) is formed, for example. The CoFeB (2 nm) corresponds to the first intermediate magnetic layer 13*aa*. The MgO (2 nm) corresponds to the first intermediate layer 13*a*. The CoFeB (6 nm) corresponds to the second intermediate magnetic layer 13*ab*. The MgO (3 nm) corresponds to the cap layer 13*ac*.

Figure 21F:
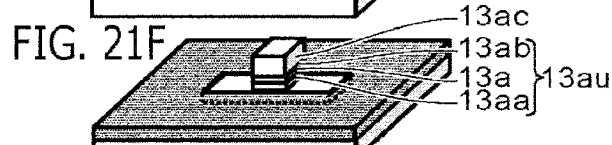

As shown in FIG. 21F, the first intermediate magnetic layer 13*aa*/the first intermediate layer 13*a*/the second intermediate magnetic layer 13*ab*/the cap layer 13*ac* is processed into a prescribed planar shape. In this process, a resist is patterned by photolithography, and then the not-shown resist pattern is used as a mask to perform physical etching or chemical etching.

Figure 21G:
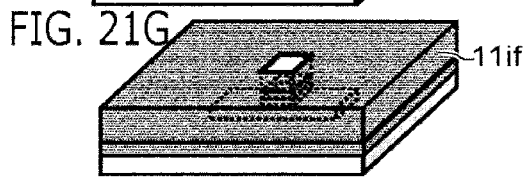

As shown in FIG. 21G, an insulating layer 11*ifa* is embedded and formed into a film around the first intermediate magnetic layer 13*aa*/the first intermediate layer 13*a*/the second intermediate magnetic layer 13*ab*/the cap layer 13*ac*. In this process, a lift-off process is performed, for example. While the resist pattern formed in the photolithography of FIG. 21F is left, the insulating layer 11*ifa* is formed into a film over the entire surface, and then the resist pattern is removed, for example. At least one of $SiO_x$, $AlO_x$, $SiN_x$, and $AlN_x$ is used as the insulating layer 11*ifa*, for example.

Figure 21H:
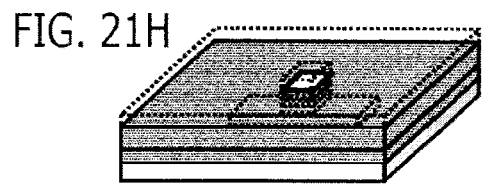

As shown in FIG. 21H, part of the cap layer 13*ac* provided on the second intermediate magnetic layer 13*ab* and part of the surrounding insulating layer 11*ifa* are removed by physical etching.

In the case where the cap layer 13*ac* has not been provided, the oxidized portion of the second intermediate magnetic layer 13*ab* is removed by physical etching. In the case where a material that is hardly oxidized even when exposed to the air is used as the second intermediate magnetic layer 13*ab*, the process of FIG. 21H may not necessarily be performed.

In this process, part of the CoFeB (2 nm)/MgO (2 nm)/CoFeB (6 nm)/MgO (3 nm) formed into a film in FIG. 21E is removed, for example. Thereby, a structure of CoFeB (2 nm)/MgO (2 nm)/CoFeB (2 nm) is formed.

The process of FIG. 21I described later and the process shown in FIG. 21H are performed consistently under a reduced pressure using the same apparatus. Thereby, a film that forms the second magnetic layer 12*a* shown in FIG. 21I can be formed while the surface of the second intermediate magnetic layer 13*ab* after the process of FIG. 21H is kept clean.

Figure 21I:
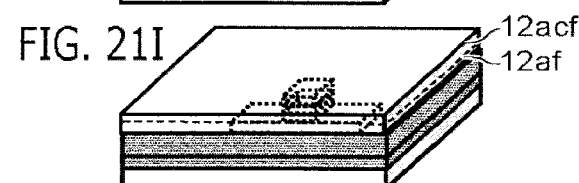

As shown in FIG. 21I, a second magnetic film 12*af* that forms the second magnetic layer 12*a* and a cap film 12*acf* that forms the cap layer 12*ac* are formed. CoFeSiB (4 nm)/Cu (5 nm)/Ru (10 nm) is formed into a film, for example. The CoFeSiB (4 nm) corresponds to the second magnetic film 12*af* (the second magnetic layer 12*a*). The Cu (5 nm)/Ru (10 nm) corresponds to the cap film 12*acf* (the cap layer 12*ac*).

Figure 21J:
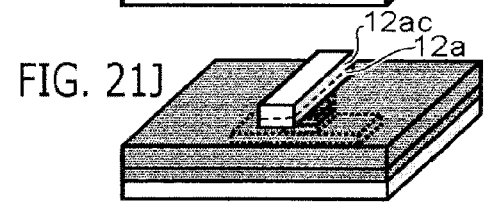

As shown in FIG. 21J, the second magnetic film 12*af* and the cap film 12*acf* are processed into a shape having shape anisotropy. Thereby, the second magnetic layer 12*a* and the cap layer 12*ac* are formed. In this process, a resist is patterned by photolithography, and then the not-shown resist pattern is used as a mask to perform physical etching or chemical etching.

Figure 21K:
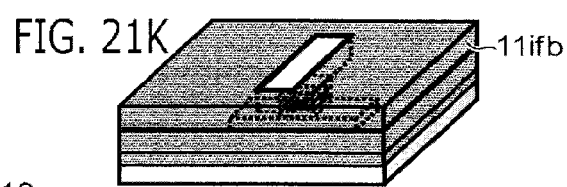

As shown in FIG. 21K, an insulating layer 11*ifb* is embedded and formed into a film around the second magnetic layer 12*a* and the cap layer 12*ac*. In this process, a lift-off process is performed, for example. While the resist pattern formed in the photolithography of FIG. 21J is left, the insulating layer 11*ifb* is formed into a film over the entire surface, and then the resist pattern is removed, for example. At least one of $SiO_x$, $AlO_x$, $SiN_x$, and $AlN_x$ is used as the insulating layer 11*ifb*, for example.

Figure 21L:
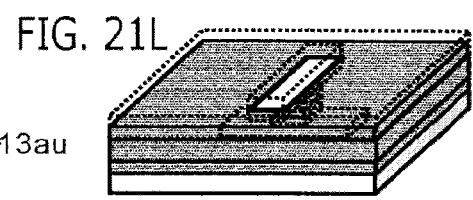

As shown in FIG. 21L, part of the cap layer 12*ac* and part of the surrounding insulating layer 11*ifb* are removed by physical etching. In the case where the cap layer 12*ac* has not been provided, the oxidized portion of the second magnetic layer 12*a* is removed by physical etching. In the case where a material that is hardly oxidized even when exposed to the air is used as the second magnetic layer 12a, the process of FIG. 21L may not necessarily be performed, for example.

In this process, part of the CoFeSiB (4 nm)/Cu (5 nm)/Ru (10 nm) formed into a film in FIG. 21I is removed, for example. Thereby, a structure of CoFeSiB (4 nm)/Cu (5 nm)/Ru (5 nm) is formed. The process of FIG. 21M described later and the process shown in FIG. 21L are performed consistently under a reduced pressure using the same apparatus. Thereby, the second magnetic layer 12a of FIG. 21M can be formed into a film while the surface of the cap layer 12ac after the process of FIG. 21L is kept clean.

Figure 21M:
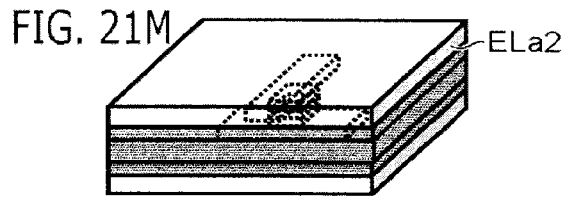

As shown in FIG. 21M, the second electrode ELa2 is formed.

By such a process, the first sensing element 50a is formed.

FIG. 22A to FIG. 22F are schematic views in order of the steps, illustrating a method for manufacturing a pressure sensor according to the first embodiment.

Figure 22A:
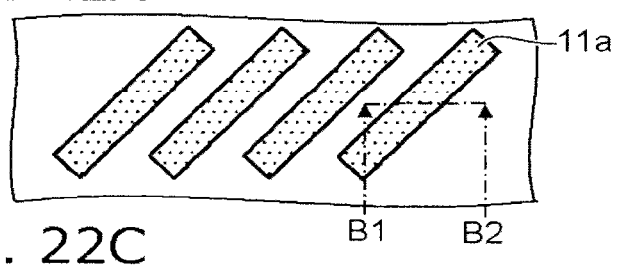
FIG. 22A to FIG. 22F are schematic views in order of the steps, showing a method for manufacturing a pressure sensor according to the first embodiment.
Figure 22B:
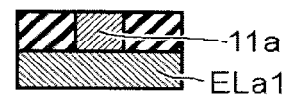
Figure 22C:
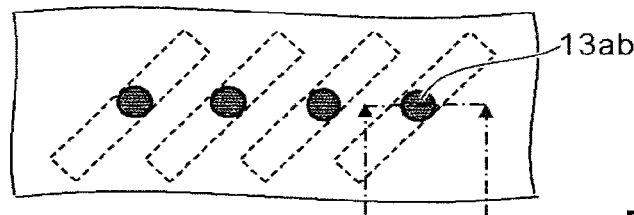
Figure 22D:
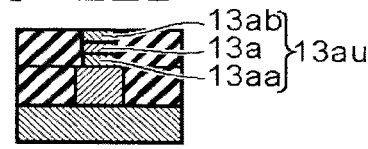
Figure 22E:
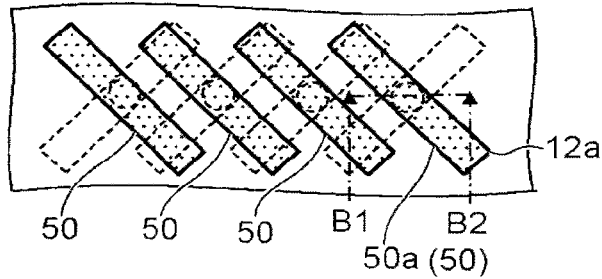
Figure 22F:
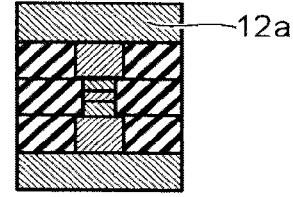

FIG. 22A, FIG. 22C, and FIG. 22E are schematic plan views. FIG. 22B is a cross-sectional view taken along line B1-B2 of FIG. 22A. FIG. 22D is a cross-sectional view taken along line B3-B4 of FIG. 22C. FIG. 22F is a cross-sectional view taken along line B5-B6 of FIG. 22E. The drawings show also an example of the structure of adjacent sensing elements 50.

As shown in FIG. 22A and FIG. 22B, the first magnetic layer 11a is formed on the first electrode ELa1. As shown in FIG. 22C and FIG. 22D, the first intermediate unit 13au is formed on the first magnetic layer 11a. As shown in FIG. 22E and FIG. 22F, the second magnetic layer 12a is formed on the first intermediate unit 13au. Thus, the sensing element 50 (the first sensing element 50a) is formed.

In this example, the first intermediate unit 13au is formed separately from the first magnetic layer 11a and from the second magnetic layer 12a.

In this case, as illustrated in FIG. 22E and FIG. 22F, in different sensing elements 50, the first magnetic layer 11a and the second magnetic layer 12a may be provided so as to overlap each other when projected onto the X-Y plane. When the intermediate units do not overlap in different sensing elements 50, the different sensing elements 50 can be operated electrically independently. A plurality of sensing elements 50 can be connected together at least one of in series and in parallel by the arrangement of the first electrode ELa1 and the second electrode ELa2 provided in the sensing element 50, for example. Since the first magnetic layer 11a and the second magnetic layer 12a overlap each other in different sensing elements 50, sensing elements 50 can be arranged at high density.

A method for manufacturing the pressure sensor 110 will now be described.

FIG. 23A to FIG. 23E are schematic perspective views in order of the steps, illustrating a method for manufacturing a pressure sensor according to the embodiment.

Figure 23A:
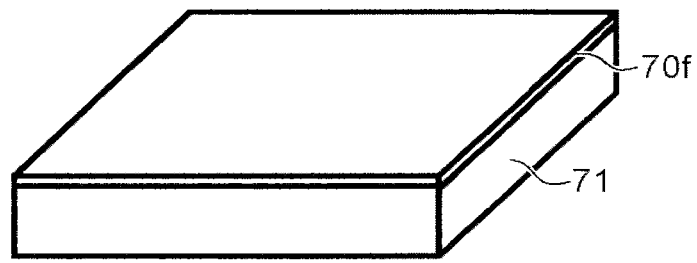
FIG. 23A to FIG. 23E are schematic perspective views in order of the steps, showing a method for manufacturing a pressure sensor according to the embodiment.

As shown in FIG. 23A, a thin film 70f is formed on a substrate 71 (for example, a Si substrate). The substrate 71 forms the support 70s. The thin film 70f forms the film unit 70.

A thin film 70f of $SiO_x$/Si is formed by sputtering on a Si substrate, for example. A $SiO_x$ single layer, a SiN single layer, or a metal layer of Al or the like may be used as the thin film 70f. A flexible plastic material such as a polyimide and a paraxylene-based polymer may be used as the thin film 70f. An SOI (silicon on insulator) substrate may be used as the substrate 71 and the thin film 70f. In the SOI, a stacked film of $SiO_2$/Si is formed on a Si substrate by attaching the substrates, for example.

Figure 23B:
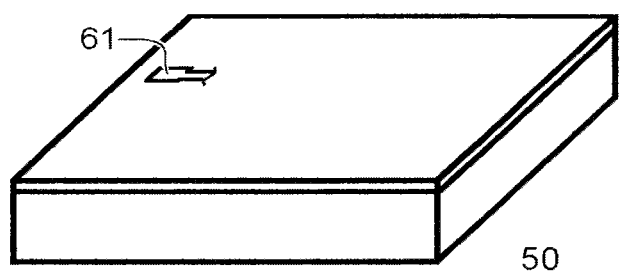

As shown in FIG. 23B, the first interconnection 61 is formed. In this process, a conductive film that forms the first interconnection 61 is formed, and the conductive film is processed by photolithography and etching. In the case where the surroundings of the first interconnection 61 are filled with an insulating film, lift-off process may be used. In the lift-off process, after the etching of the pattern of the first interconnection 61 and before the peeling of the resist, an insulating film is formed into a film over the entire surface and then the resist is removed, for example.

Figure 23C:
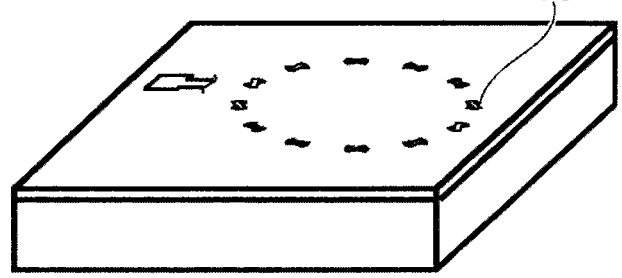

As shown in FIG. 23C, sensing elements 50 are formed. In this process, a stacked film that forms the sensing element 50 is formed, and the stacked film is processed by photolithography and etching. In the case where the space on the side wall of the stacked body of the sensing element 50 is filled with the insulating layer 11i, lift-off process may be used. In the lift-off process, after the processing of the stacked body and before the peeling of the resist, the insulating layer 11i is formed into a film over the entire surface and then the resist is removed, for example.

Figure 23D:
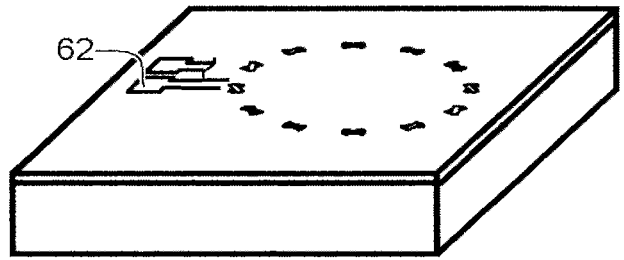

As shown in FIG. 23D, the second interconnection 62 is formed. In this process, a conductive film that forms the first interconnection 62 is formed, and the conductive film is processed by photolithography and etching. In the case where the surroundings of the second interconnection 62 are filled with an insulating film, lift-off process may be used. In the lift-off process, after the processing of the second interconnection 62 and before the peeling of the resist, an insulating film is formed into a film over the entire surface and then the resist is removed.

Figure 23E:
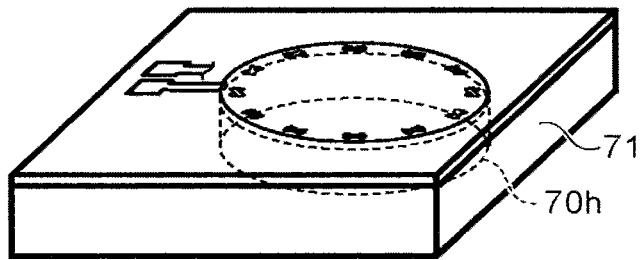

As shown in FIG. 23E, etching is performed from the back surface of the substrate 71 to form a hollow portion 71h. Thereby, the film unit 70 and the support 70s are formed. In the case where a stacked film of $SiO_x$/Si is used as the thin film 70f that forms the film unit 70, deep digging processing of the substrate 71 is performed from the back surface (the lower surface) toward the front surface (the upper surface) of the thin film 70f, for example. Thereby, the hollow portion 71h is formed. In the formation of the hollow portion 71h, a both-surface aligner exposure apparatus may be used, for example. Thereby, the hole pattern of the resist can be formed on the back surface in accordance with the position of the sensing element 50 on the front surface.

In the etching of the Si substrate, the Bosch process using RIE may be used, for example. In the Bosch process, an etching process using $SF_6$ gas and a deposition process using $C_4F_8$ gas are repeated, for example. Thereby, etching is performed selectively in the depth direction of the substrate 71 (the Z-axis direction) while the etching of the side wall of the substrate 71 is suppressed. A $SiO_x$ layer is used as the end point of the etching, for example. That is, the etching is finished using a $SiO_x$ layer, which is different in etching selectivity from Si. The $SiO_x$ layer functioning as an etching stopper layer may be used as part of the film unit 70. The $SiO_x$ layer may be removed after the etching by treatment with anhydrous hydrogen fluoride and an alcohol, or the like, etc., for example.

Thus, the pressure sensor 110 according to the embodiment is formed. Other pressure sensors according to the embodiment can be manufactured by similar methods.

FIG. 24A to FIG. 24C are schematic cross-sectional views illustrating pressure sensors according to the first embodiment.

In the pressure sensors illustrated in FIG. 24A and FIG. 24B, a magnetization fixed layer is used as the reference layer of the second magnetic layer 12a. In the pressure sensor illustrated in FIG. 24C, two magnetization fixed layers are used.

The drawings illustrate the sensing element 50 (the first sensing element 50a).

In the example shown in FIG. 24A, the first sensing element 50a includes the first electrode ELa1 (a lower electrode), the underlayer 11al, the first magnetic layer 11a, the first intermediate layer 13a, the second magnetic layer 12a, a pinning layer 32, the cap layer 12ac, and the second electrode ELa2 (an upper electrode). The first magnetic layer 11a is provided between the first electrode ELa1 and the second electrode ELa2. The second magnetic layer 12a is provided between the first magnetic layer 11a and the second electrode ELa2. The first intermediate layer 13a is provided between the first magnetic layer 11a and the second magnetic layer 12a. The underlayer 11al is provided between the first magnetic layer 11a and the first electrode ELa1. The cap layer 12ac is provided between the second magnetic layer 12a and the second electrode ELa2. The pinning layer 32 is provided between the second magnetic layer 12a and the cap layer 12ac.

In the example shown in FIG. 24B, the first sensing element 50a includes the first electrode ELa1 (a lower electrode), the underlayer 11al, a pinning layer 31, the second magnetic layer 12a, the first intermediate layer 13a, the first magnetic layer 11a, the cap layer 12ac, and the second electrode ELa2 (an upper electrode). The first magnetic layer 11a is provided between the first electrode ELa1 and the second electrode ELa2. The second magnetic layer 12a is provided between the first electrode ELa1 and the first magnetic layer 11a. The first intermediate layer 13a is provided between the first magnetic layer 11a and the second magnetic layer 12a. The underlayer 11al is provided between the second magnetic layer 12a and the first electrode ELa1. The cap layer 12ac is provided between the first magnetic layer 11a and the second electrode ELa2. The pinning layer 31 is provided between the second magnetic layer 12a and the underlayer 11al.

In the pressure sensor illustrated in FIG. 24C, an upper intermediate layer 34 is further provided to the pressure sensor illustrated in FIG. 24B, between the second magnetic layer 12a and the cap layer 12ac. An upper pinned layer 33 is further provided between the upper intermediate layer 34 and the cap layer 12a. A pinning layer 32 is further provided between the upper pinned layer 33 and the cap layer 12ac. The configuration described in regard to the first magnetic layer 11a may be used for the upper pinned layer 33. The extending direction of the upper pinned layer 33 crosses the extending direction of the first magnetic layer 11a. The extending direction of the upper pinned layer 33 may run along or cross the extending direction of the second magnetic layer 12a. In the pressure sensor of this example, the configuration of a magnetization fixed layer/an intermediate layer/a magnetization free layer/an intermediate layer/a magnetization fixed layer is used, for example. The configuration may be called a dual spin valve type, for example.

In the configurations illustrated in FIG. 24A to FIG. 24C, the insulating layer 11i may be further provided.

The pinning layer 32 provides unidirectional anisotropy to the second magnetic layer 12a (a ferromagnetic layer) in contact with the pinning layer 32, and fixes the magnetization of the second magnetic layer 12a, for example. An antiferromagnetic layer is used as the pinning layer 32, for example. At least one selected from the group consisting of IrMn, PtMn, PdPtMn, and RuRhMn is used for the pinning layer 32, for example. The thickness of the pinning layer 32 is appropriately adjusted to provide unidirectional anisotropy of a sufficient strength.

When PtMn or PdPtMn is used as the pinning layer 32, the thickness of the pinning layer 32 is preferably not less than 8 nm and not more than 20 nm. The thickness of the pinning layer 32 is more preferably not less than 10 nm and not more than 15 nm. When IrMn is used as the pinning layer 32, unidirectional anisotropy can be provided by a smaller thickness than when PtMn is used as the pinning layer 32. In this case, the thickness of the pinning layer 32 is preferably not less than 4 nm and not more than 18 nm. The thickness of the pinning layer 32 is more preferably not less than 5 nm and not more than 15 nm. An $Ir_{22}Mn_{78}$ layer with a thickness of 7 nm is used as the pinning layer 32, for example.

A hard magnetic layer may be used as the pinning layer 32. As the hard magnetic layer, CoPt (the ratio of Co being not less than 50 at. % (atomic percent) and not more than 85 at. %), $(Co_xPt_{100-x})_{100-y}Cr_y$ (x being not less than 50 at. % and not more than 85 at. %, y being not less than 0 at. % and not more than 40 at. %), FePt (the ratio of Pt being not less than 40 at. % and not more than 60 at. %), or the like may be used, for example.

In the case where a magnetization fixed layer is used as the second magnetic layer 12a, a ferromagnetic material containing at least one element selected from the group consisting of Fe, Co, and Ni may be used for the second magnetic layer 12a. As the material of the first magnetic layer 11a, FeCo alloy and NiFe alloy may be used, for example. For the first magnetic layer 11a, an alloy containing at least one element selected from the group consisting of Fe, Co, and Ni and boron (B) may be used. For the second magnetic layer 12a, Co—Fe—B alloy, Fe—B alloy, Fe—Co—Si—B alloy, or the like may be used, for example. As the second magnetic layer 12a, a $Co_{40}Fe_{40}B_{20}$ layer (the thickness being 4 nm, for example) may be used, for example.

In the case where a magnetization fixed layer is used as the second magnetic layer 12a, a stacked structure of a pinning layer-side magnetization fixed layer/a magnetic coupling layer/an intermediate layer-side magnetization fixed layer may be used as the second magnetic layer 12a. The pinning layer-side magnetization fixed layer is disposed in contact with the pinning layer 32. The intermediate layer-side magnetization fixed layer is disposed in contact with the intermediate layer (the first intermediate layer 13a). Such magnetization fixed layers are called a synthetic pin structure.

As the pinning layer-side magnetization fixed layer, $Co_xFe_{100-x}$ alloy (x being not less than 0 at. % and not more than 100 at. %), $Ni_xFe_{100-x}$ alloy (x being not less than 0 at. % and not more than 100 at. %), or a material in which a nonmagnetic element is added to these is used, for example. As the pinning layer-side magnetization fixed layer, at least one selected from the group consisting of Co, Fe, and Ni is used, for example. As the second magnetization fixed layer, an alloy containing at least one material selected from these materials may be used. As the pinning layer-side magnetization fixed layer, $(Co_xFe_{100-x})_{100-y}B_y$ alloy (x being not less than 0 at. % and not more than 100 at. %, y being not less than 0 at. % and not more than 30 at. %) may be used.

The thickness of the pinning layer-side magnetization fixed layer is preferably not less than 1.5 nm and not more than 5 nm, for example. Thereby, the strength of the unidirectional anisotropic magnetic field caused by the pinning layer 32 can be increased, for example. The strength of the antiferromagnetic coupling magnetic field between the pinning layer-side magnetization fixed layer and the intermediate layer-side magnetization fixed layer can be increased via a magnetic coupling layer formed in contact with the pinning layer-side magnetization fixed layer, for example. The magnetic thickness (the product of the saturation magnetization Bs and the thickness t (Bs·t)) of the pinning layer-side magnetization fixed layer is preferably substantially equal to the magnetic thickness of the intermediate layer-side magnetization fixed layer, for example.

The saturation magnetization of $Co_{40}Fe_{40}B_{20}$ in a thin film form is approximately 1.9 T (tesla). When a $Co_{40}Fe_{40}B_{20}$ layer with a thickness of 3 nm is used as the intermediate layer-side magnetization fixed layer, the magnetic thickness of the intermediate layer-side magnetization fixed layer is 1.9 T×3 nm, which is 5.7 Tnm, for example. On the other hand, the saturation magnetization of $Co_{75}Fe_{25}$ is approximately 2.1 T. The thickness of the pinning layer-side magnetization fixed layer by which a magnetic thickness equal to the above is obtained is 5.7 Tnm/2.1 T, which is 2.7 nm. In this case, a $Co_{75}Fe_{25}$ layer with a thickness of approximately 2.7 nm is preferably used as the pinning layer-side magnetization fixed layer. A $Co_{75}Fe_{25}$ layer with a thickness of 2.5 nm is used as the pinning layer-side magnetization fixed layer, for example.

The magnetic coupling layer produces an antiferromagnetic coupling between the pinning layer-side magnetization fixed layer and the intermediate layer-side magnetization fixed layer. The magnetic coupling layer forms a synthetic pin structure. Ru is used as the magnetic coupling layer, for example. The thickness of the magnetic coupling layer is preferably not less than 0.8 nm and not more than 1 nm, for example. Other materials than Ru may be used as the magnetic coupling layer to the extent that they produce a sufficient antiferromagnetic coupling between the pinning layer-side magnetization fixed layer and the intermediate layer-side magnetization fixed layer. The thickness of the magnetic coupling layer may be set to a thickness of not less than 0.8 nm and not more than 1 nm corresponding to the second peak (2nd peak) of the RKKY (Ruderman-Kittel-Kasuya-Yosida) coupling. The thickness of the magnetic coupling layer may be set to a thickness of not less than 0.3 nm and not more than 0.6 nm corresponding to the first peak (1st peak) of the RKKY coupling. Ru with a thickness of 0.9 nm is used as the magnetic coupling layer, for example. Thereby, a highly reliable coupling is obtained more stably.

The magnetic layer used as the intermediate layer-side magnetization fixed layer directly contributes to the MR effect. Co—Fe—B alloy is used as the intermediate layer-side magnetization fixed layer, for example. Specifically, $(Co_xFe_{100-x})_{100-y}B_y$ alloy (x being not less than 0 at. % and not more than 100 at. %, y being not less than 0 at. % and not more than 30 at. %) may be used as the intermediate layer-side magnetization fixed layer.

A layer (for example a tunnel insulating layer (not shown)) formed on the intermediate layer-side magnetization fixed layer may be planarized. By the planarization of the tunnel insulating layer, the defect density of the tunnel insulating layer can be reduced. Thereby, a larger MR ratio is obtained with a lower resistance area. When MgO is used as the material of the tunnel insulating layer, an amorphous alloy of $(Co_xFe_{100-x})_{100-y}B_y$ may be used as the intermediate layer-side magnetization fixed layer; thereby, the (100) orientation properties of the MgO layer formed on the tunnel insulating layer can be enhanced, for example. By enhancing the (100) orientation properties of the MgO layer, a larger MR ratio is obtained. The $(Co_xFe_{100-x})_{100-y}B_y$ alloy is crystallized during annealing, with the (100) plane of the MgO layer as a template. Thus, good crystal matching between the MgO and the $(Co_xFe_{100-x})_{100-y}B_y$ alloy is obtained. By obtaining good crystal matching, a larger MR ratio is obtained.

As the intermediate layer-side magnetization fixed layer, Fe—Co alloy may be used as well as Co—Fe—B alloy, for example.

When the intermediate layer-side magnetization fixed layer is thicker, a larger MR ratio is obtained. To obtain a larger fixed magnetic field, the intermediate layer-side magnetization fixed layer is preferably thinner. Between the MR ratio and the fixed magnetic field, there is a trade-off in the thickness of the intermediate layer-side magnetization fixed layer. When Co—Fe—B alloy is used as the intermediate layer-side magnetization fixed layer, the thickness of the intermediate layer-side magnetization fixed layer is preferably not less than 1.5 nm and not more than 5 nm. The thickness of the intermediate layer-side magnetization fixed layer is more preferably not less than 2.0 nm and not more than 4 nm.

For the intermediate layer-side magnetization fixed layer, $Co_{90}Fe_{10}$ alloy of the fcc structure, Co of the hcp structure, or a Co alloy of the hcp structure is used as well as the material described above. As the intermediate layer-side magnetization fixed layer, at least one selected from the group consisting of Co, Fe, and Ni is used, for example. As the intermediate layer-side magnetization fixed layer, an alloy containing at least one material selected from these materials is used. As the intermediate layer-side magnetization fixed layer, an FeCo alloy material of the bcc structure, a Co alloy with a cobalt content of 50 at. % or more, a material with a Ni content of 50 at. % or more (a Ni alloy) may be used; thereby, a larger MR ratio is obtained, for example.

As the intermediate layer-side magnetization fixed layer, a Heusler magnetic alloy layer of $Co_2MnGe$, $Co_2FeGe$, $Co_2MnSi$, $Co_2FeSi$, $Co_2MnAl$, $Co_2FeAl$, $Co_2MnGa_{0.5}Ge_{0.5}$, $Co_2FeGa_{0.5}Ge_{0.5}$, and the like may be used, for example. As the intermediate layer-side magnetization fixed layer, a $Co_{40}Fe_{40}B_{20}$ layer with a thickness of 3 nm is used, for example.

For the pinning layer 31, the material and configuration described in regard to the pinning layer 32 may be used. For the other layers, materials substantially the same as the material illustrated in regard to FIG. 3A may be used. For the upper pinned layer 33, the material and configuration described above when a magnetization fixed layer is used as the second magnetic layer 12a may be used. For the upper intermediate layer 34, the material and configuration described in regard to the first intermediate layer 13a may be used, for example.

FIG. 25A to FIG. 25D are schematic diagrams illustrating the pressure sensor according to the first embodiment.

The drawings illustrate operations of the sensing element 50 (the first sensing element 50a) of the examples shown FIG. 24A and FIG. 24B. FIG. 25A corresponds to a state where no strain is generated in the first sensing element 50a (the no-strain state ST0). FIG. 25B corresponds to a state where a compressive strain is generated in the first sensing element 50a (the first state ST1). FIG. 25C corresponds to a state where a tensile strain is generated in the first sensing element 50a (the second state ST2). In these drawings, for easier viewing of the drawings, the first magnetic layer 11a and the second magnetic layer 12a are depicted, and the first intermediate unit 13au is omitted.

FIG. 25D illustrates the relationship between the strain Sa generated in the first sensing element 50a and the electric resistance R (Ω) of the first sensing element 50a. The electric resistance R is the electric resistance between the first magnetic layer 11a and the second magnetic layer 12a.

As shown in FIG. 25A, in the no-strain state ST0, the magnetization 11am of the first magnetic layer 11a that is a magnetization free layer is set along the first direction X1 in which the first magnetic layer 11a extends. This is due to the shape magnetic anisotropy mentioned above. In the no-strain state ST0, the magnetization 12am of the second magnetic layer 12a that is a magnetization fixed layer can be fixed to run along the second direction X2 in which the second magnetic layer 12a extends. It is assumed that, immediately after the film formation of a stacked body that forms the sensing element, an exchange coupling from the pinning layer 32 is not made on the second magnetic layer 12a, for example. Setting the second magnetic layer 12a to a state of being a magnetization free layer, the planar shape of the second magnetic layer 12a is processed into a shape having shape anisotropy. Thereby, the magnetization 12am of the second magnetic layer 12a becomes a state of running along the second direction X2. In this state, heat treatment is performed in no magnetic field. Thereby, after cooling after the heat treatment, the magnetization 12am of the second magnetic layer 12a can be fixed to run along the second direction X2 as it is.

By changing the angle between the first direction X1 in which the first magnetic layer 11a extends and the second direction X2 in which the second magnetic layer 12a extends, the relative angle between the direction of the magnetization 11am of the first magnetic layer 11a and the direction of the magnetization 12am of the second magnetic layer 12a can be set arbitrarily.

As shown in FIG. 25B, in the first state ST1 where a compressive strain CS is generated, the angle between the magnetization 11am of the first magnetic layer 11a and the magnetization 12am of the second magnetic layer 12a is larger than the angle in the no-strain state ST0, for example. The electric resistance R changes in conjunction with this.

As shown in FIG. 25C, in the second state ST2 where a tensile strain TS is generated, the angle between the magnetization 11am of the first magnetic layer 11a and the magnetization 12am of the second magnetic layer 12a is smaller than the angle in the no-strain state ST0, for example. The electric resistance R changes in conjunction with this.

As shown in FIG. 25D, when a compressive strain CS is generated, the electric resistance R of the first sensing element 50a is increased as compared to the no-strain state ST0. When a tensile strain TS is generated, the electric resistance R of the first sensing element 50a is decreased as compared to the no-strain state ST0.

In this way, the first sensing element 50a can convert the change in strain Sa generated in the first sensing element 50a to a change in electric resistance R.

As illustrated in FIG. 25A, in the first sensing element 50a, in the no-strain state ST0, the magnetization of the second magnetic layer that is a magnetization fixed layer and the magnetization of the first magnetic layer that is a magnetization free layer can be directed to directions different from each other. Thereby, as illustrated in FIG. 25D, the electric resistance R changes linearly with respect to the tensile and compressive strain Sa, for example. Thereby, a high-sensitivity pressure sensor can be provided.

The configuration, the direction of the magnetization 11a of the first magnetic layer 11, and the direction of the magnetization 12am of the second magnetic layer 12a described in FIG. 5 to FIG. 23E may be used in the examples described in regard to FIG. 24A to FIG. 25D.

Figure 26A:
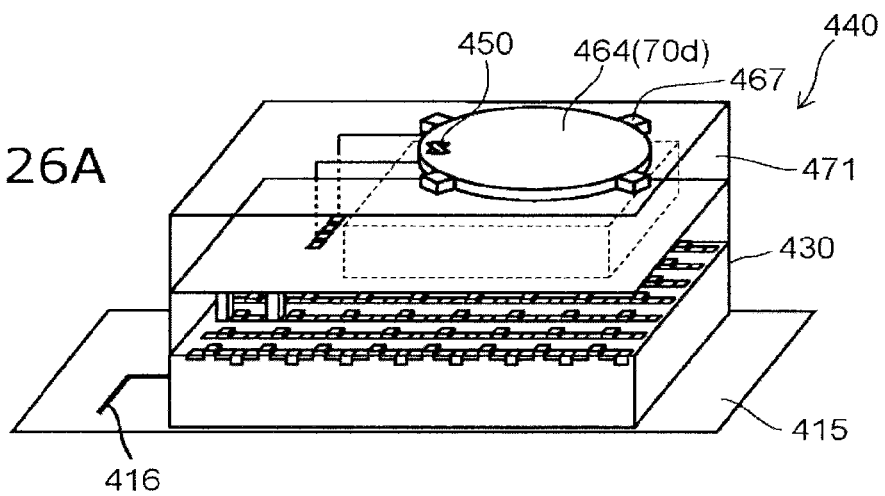
FIG. 26A to FIG. 26C are schematic diagrams showing a pressure sensor according to the first embodiment.
Figure 26B:
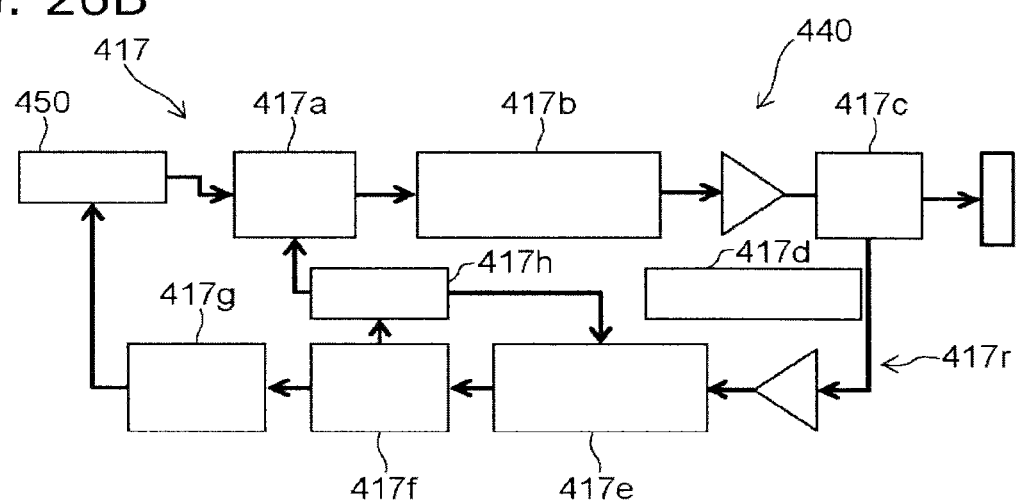
Figure 26C:
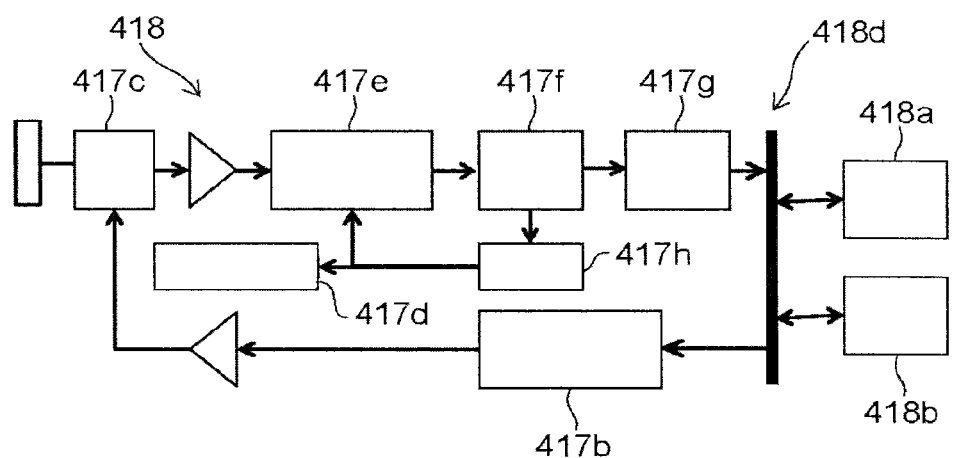

FIG. 26A to FIG. 26C are schematic diagrams illustrating a pressure sensor according to the first embodiment.

FIG. 26A is a schematic perspective view, and FIG. 26B and FIG. 26C are block diagrams illustrating a pressure sensor 440.

As shown in FIG. 26A and FIG. 26B, in the pressure sensor 440, a base 471, a sensing unit 450, a semiconductor circuit unit 430, an antenna 415, an electric interconnection 416, a transmitting circuit 417, and a receiving circuit 417r are provided.

The antenna 415 is electrically connected to the semiconductor circuit unit 430 via the electric interconnection 416.

The transmitting circuit 417 transmits data based on an electric signal traveling through the sensing unit 450 wirelessly. At least part of the transmitting circuit 417 may be provided in the semiconductor circuit unit 430.

The receiving circuit 417r receives a control signal from an electronic device 418d. At least part of the receiving circuit 417r may be provided in the semiconductor circuit unit 430. By providing the receiving circuit 417r, the operation of the pressure sensor 440 can be controlled by operating the electronic device 418d, for example.

As shown in FIG. 26B, in the transmitting circuit 417, an A/D converter 417a connected to the sensing unit 450 and a Manchester encoding unit 417b may be provided, for example. A switching unit 417c may be provided to switch between transmission and reception. In this case, a timing controller 417d may be provided, and switching in the switching unit 417c can be controlled by the timing controller 417d. A data correction unit 417e, a synchronization unit 417f, a determination unit 417g, and a voltage-controlled oscillator 417h (VCO) may be further provided.

As shown in FIG. 26C, a receiving unit 418 is provided in the electronic device 418d used in combination with the pressure sensor 440. As the electronic device 418d, an electronic device such as a mobile terminal may be given, for example.

In this case, the pressure sensor 440 including the transmitting circuit 417 and the electronic device 418d including the receiving unit 418 may be used in combination.

In the electronic device 418d, a Manchester encoding unit 417b, a switching unit 417c, a timing controller 417d, a data correction unit 417e, a synchronization unit 417f, a determination unit 417g, a voltage-controlled oscillator 417h, a memory unit 418a, and a central processing unit 418b (CPU) may be provided.

In this example, the pressure sensor 440 further includes a fixing unit 467. The fixing unit 467 fixes a film unit 464 (70d) to the base 471. The fixing unit 467 may have a larger thickness dimension than the film unit 464 so as to bend less easily even when an external pressure is applied.

Fixing units 467 may be provided at equal intervals at the edge of the film unit 464, for example.

The fixing unit 467 may be provided so as to continuously surround the entire periphery of the film unit 464 (70d).

The fixing unit 467 may be formed of the same material as the material of the base 471, for example. In this case, the fixing unit 467 may be formed of silicon or the like, for example.

The fixing unit 467 may be formed of the same material as the material of the film unit 464 (70d), for example.

A method for manufacturing a pressure sensor according to the embodiment will now be described.

FIG. 27A, FIG. 27B, FIG. 28A, FIG. 28B, FIG. 29A, FIG. 29B, FIG. 30A, FIG. 30B, FIG. 31A, FIG. 31B, FIG. 32A, FIG. 32B, FIG. 33A, FIG. 33B, FIG. 34A, FIG. 34B, FIG. 35A, FIG. 35B, FIG. 36A, FIG. 36B, FIG. 37A, FIG. 37B, FIG. 38A, and FIG. 38B are schematic views illustrating a method for manufacturing a pressure sensor according to a third embodiment.

FIG. 27A to FIG. 38A are schematic plan views, and FIG. 27B to FIG. 38B are schematic cross-sectional views.

Figure 27A:
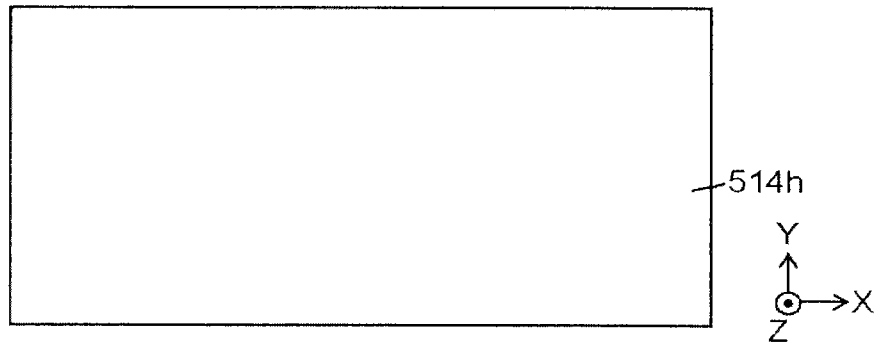
FIG. 27A and FIG. 27B are schematic views showing a method for manufacturing a pressure sensor according to a third embodiment.
Figure 27B:
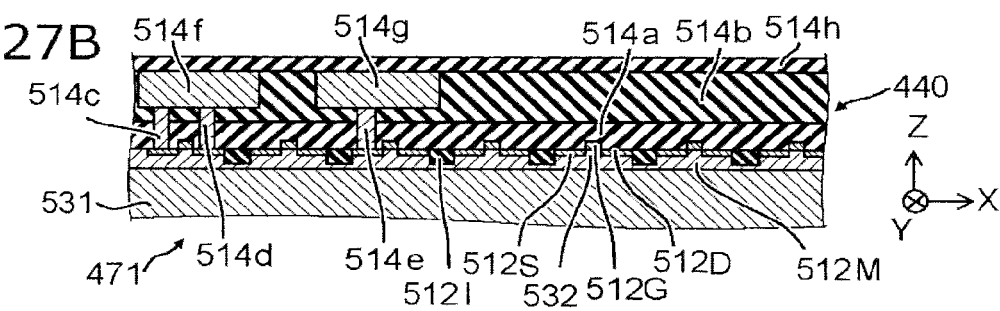

As shown in FIG. 27A and FIG. 27B, a semiconductor layer 512M is formed on a surface portion of a semiconductor substrate 531. Subsequently, an element isolation insulating layer 512I is formed on the upper surface of the semiconductor layer 512M. Subsequently, a gate 512G is formed on the semiconductor layer 512M via a not-shown insulating layer. Subsequently, a source 512S and a drain 512D are formed on both sides of the gate 512G to form a transistor 532. Subsequently, an interlayer insulating film 514a is formed thereon, and an interlayer insulating film 514b is formed.

Subsequently, in the region that forms a non-hollow portion, trenches and holes are formed in parts of the interlayer insulating films 514a and 514b. Subsequently, a conductive material is buried in the holes to form connection pillars 514c to 514e. In this case, the connection pillar 514c is electrically connected to the source 512S of a transistor 532, and the connection pillar 514d is electrically connected to the drain 512D, for example. The connection pillar 514e is electrically connected to the source 512S of another transistor 532, for example. Subsequently, a conductive material is buried in the trenches to form interconnection units 514f and 514g. The interconnection unit 514f is electrically connected to the connection pillar 514c and the connection pillar 514d. The interconnection unit 514g is electrically connected to the connection pillar 514e. Subsequently, an interlayer insulating film 514h is formed on the interlayer insulating film 514b.

Figure 28A:
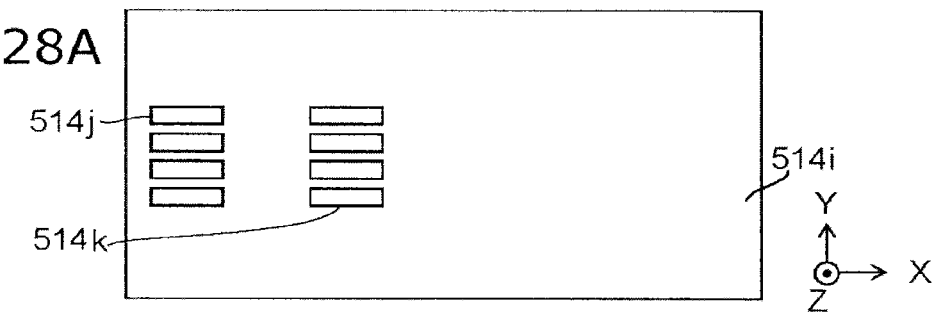
FIG. 28A and FIG. 28B are schematic views showing a method for manufacturing a pressure sensor according to a third embodiment.
Figure 28B:
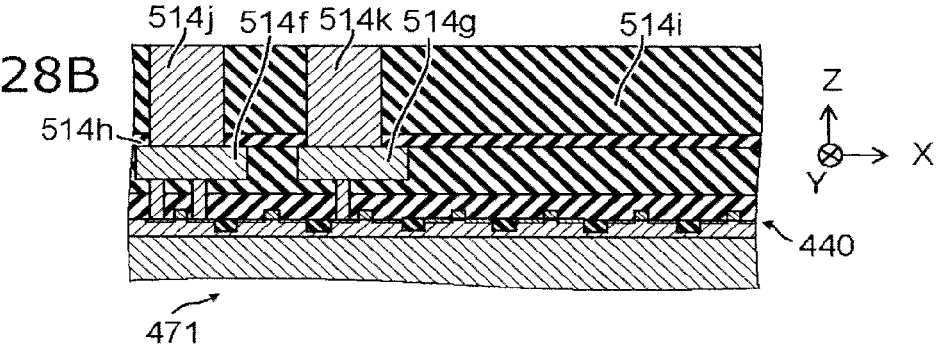

As shown in FIG. 28A and FIG. 28B, an interlayer insulating film 514i made of silicon oxide (SiO$_2$) is formed on the interlayer insulating film 514h using the CVD (chemical vapor deposition) method, for example. Subsequently, holes are formed in prescribed positions of the interlayer insulating film 514i, a conductive material (for example, a metal material) is buried, and the upper surface is planarized using the CMP (chemical mechanical polishing) method. Thereby, a connection pillar 514j connected to the interconnection unit 514f and a connection pillar 514k connected to the interconnection unit 514g are formed.

Figure 29A:
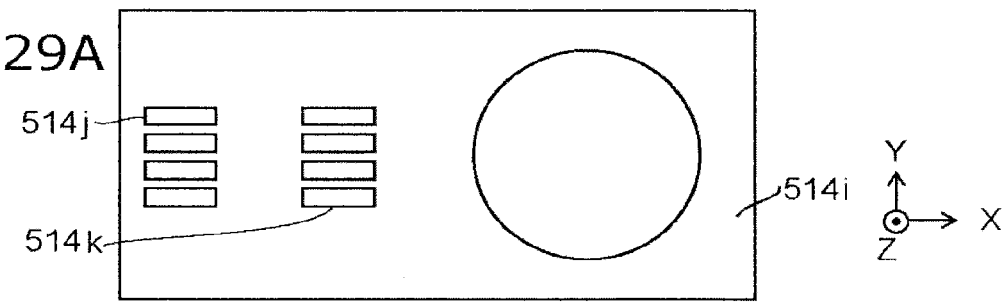
FIG. 29A and FIG. 29B are schematic views showing a method for manufacturing a pressure sensor according to a third embodiment.
Figure 29B:
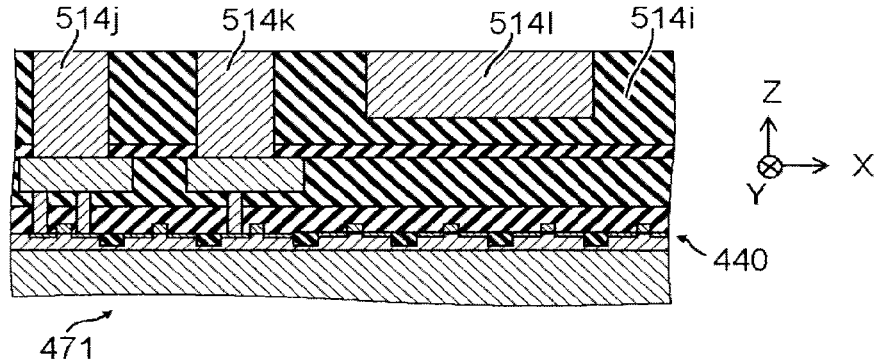

As shown in FIG. 29A and FIG. 29B, a recess is formed in a region of the interlayer insulating film 514i that forms a hollow portion 570, and a sacrifice layer 514l is buried in the recess. The sacrifice layer 514l may be formed using a material that can be formed into a film at low temperature, for example. The material that can be made into a film at low temperature is silicon germanium (SiGe) or the like, for example.

Figure 30A:
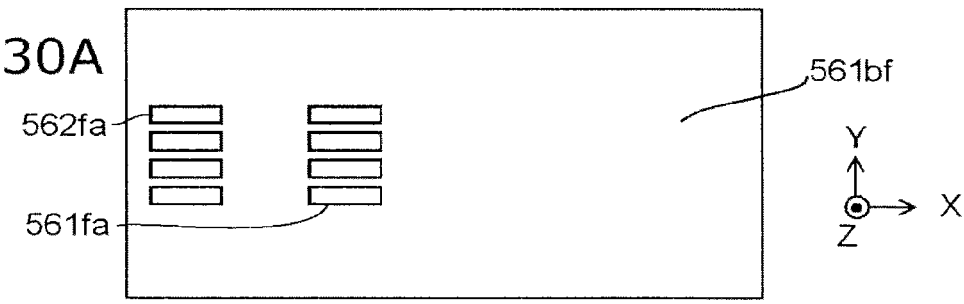
FIG. 30A and FIG. 30B are schematic views showing a method for manufacturing a pressure sensor according to a third embodiment.
Figure 30B:
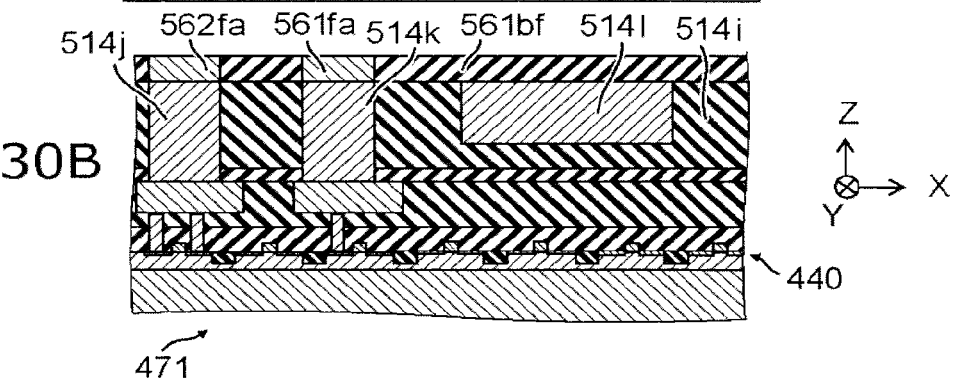

As shown in FIG. 30A and FIG. 30B, an insulating film 561bf that forms a film unit 564 (70d) is formed on the interlayer insulating film 514i and the sacrifice layer 514l. The insulating film 561bf may be formed using silicon oxide (SiO$_2$) or the like, for example. A plurality of holes are provided in the insulating film 561bf, and a conductive material (for example, a metal material) is buried in the plurality of holes to form a connection pillar 561fa and a connection pillar 562fa. The connection pillar 561fa is electrically connected to the connection pillar 514k, and the connection pillar 562fa is electrically connected to the connection pillar 514j.

Figure 31A:
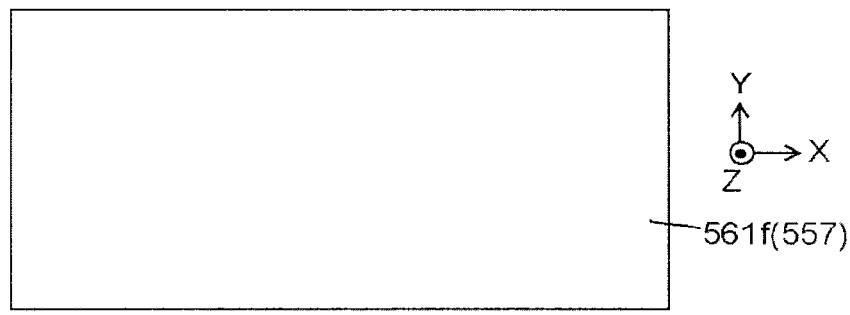
FIG. 31A and FIG. 31B are schematic views showing a method for manufacturing a pressure sensor according to a third embodiment.
Figure 31B:
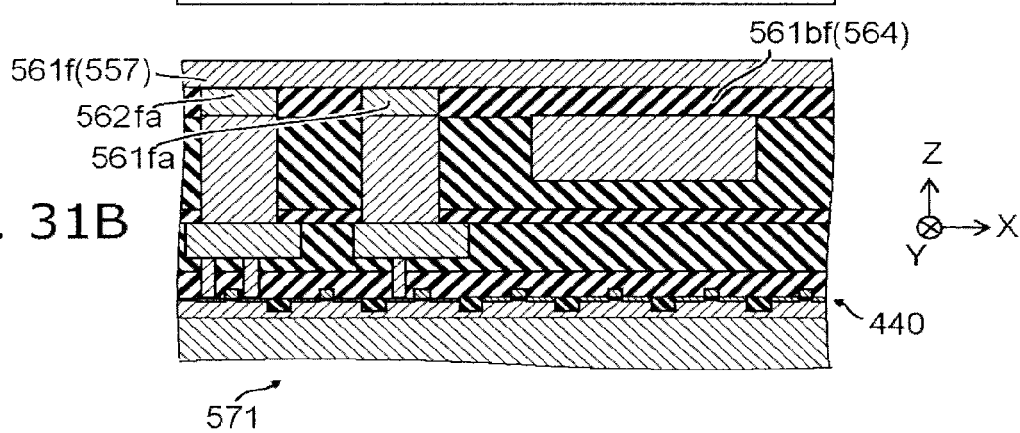

As shown in FIG. 31A and FIG. 31B, a conductive layer 561f that forms an interconnection 557 is formed on the insulating film 561bf, the connection pillar 561fa, and the connection pillar 562fa.

Figure 32A:
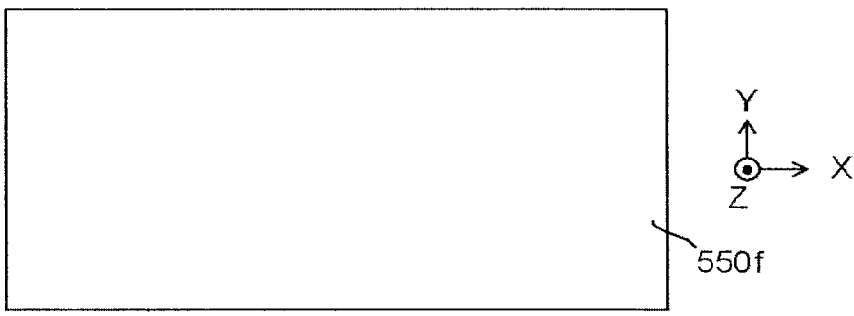
FIG. 32A and FIG. 32B are schematic views showing a method for manufacturing a pressure sensor according to a third embodiment.
Figure 32B:
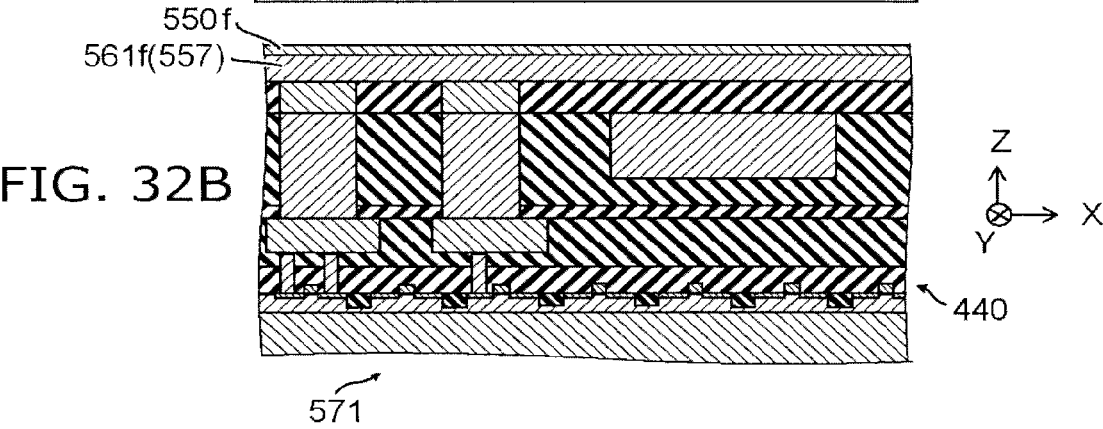
Figure 33A:
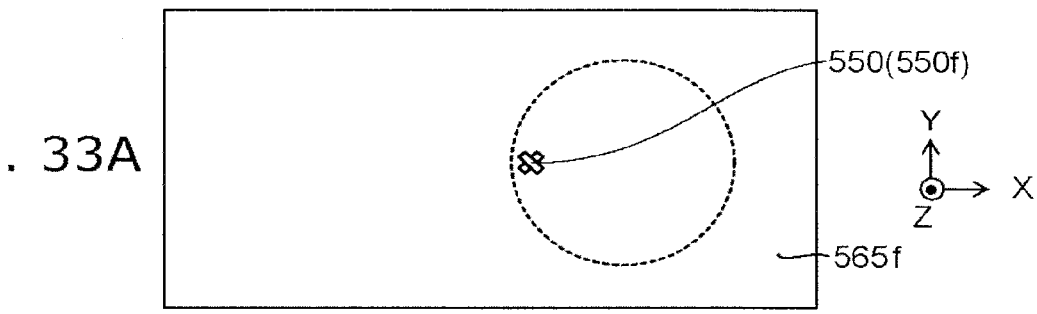
FIG. 33A and FIG. 33B are schematic views showing a method for manufacturing a pressure sensor according to a third embodiment.
Figure 33B:
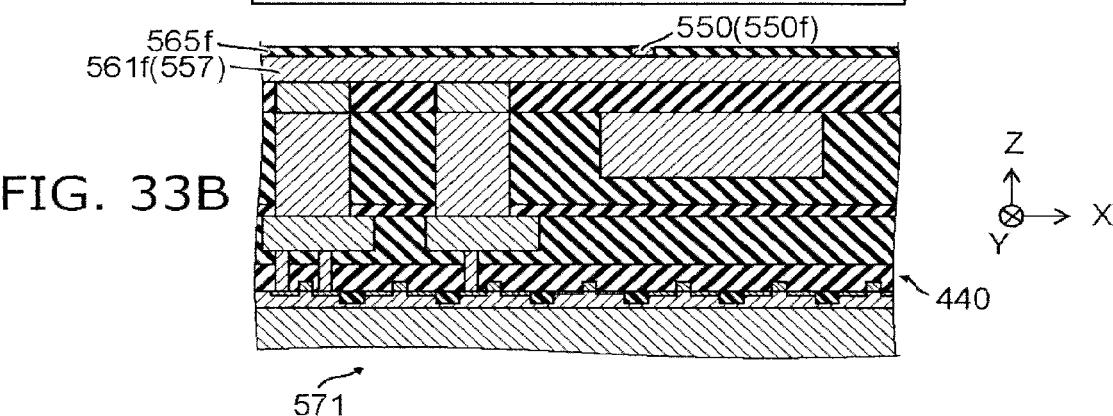

As shown in FIG. 32A and FIG. 33B, a stacked film 550f is formed on the conductive layer 561f.

As shown in FIG. 33A and FIG. 33B, the stacked film 550f is processed into a prescribed shape, and an insulating film 565f that forms an insulating layer 565 is formed thereon. The insulating film 565f may be formed using silicon oxide (SiO$_2$) or the like, for example.

Figure 34A:
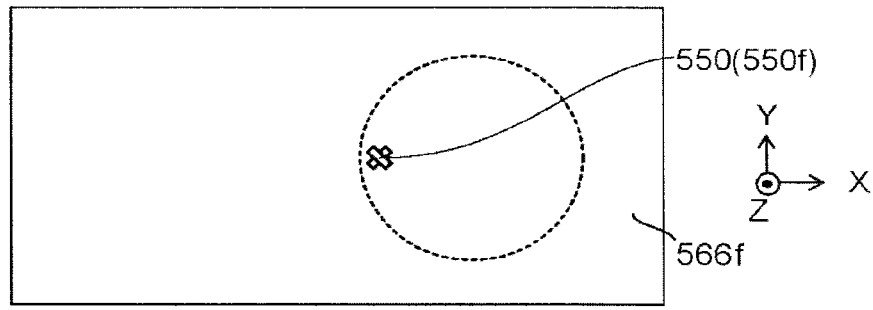
FIG. 34A and FIG. 34B are schematic views showing a method for manufacturing a pressure sensor according to a third embodiment.
Figure 34B:
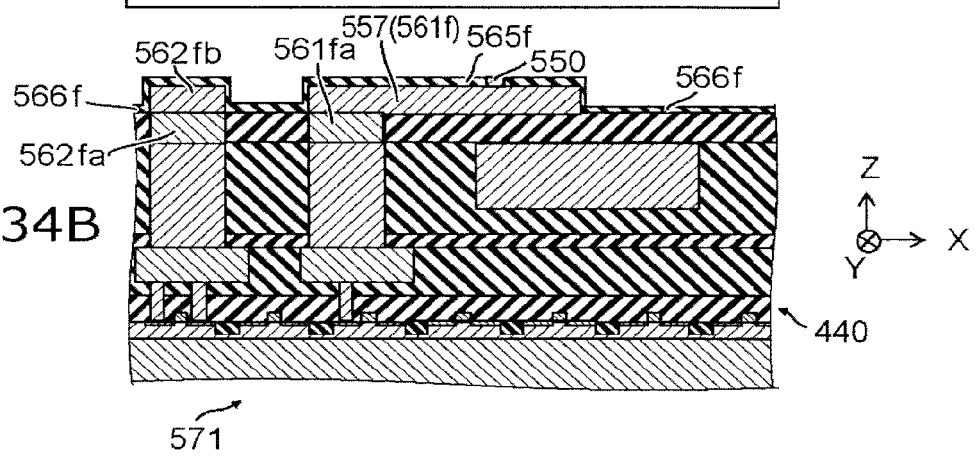

As shown in FIG. 34A and FIG. 34B, part of the insulating film 565f is removed, and the conductive layer 561f is processed into a prescribed shape. Thereby, an interconnection 557 is formed. At this time, part of the conductive layer 561f forms a connection pillar 562fb electrically connected to the connection pillar 562fa. Then, an insulating film 566f that forms an insulating layer 566 is formed thereon.

As shown in FIG. 35A and FIG. 35B, an opening 566p is formed in the insulating film 566f. Thereby, the connection pillar 562fb is exposed.

Figure 37A:
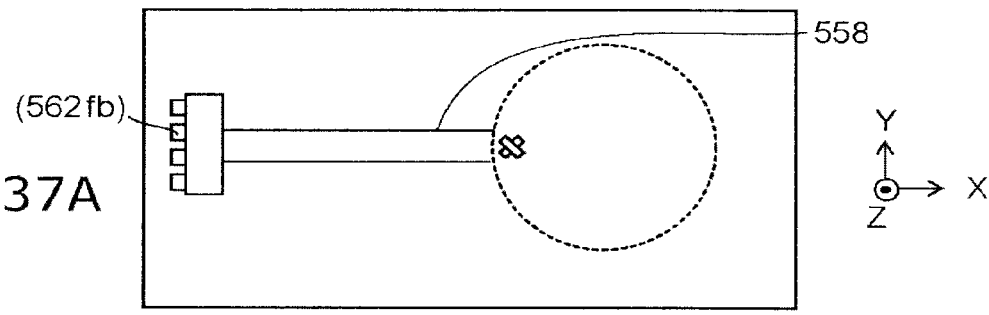
FIG. 37A and FIG. 37B are schematic views showing a method for manufacturing a pressure sensor according to a third embodiment.
Figure 37B:
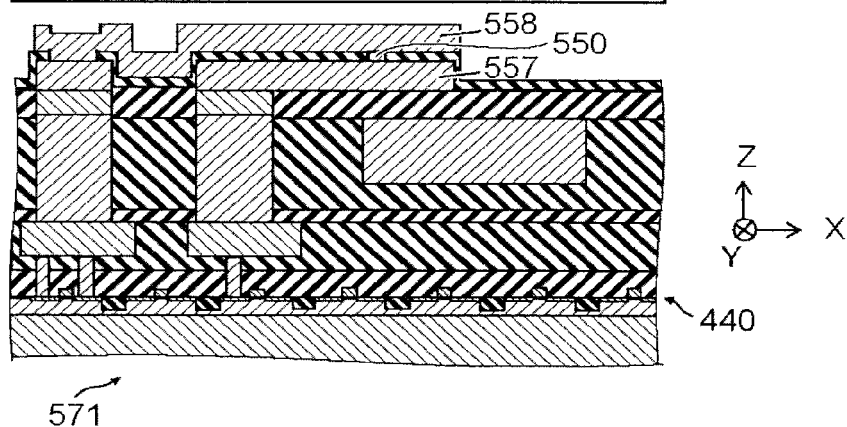

As shown in FIG. 36A and FIG. 36B, a conductive layer 562f that forms an interconnection 558 is formed on the upper surface. Part of the conductive layer 562f is electrically connected to the connection pillar 562fb. As shown in FIG. 37A and FIG. 37B, the conductive layer 562f is processed into a prescribed shape. Thereby, an interconnection 558 is formed. The interconnection 558 is electrically connected to the connection pillar 562fb.

Figure 38A:
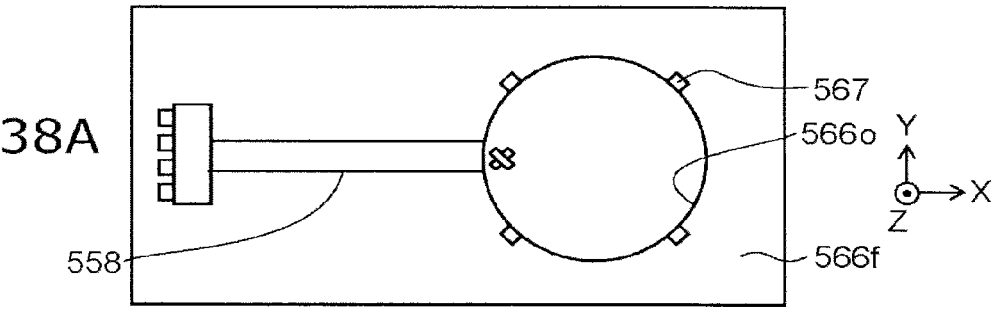
FIG. 38A and FIG. 38B are schematic views showing a method for manufacturing a pressure sensor according to a third embodiment.
Figure 38B:
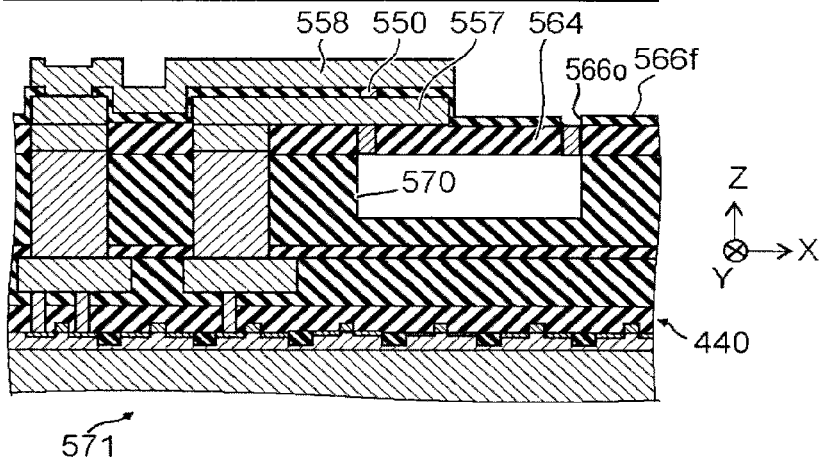

As shown in FIG. 38A and FIG. 38B, an opening 566o with a prescribed shape is formed in the insulating film 566f. The insulating film 561bf is processed via the opening 566o, and the sacrifice layer 514l is removed via the opening 566o. Thereby, a hollow portion 570 is formed. The removal of the sacrifice layer 514l can be performed using the wet etching method, for example.

When a fixing unit 567 is shaped like a ring, the space between the edge of the non-hollow portion above the hollow portion 570 and the film unit 564 is filled with an insulating film, for example.

Thus, a pressure sensor is formed.

Second Embodiment

The embodiment relates to a microphone using the pressure sensor according to the first embodiment.

Figure 39:
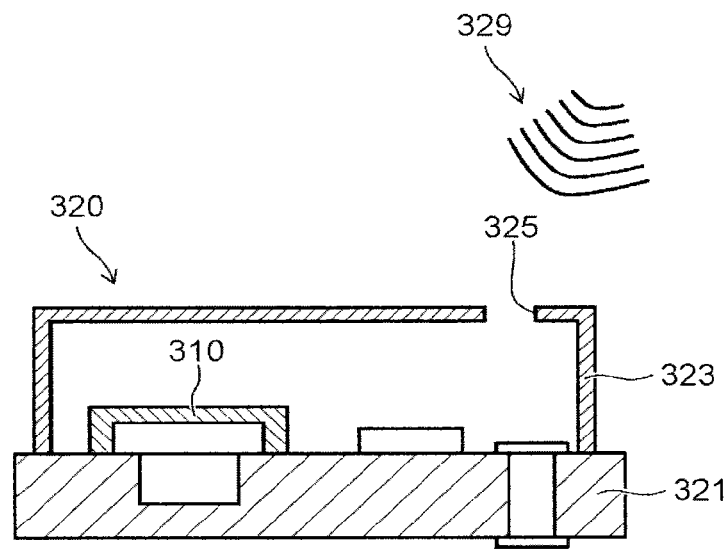
FIG. 39 is a schematic cross-sectional view showing a microphone according to a second embodiment.

FIG. 39 is a schematic cross-sectional view illustrating a microphone according to a second embodiment.

A microphone 320 according to the embodiment includes a printed circuit board 321, a cover 323, and a pressure sensor 310. The printed circuit board 321 includes a circuit of an amplifier etc., for example. An acoustic hole 325 is provided in the cover 323. Sound 329 passes through the acoustic hole 325 to enter the inside of the cover 323.

As the pressure sensor 310, any one of the pressure sensors described in regard to the first embodiment or modifications thereof are used.

The microphone 320 reacts to sound pressure. By using a high-sensitivity pressure sensor 310, a high-sensitivity microphone 320 is obtained. The pressure sensor 310 is mounted on the printed circuit board 321, and an electric signal device is provided, for example. The cover 323 is provided on the printed circuit board 321 so as to cover the pressure sensor 310.

The embodiment can provide a high-sensitivity microphone.

Third Embodiment

The embodiment relates to a blood pressure sensor using the pressure sensor according to the first embodiment.

Figure 40A:
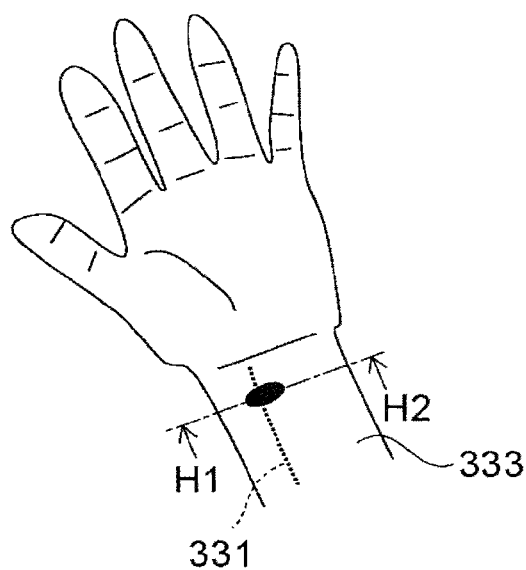
FIG. 40A and FIG. 40B are schematic views showing a blood pressure sensor according to a third embodiment.
Figure 40B:
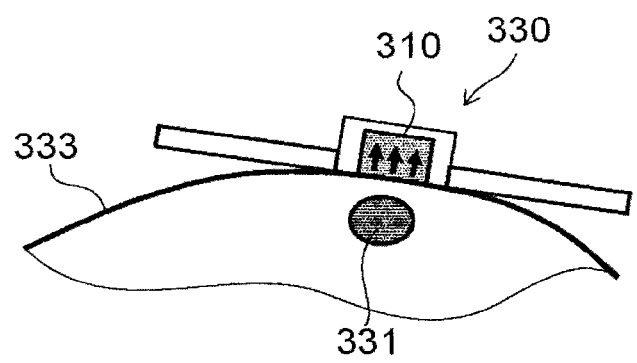

FIG. 40A and FIG. 40B are schematic views illustrating a blood pressure sensor according to a third embodiment.

FIG. 40A is a schematic plan view illustrating the skin on an artery of a person. FIG. 40B is a cross-sectional view taken along line H1-H2 of FIG. 40A.

In the embodiment, the pressure sensor 310 is used as a blood pressure sensor 330. Any one of the pressure sensors described in regard to the first embodiment and modifications thereof are used as the pressure sensor 310.

Thus, high-sensitivity pressure sensing can be made by a small-sized pressure sensor. By pressing the pressure sensor 310 against the skin 333 on an artery 331, the blood pressure sensor 330 can make blood pressure measurement continuously.

The embodiment can provide a high-sensitivity blood pressure sensor.

Fourth Embodiment

The embodiment relates to a touch panel using the pressure sensor according to the first embodiment.

Figure 41:
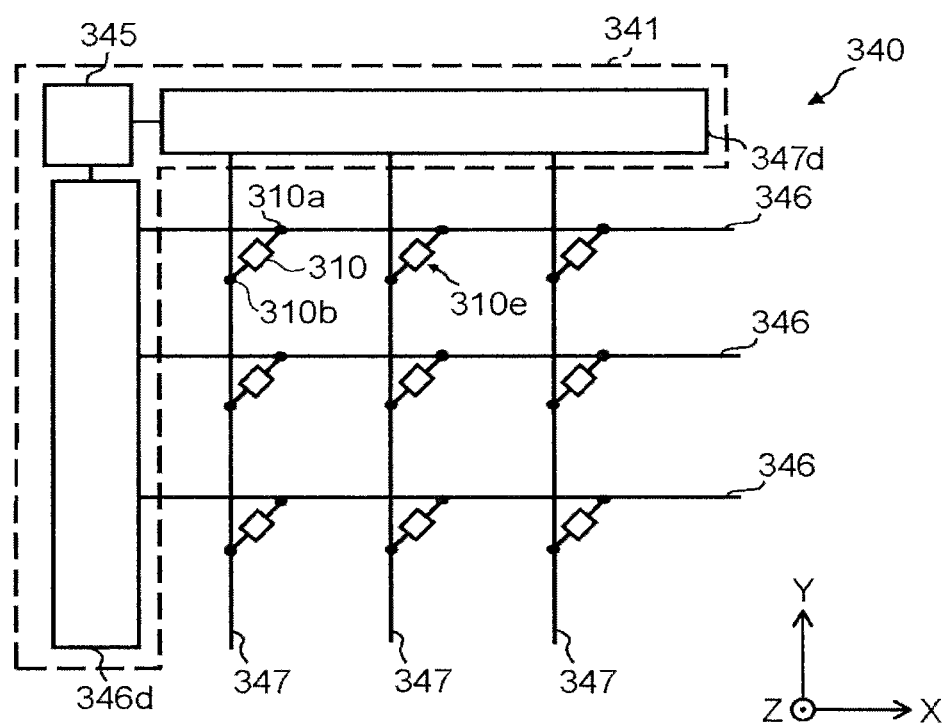
FIG. 41 is a schematic diagram showing a touch panel according to a fourth embodiment.

FIG. 41 is a schematic diagram illustrating a touch panel according to a fourth embodiment.

In the embodiment, the pressure sensor 310 is used as a touch panel 340. Any one of the pressure sensors described in regard to the first embodiment or modifications thereof are used as the pressure sensor 310. In the touch panel 340, the pressure sensor 310 is mounted at least one of in a display and outside a display.

The touch panel 340 includes a plurality of first interconnections 346, a plurality of second interconnections 347, a plurality of pressure sensors 310, and a control unit 341, for example.

In this example, the plurality of first interconnections 346 are aligned along the Y-axis direction. Each of the plurality of first interconnections 346 extends along the X-axis direction. The plurality of second interconnections 347 are aligned along the X-axis direction. Each of the plurality of second interconnections 347 extends along the Y-axis direction.

Each of the plurality of pressure sensors 310 is provided in the intersection portion of each of the plurality of first interconnections 346 and each of the plurality of second interconnections 347. One pressure sensor 310 is included in one sensing element 310e for detection. The intersection portion includes the position where the first interconnection 346 and the second interconnection 347 cross each other and a region around this.

One end 310a of each of the plurality of pressure sensors 310 is connected to each of the plurality of first interconnections 346. The other end 310b of each of the plurality of pressure sensors 310 is connected to each of the plurality of second interconnections 347.

The control unit 341 is connected to the plurality of first interconnections 346 and the plurality of second interconnections 347.

The control unit 341 includes a circuit for the first interconnection 346d connected to the plurality of first interconnections 346, a circuit for the second interconnection 347d connected to the plurality of second interconnections 347, and a control circuit 345 connected to the circuit for the first interconnection 346d and the circuit for the second interconnection 347d, for example.

The pressure sensor 310 can make high-sensitivity pressure sensing with a small size. Thus, a high-definition touch panel can be provided.

The pressure sensor according to the first embodiment can be used for various pressure sensor devices such as atmospheric pressure sensors and air pressure sensors for tires, as well as the uses mentioned above.

The embodiment can provide a pressure sensor, a microphone, a blood pressure sensor, and a touch panel of high sensitivity.

Hereinabove, embodiments of the invention are described with reference to specific examples. However, the invention is not limited to these specific examples. For example, one skilled in the art may appropriately select specific configurations of components of pressure sensors, microphones, blood pressure sensors, and touch panels such as film units, sensing elements, first magnetic layers, second magnetic layers, and intermediate layers from known art and similarly practice the invention. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all pressure sensors, microphones, blood pressure sensors, and touch panels practicable by an appropriate design modification by one skilled in the art based on the pressure sensors, the microphones, the blood pressure sensors, and the touch panels described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A pressure sensor comprising:
   a support;
   a film unit supported by the support, the film unit having an upper surface, and being deformable; and
   a first sensing element provided on the upper surface,
   the first sensing element including:
      a first magnetic layer, a magnetization of the first magnetic layer being configured to change in accordance with a deformation of the film unit;
      a second magnetic layer provided apart from the first magnetic layer in a direction crossing the upper surface; and
      a first intermediate unit including a first intermediate layer including a portion provided between the first magnetic layer and the second magnetic layer, the first magnetic layer extending in a first direction parallel to the upper surface, a first major axis length of the first magnetic layer in the first direction being longer than a first minor axis length of the first magnetic layer in a second direction parallel to the upper surface and crossing the first direction, and the second magnetic layer extending in the second direction, a second major axis length of the second magnetic layer in the second direction being longer than a second minor axis length of the second magnetic layer in the first direction.

2. The sensor according to claim 1, wherein
the first intermediate unit has a first intermediate unit region,
the first magnetic layer has an overlapping region where the first magnetic layer overlaps the second magnetic layer, and
an outer edge of the first intermediate unit region in a plane parallel to the upper surface is located inside an outer edge of the overlapping region in the plane.

3. The sensor according to claim 1, wherein
the first intermediate unit has a first intermediate unit region,
the first magnetic layer has an overlapping region where the first magnetic layer overlaps the second magnetic layer, and
a shape of the first intermediate unit in a plane parallel to the upper surface is same as a shape of the overlapping region in the plane.

4. The sensor according to claim 1, wherein
a shape of the first intermediate unit in a plane parallel to the upper surface is same as a shape of the first magnetic layer in the plane.

5. The sensor according to claim 1, wherein
the first intermediate unit further includes a first intermediate magnetic layer provided between the first intermediate layer and the first magnetic layer.

6. The sensor according to claim 1, wherein
the first intermediate unit further includes a second intermediate magnetic layer provided between the first intermediate layer and the second magnetic layer.

7. The sensor according to claim 1, wherein
an angle between the first direction and the second direction is not less than 60 degrees and not more than 120 degrees.

8. The sensor according to claim 1, wherein
an angle between the first direction and the second direction is larger than 0 degrees and smaller than 90 degrees.

9. The sensor according to claim 1, wherein
an angle between the first direction and the second direction is larger than 90 degrees and smaller than 180 degrees.

10. The sensor according to claim 1, wherein
an angle between the magnetization of the first magnetic layer and a magnetization of the second magnetic layer is not less than 80 degrees and not more than 100 degrees.

11. The sensor according to claim 1, wherein
an angle between the magnetization of the first magnetic layer and a magnetization of the second magnetic layer is larger than 0 degrees and smaller than 90 degrees.

12. The sensor according to claim 1, wherein
an angle between the magnetization of the first magnetic layer and a magnetization of the second magnetic layer is larger than 90 degrees and smaller than 180 degrees.

13. The sensor according to claim 1, wherein
a difference between an absolute value of a first angle and an absolute value of a second angle is 5 degrees and less,
the first angle is between a first straight line and the first direction, the first straight line passes through a centroid of the upper surface and a centroid of a region where the first magnetic layer overlaps the second magnetic layer, and
the second angle is between the first straight line and the second direction.

14. The sensor according to claim 13, wherein
the absolute value of the first angle is not less than 30 degrees and not more than 60 degrees.

15. The sensor according to claim 13, wherein
the absolute value of the first angle is not less than 45 degrees and not more than 90 degrees.

16. The sensor according to claim 13, wherein
the absolute value of the first angle is not less than 0 degrees and not more than 45 degrees.

17. The sensor according to claim 1, wherein
a difference between an absolute value of a third angle and an absolute value of a fourth angle is 5 degrees or less,
the third angle is between a second straight line and the first direction, the second straight line connects by a shortest distance an outer edge of the upper surface and a centroid of a region where the first magnetic layer overlaps the second magnetic layer, and
the fourth angle is between the second straight line and the second direction.

18. The sensor according to claim 17, wherein
the absolute value of the third angle is not less than 30 degrees and not more than 60 degrees.

19. The sensor according to claim 17, wherein
the absolute value of the third angle is not less than 45 degrees and not more than 90 degrees.

20. The sensor according to claim 17, wherein
the absolute value of the third angle is not less than 0 degrees and not more than 45 degrees.

21. The sensor according to claim 1,
further comprising a second sensing element provided on the upper surface,
a centroid of the film unit being disposed between the first sensing element and the second sensing element,
the second sensing element including:
a third magnetic layer, a magnetization of third magnetic layer being configured to change in accordance with the deformation of the film unit;
a fourth magnetic layer provided apart from the third magnetic layer in the direction crossing the upper surface; and
a second intermediate unit including a second intermediate layer including a portion provided between the third magnetic layer and the fourth magnetic layer,
the third magnetic layer extending in a third direction parallel to the upper surface, a third major axis length of the third magnetic layer in the third direction being longer than a third minor axis length of the third magnetic layer in a fourth direction parallel to the upper surface and crossing the third direction, and
the fourth magnetic layer extending in the fourth direction, a fourth major axis length of the fourth magnetic layer in the fourth direction being longer than a fourth minor axis length of the fourth magnetic layer in the third direction.

22. The sensor according to claim 21, wherein
the first magnetic layer has a first overlapping region where the first magnetic layer overlaps the second magnetic layer,
the third magnetic layer has a second overlapping region where the third magnetic layer overlaps the fourth magnetic layer,
a difference between an absolute value of a first angle and an absolute value of a fifth angle is 5 degrees or less,
the first angle is between a first straight line and the first direction, the first straight line passes through a centroid of the upper surface and a centroid of the first overlapping region, and
the fifth angle is between a third straight line and the third direction, the third straight line passes through the centroid of the upper surface and a centroid of the second overlapping region.

23. The sensor according to claim 21, wherein
the first magnetic layer has a first overlapping region where the first magnetic layer overlaps second magnetic layer,
the third magnetic layer has a second overlapping region where the third magnetic layer overlaps the fourth magnetic layer,
a difference between an absolute value of a third angle and an absolute value of a sixth angle is 5 degrees or less,
the third angle is between a second straight line and the first direction, the second straight line connects an outer edge of the upper surface and a centroid of the first overlapping region by a shortest distance, and
the sixth angle is between a fourth straight line and the third direction, the fourth straight line connects an outer edge of the upper surface and a centroid of the second overlapping region by a shortest distance.

24. The sensor according to claim 21, further comprising a third sensing element provided on the upper surface and a fourth sensing element provided on the upper surface,
the centroid of the film unit being disposed between the third sensing element and the fourth sensing element,
a direction from the third sensing element toward the fourth sensing element crossing a direction from the first sensing element toward the second sensing element,
the third sensing element including:
a fifth magnetic layer, a magnetization of the fifth magnetic layer being configured to change in accordance with the deformation of the film unit;
a sixth magnetic layer provided apart from the fifth magnetic layer in the direction crossing the upper surface; and
a third intermediate unit including a third intermediate layer including a portion provided between the fifth magnetic layer and the sixth magnetic layer,
the fifth magnetic layer extending in a fifth direction parallel to the upper surface, a fifth major axis length of the fifth magnetic layer in the fifth direction being longer than a fifth minor axis length of the fifth magnetic layer in a sixth direction parallel to the upper surface and crossing the fifth direction,
the sixth magnetic layer extending in the sixth direction, a sixth major axis length of the sixth magnetic layer in the sixth direction being longer than a sixth minor axis length of the sixth magnetic layer in the fifth direction,
the fourth sensing element including:
a seventh magnetic layer, a magnetization of the seventh magnetic layer being configured to change in accordance with the deformation of the film unit;
an eighth magnetic layer provided apart from the seventh magnetic layer in the direction crossing the upper surface; and
a fourth intermediate unit including a fourth intermediate layer including a portion provided between the seventh magnetic layer and the eighth magnetic layer,
the seventh magnetic layer extending in a seventh direction parallel to the upper surface, a seventh major axis length of the seventh magnetic layer in the seventh direction being longer than a seventh minor axis length of the seventh magnetic layer in an eighth direction parallel to the upper surface and crossing the seventh direction, and
the eighth magnetic layer extending in the eighth direction, an eighth major axis length of the eighth magnetic layer in the eighth direction being longer than an eighth minor axis length of the eighth magnetic layer in the seventh direction.

25. The sensor according to claim 1, wherein the first sensing element is provided in a plurality, and the first sensing elements are provided on the upper surface.

26. The sensor according to claim 25, wherein at least two of the first sensing elements are electrically connected in series.

27. The sensor according to claim 1, wherein
the first major axis length is not less than 0.1 micrometers and not more than 60 micrometers and
the second major axis length is not less than 0.1 micrometers and not more than 60 micrometers.

28. A microphone comprising the pressure sensor according to claim 1.

29. A blood pressure sensor comprising the pressure sensor according to claim 1.

30. A touch panel comprising the pressure sensor according to claim 1.

* * * * *